US 10,888,623 B2

(12) United States Patent
Kudirka et al.

(10) Patent No.: US 10,888,623 B2
(45) Date of Patent: *Jan. 12, 2021

(54) HYDRAZINYL-INDOLE COMPOUNDS AND METHODS FOR PRODUCING A CONJUGATE

(71) Applicant: Redwood Bioscience, Inc., Emeryville, CA (US)

(72) Inventors: Romas Alvydas Kudirka, El Cerrito, CA (US); Aaron Edward Albers, San Francisco, CA (US); Robyn M. Barfield, Emeryville, CA (US); David Rabuka, Kensington, CA (US)

(73) Assignee: Redwood Bioscience, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/392,162

(22) Filed: Apr. 23, 2019

(65) Prior Publication Data
US 2019/0314509 A1    Oct. 17, 2019

Related U.S. Application Data

(60) Continuation of application No. 15/799,846, filed on Oct. 31, 2017, now Pat. No. 10,314,919, which is a division of application No. 15/057,847, filed on Mar. 1, 2016, now Pat. No. 9,833,515, which is a division of application No. 13/794,159, filed on Mar. 11, 2013, now Pat. No. 9,310,374.

(60) Provisional application No. 61/727,603, filed on Nov. 16, 2012.

(51) Int. Cl.
| | | |
|---|---|---|
| A61K 47/54 | (2017.01) | |
| A61K 47/64 | (2017.01) | |
| A61K 47/68 | (2017.01) | |
| A61K 49/00 | (2006.01) | |
| G01N 33/58 | (2006.01) | |

(52) U.S. Cl.
CPC ............ *A61K 47/545* (2017.08); *A61K 47/64* (2017.08); *A61K 47/6803* (2017.08); *A61K 47/6851* (2017.08); *A61K 47/6889* (2017.08); *A61K 49/0041* (2013.01); *A61K 49/0058* (2013.01); *G01N 33/582* (2013.01)

(58) Field of Classification Search
CPC ........ A61K 47/54; A61K 47/64; A61K 47/68; A61K 49/00; G01N 33/58
See application file for complete search history.

(56) References Cited

U.S. PATENT DOCUMENTS

| | | |
|---|---|---|
| 4,179,337 A | 12/1979 | Davis et al. |
| 4,352,995 A | 10/1982 | Yoshida et al. |
| 4,802,655 A | 2/1989 | Bates |
| 4,816,567 A | 3/1989 | Cabilly et al. |
| 4,935,496 A | 6/1990 | Kudo et al. |
| 5,075,046 A | 12/1991 | Stoll |
| 5,089,261 A | 2/1992 | Nitecki et al. |
| 5,100,992 A | 3/1992 | Cohn et al. |
| 5,134,192 A | 7/1992 | Eijen et al. |
| 5,166,309 A | 11/1992 | Maj et al. |
| 5,171,264 A | 12/1992 | Merril |
| 5,213,891 A | 5/1993 | Maj et al. |
| 5,219,564 A | 6/1993 | Zalipsky et al. |
| 5,225,539 A | 7/1993 | Winter |
| 5,275,838 A | 1/1994 | Merrill |
| 5,281,698 A | 1/1994 | Nitecki |
| 5,298,643 A | 3/1994 | Greenwald |
| 5,312,808 A | 5/1994 | Shorr et al. |
| 5,321,095 A | 6/1994 | Greenwald |
| 5,324,844 A | 6/1994 | Zalipsky |
| 5,349,001 A | 9/1994 | Greenwald |
| 5,352,756 A | 10/1994 | Meldal |
| 5,405,877 A | 4/1995 | Greenwald et al. |
| 5,446,090 A | 8/1995 | Harris |
| 5,455,027 A | 10/1995 | Zalipsky et al. |
| 5,470,829 A | 11/1995 | Prisell et al. |
| 5,478,805 A | 12/1995 | Shorr et al. |
| 5,502,167 A | 3/1996 | Waldmann et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,422 A | 10/1996 | Greenwald |
| 5,585,089 A | 12/1996 | Queen et al. |
| 5,605,976 A | 2/1997 | Martinez et al. |
| 5,612,460 A | 3/1997 | Zalipsky |
| 5,614,549 A | 3/1997 | Greenwald et al. |
| 5,618,528 A | 4/1997 | Coper et al. |

(Continued)

FOREIGN PATENT DOCUMENTS

| | | |
|---|---|---|
| EP | 0239400 | 9/1987 |
| EP | 0519596 | 12/1992 |

(Continued)

OTHER PUBLICATIONS

Nakagawa et al. (1988) "New Evidence for the Presence of a Spiroindolenine Intermediate in Pictet-Spengler Reaction of Nb-Hydroxytryptamine," J. Chem. Soc. 463-464.

Pandit & Seshadri (1974) "Synthetic studies in the indole series. Synthesis of potential pharmacological agents," Indian Journal of Chemistry 12(9) 943-945.

Van Maarseveen et al. (1993) "Intramolecular Pictet-Spengler Reaction of Nb-Alkoxytryptamines. 4. A Study towards Diastereocontrol in the Synthesis of Tetracyclic Eudistomins," Tetrahedron 49(11): 2325-2344.

(Continued)

*Primary Examiner* — Brenda L Coleman
(74) *Attorney, Agent, or Firm* — Rudy J. Ng; Boziceivc, Field & Francis LLP

(57) ABSTRACT

The present disclosure provides conjugate structures (e.g., polypeptide conjugates) and hydrazinyl-indole compounds used to produce these conjugates. The disclosure also provides methods of production of such conjugates, as well as methods of using the same.

15 Claims, 9 Drawing Sheets

(56) References Cited

U.S. PATENT DOCUMENTS

| | | | |
|---|---|---|---|
| 5,637,749 A | 6/1997 | Greenwald | |
| 5,643,575 A | 7/1997 | Martinez et al. | |
| 5,650,388 A | 7/1997 | Shorr et al. | |
| 5,672,662 A | 9/1997 | Harris et al. | |
| 5,681,567 A | 10/1997 | Martinez et al. | |
| 5,686,110 A | 11/1997 | Greenwald et al. | |
| 5,693,493 A | 12/1997 | Robinson et al. | |
| 5,698,417 A | 12/1997 | Robinson et al. | |
| 5,705,154 A | 1/1998 | Dalie et al. | |
| 5,730,990 A | 3/1998 | Greenwald et al. | |
| 5,739,208 A | 4/1998 | Harris | |
| 5,750,078 A | 5/1998 | Shitara et al. | |
| 5,756,593 A | 5/1998 | Martinez et al. | |
| 5,770,403 A | 6/1998 | Dalie et al. | |
| 5,808,096 A | 9/1998 | Zalipsky | |
| 5,824,778 A | 10/1998 | Ishikawa et al. | |
| 5,824,784 A | 10/1998 | Kinstler et al. | |
| 5,840,900 A | 11/1998 | Greenwald et al. | |
| 5,874,500 A | 2/1999 | Rhee et al. | |
| 5,880,131 A | 3/1999 | Greenwald et al. | |
| 5,900,461 A | 5/1999 | Harris | |
| 5,902,588 A | 5/1999 | Greenwald et al. | |
| 5,919,442 A | 7/1999 | Yin et al. | |
| 5,919,455 A | 7/1999 | Greenwald et al. | |
| 5,932,462 A | 8/1999 | Harris et al. | |
| 5,965,119 A | 10/1999 | Greenwald et al. | |
| 5,965,566 A | 10/1999 | Greenwald et al. | |
| 5,985,263 A | 11/1999 | Lee et al. | |
| 5,990,237 A | 11/1999 | Bentley et al. | |
| 6,011,042 A | 1/2000 | Greenwald et al. | |
| 6,013,283 A | 1/2000 | Greenwald et al. | |
| 6,077,939 A | 6/2000 | Wei et al. | |
| 6,113,906 A | 9/2000 | Greenwald et al. | |
| 6,127,355 A | 10/2000 | Greenwald et al. | |
| 6,177,087 B1 | 1/2001 | Greenwald et al. | |
| 6,180,095 B1 | 1/2001 | Greenwald et al. | |
| 6,194,580 B1 | 2/2001 | Greenwald et al. | |
| 6,214,966 B1 | 4/2001 | Harris | |
| 7,598,257 B2 | 10/2009 | Rodgers et al. | |
| 2004/0086979 A1 | 5/2004 | Zhang et al. | |
| 2005/0033031 A1 | 2/2005 | Couto | |
| 2007/0135485 A1 | 2/2007 | Gillig et al. | |
| 2008/0031823 A1 | 2/2008 | Bornhop et al. | |
| 2017/0049907 A1 | 2/2017 | Rabuka et al. | |

FOREIGN PATENT DOCUMENTS

| | | |
|---|---|---|
| EP | 0592106 | 4/1994 |
| WO | 199013540 | 11/1990 |
| WO | 199109967 | 7/1991 |
| WO | 199200748 | 1/1992 |
| WO | 199216555 | 10/1992 |
| WO | 199404193 | 3/1994 |
| WO | 199414758 | 7/1994 |
| WO | 199417039 | 8/1994 |
| WO | 199418247 | 8/1994 |
| WO | 199428937 | 12/1994 |
| WO | 199511924 | 5/1995 |
| WO | 199513312 | 5/1995 |
| WO | 199600080 | 1/1996 |
| WO | 199621469 | 7/1996 |
| WO | 199623794 | 8/1996 |
| WO | 199703106 | 1/1997 |
| WO | 199807713 | 2/1998 |
| WO | 199841562 | 9/1998 |
| WO | 199845331 | 10/1998 |
| WO | 199845332 | 10/1998 |
| WO | 199848837 | 11/1998 |
| WO | 199930727 | 6/1999 |
| WO | 199932134 | 7/1999 |
| WO | 199933483 | 7/1999 |
| WO | 199945964 | 9/1999 |
| WO | 199953951 | 10/1999 |
| WO | 200126692 | 4/2001 |
| WO | 2006121820 | 11/2006 |
| WO | 2007023143 | 3/2007 |
| WO | 2007027248 | 3/2007 |
| WO | 2008008398 | 1/2008 |
| WO | 2008019303 | 2/2008 |
| WO | 2010117939 | 10/2010 |
| WO | 2012078777 | 6/2012 |

OTHER PUBLICATIONS

Van Maarseveen et al. (1995) "An Approach to Canthine Derivatives Using the Intramolecular Pictet-Spengler Condensation," Tetrahedron 51(16): 4841-4852.

Zheng et al. (2008) "Synthesis of Indole Derivatives by Cyclization of Oxo-N-Acyliminium Ions," Synthesis 9: 1345-1350.

Agarwal, et al. "Hydrazino-Pictet-Spengler Ligation as a Biocompatible Method for the 1-44 Generation of Stable Protein Conjugates. Bioconjugate Chemistry" American Chemistry Society 24:846-851 (2013).

Mahmoud et al., (2007) "Utility of Nitriles in Synthesis of Pyrido[2,3-d]pyrimidines, Thiazolo [3,2-a]pyridines, Pyrano [2,3-b]benzopyrrole, and Pyrido [2, 3-d] benzopyrroles" Phosphorus, Sulfur and Silicon and the Related Elements 182(11) : 2507-2521 (XP055280235).

Pubchem 1H-indole-2-carbohydrazide, CID 231954, pp. 1-8, Create Date: Mar. 26, 2005 [retrieved on Feb. 20, 2014]. Retrieved from the Internet: <URL: http://pubchem.ncbi.nlm.nih.gov/summary/summary.cgi?cid=231954&1oc=ec_rcs>; p. 1, 2D structure.

Pubchem CID 12343703, pp. 1-2, Create Date: Feb. 8, 2007 [retrieved on Feb. 6, 2014]. Retrieved from the Internet: <URL: http://pubchem.ncbi.nlm.nih.gov/summary/summary.cgi?cid=12343703&1oc=ec_rcs>; p. 1, 2D structure.

Pubchem CTK2E1080, CID 12343698, pp. 1-3, Create Date: Feb. 8, 2007 [retrieved on Feb. 6, 2014].Retrieved from the Internet: <URL: http://pubchem.ncbi.nlm.nih.gov/summary/summary.cgi?cid=12343698&1oc=ec_rcs>; p. 1, 20 structure.

Pubchem SureCN743887, CID 66787168, pp. 1-2, Create Date: Nov. 30, 2012 [retrieved on Feb. 6, 2014]. Retrieved from the Internet: <URL: http://pubchem.ncbi.nlm.nih.gov/summary/summary.cgi?cid=6787168&1oc=ec_rcs>; p. 1, 2D structure.

Padlan "A possible procedure for reducing the immunogenicity of antibody variable domains while preserving their ligand-binding properties" Mol Immunol 28(4-5):489-498 (1991).

Riechmann, et al. "Reshaping human antibodies for therapy" Nature 332(6162):323-327 (1988).

Roguska. et al. "Humanization of murine monoclonal antibodies through variable domain resurfacing" PNAS 91(3):969-973(1994).

Studnicka et al. "Human-engineered monoclonal antibodies retain full specific binding activity by preserving non-CDR complementarity-modulating residues." Protein Eng 7(6):805-814 (1994).

Zeng et al., (2009) "High-efficiency labeling of sialylated glycoproteins on living cells," Nat. Methods 6(3):207-209.

Stockigt et al., (2011) "The Pictet-Spengler Reaction in Nature and in Organic Chemistry," Angew. Chem. Int. Ed. 50: 8538-8564.

Alam et al., (2010) "Functionalization of Peptides and Proteins by Mukaiyama Aldol Reaction," J. Am. Chem. Soc. 132(28):9546-9548.

Alam et al., (2011) "Indium mediated allylation in peptide and protein functionalization," Chem. Commun. 47(32):9066-9068.

Carrico et al., (2007) "Introducing genetically encoded aldehydes into proteins," Nat. Chem. Biol. 3(6):321-322.

Chen et al., (2005) "Site-specific labeling of cell surface proteins with biophysical probes using biotin ligase," Nat. Methods 2(2):99-104.

Cho et al., (2011) "Optimized clinical performance of growth hormone with an expanded genetic code," Proc. Natl. Acad. Sci. USA 108(22):9060-9065.

Dirksen et al., (2006) "Nucleophilic Catalysis of Oxime Ligation," Angew. Chem. Int. Ed. 45(45):7581-7584.

Ducry & Stump (2009) "Antibody-Drug Conjugates: Linking Cytotoxic Payloads to Monoclonal Antibodies," Bioconjugate Chem. 21(1):5-13.

(56) References Cited

OTHER PUBLICATIONS

Esser-Kahn & Francis (2008) "Protein-Cross-Linked Polymeric Materials through Site-Selective Bioconjugation," Angew Chem. Int. Ed. 47(20):3751-3754.
Geoghegan & Stroh (1992) "Site-Directed Conjugation of Nonpeptide Groups to Peptides and Proteins via Periodate-Oxidation of a 2-Amino Alcohol—Application to Modification at N-Terminal Serine," Bioconjugate Chem. 3(2):138-146.
Gilmore et al., "N-Terminal Protein Modification through a Biomimetic Transamination Reaction," Angew. Chem. Int. Ed. 45(32):5307-5311.
Glazer (1970) "Specific Chemical Modification of Proteins," Annu. Rev. Biochem. 39(1): 101-130.
Hang & Bertozzi (2001) "Ketone Isosteres of 2-N-Acetamidosugars as Substrates for Metabolic Cell Surface Engineering," J. Am. Chem. Soc. 123(6):1242-1243.
Hermkens et al., (1990) "Syntheses of 1,3-disubstituted N-oxy-β-carbolines by the PictetSpengler reactions of N-oxy-tryptophan and -tryptamine derivatives," Tetrahedron 46(3):833-846.
Hudak et al., (2012) "Synthesis of Heterobifunctional Protein Fusions Using Copper-Free Click Chemistry and the Aldehyde Tag," Angew. Chem. Int. Ed. 51(17):4161-4165.
Hudak et al., (2011) "Protein Glycoengineering Enabled by the Versatile Synthesis of Aminooxy Glycans and the Genetically Encoded Aldehyde Tag," J. Am. Chem. Soc. 133(40):16127-16135.
Hutchins et al., (2011) "Selective Formation of Covalent Protein Heterodimers with an Unnatural Amino Acid," Chem. Biol. 18(3):299-303.
Ishikawa et al., (2001), Novel [2-3]-Sigmatropic Rearrangement for Carbon-Nitrogen Bond Formation J. Am. Chem. Soc. 123(31):7734-7735.
Jameson & Ross (2010) "Fluorescence Polarization/Anisotropy in Diagnostics and Imaging," Chem. Rev. 110(5):2685-2708.
Jencks (1964) "Simple Carbonyl Group Reactions," Prog. Phys. Org. Chem. 2:63-128.
Kalia & Raines (2008) "Hydrolytic Stability of Hydrazones and Oximes," Angew. Chem. Int. Ed. 47(39):7523-7526.
Kim et al. (2012) "Synthesis of Bispecific Antibodies using Genetically Encoded Unnatural Amino Acids," J. Am. Chem. Soc. 134(24):9918-9921.
Kirkup et al., (1989) "A concise route to the oxathiazepine containing eudistomin skeleton and some carba-analogs," Tetrahedron Lett. 30(49):6809-6812.
Krop et al. (2012) "A Phase II Study of Trastuzumab Emtansine in Patients With Human Epidermal Growth Factor Receptor 2-Positive Metastatic Breast Cancer Who Were Previously Treated With Trastuzumab, Lapatinib, an Anthracycline, a Taxane, and Capecitabine," Journal of Clinical Oncology 30(26): 3234-324.
Lee et al., (2011) "Thiourea-Catalyzed Enantioselective Iso-PictetSpengler Reactions," Org. Lett. 13(20):5564-5567.
Mahal et al., (1997) "Engineering Chemical Reactivity on Cell Surfaces Through Oligosaccharide Biosynthesis," Science, 276: 1125-1128.
Maresh et al. (2007) "Strictosidine Synthase: Mechanism of a Pictet-Spengler Catalyzing Enzyme," J. Am. Chem. Soc. 130(2):710-723.
Michalet et al., (2006) "Single-Molecule Fluorescence Studies of Protein Folding and Conformational Dynamics," Chem. Rev. 106(5):1785-1813.
Molina et al., (1996) "Regiospecific preparation of γ-carbolines and pyrimido[3, 4-a]indole derivatives by intramolecular ring-closure of heterocumulene-substituted indoles," Tetrahedron 52(16):5833-5844.
Mueller et al., (1990) Antibody conjugates with morpholinodoxorubicin and acid cleavable linkers, Bioconjugate Chem. 1(5):325-330.
Nystrom (2005) "Role of oxidative carbonylation in protein quality control and senescence," EMBOJ 24(7):1311-1317.
O'Shannessy et al., (1987) "Quantitation of glycoproteins on electroblots using the biotin-streptavidin complex," Anal. Biochem. 163(1):204-209.
Plate et al., (1987) "Synthesis of 2-hydroxy-3-(ethoxycarbonyl)-1,2,3,4-tetrahydro-β-carbolines from N-hydroxytryptophans. An approach to the eudistomin series," J. Org. Chem. 52(4):555-560.
Rabuka et al., (2012) "Site-specific chemical protein conjugation using genetically encoded aldehyde tags," Nat. Protoc. 7(6):1052-1067.
Rashidian (2012) "Chemoenzymatic Reversible Immobilization and Labeling of Proteins without Prior Purification," J. Am. Chem. Soc. 134(20):8455-8467.
Sadamoto et al., (2004) "Control of Bacteria Adhesion by Cell-Wall Engineering," J. Am. Chem. Soc. 126(12):3755-3761.
Sasaki et al., (2008) "N-terminal labeling of proteins by the Pictet-Spengler reaction," Bioorg. Med. Chem. Lett. 18(16):4550-4553.
Scheck et al., (2008) "Optimization of a Biomimetic Transamination Reaction," J. Am. Chem. Soc. 130(35):11762-11770.
Shen et al,. (2012) "Conjugation site modulates the in vivo stability and therapeutic activity of antibody-drug conjugates," Nat. Biotechnol. 30(2):184-189.
Shi et al. (2012) "Quantitative fluorescence labeling of aldehyde-tagged proteins for singlemolecule imaging," Nat. Methods 9(5):499-503.
Sletten & Bertozzi, (2009) "Bioorthogonal Chemistry: Fishing for Selectivity in a Sea of Functionality," Agnew Chem. Soc. 48(38):6974-6998.
Smith et al. (1991) "Excess brain protein oxidation and enzyme dysfunction in normal aging and in Alzheimer disease," Proc. Natl. Acad. Sci. USA 88(23):10540-10543.
Stephanopoulos & Francis, (2011) "Choosing an effective protein bioconjugation strategy," Nat. Chem. Biol. 7(12):876-884.
Tai et al., (2004) "Parallel Identification of O-GlcNAc-Modified Proteins from Cell Lysates," J. Am. Chem. Soc. 126(34):10500-10501.
Tsunoda et al., (1993) "1,1'-(azodicarbonyl)dipiperidine-tributylphosphine, a new reagent system for mitsunobu reaction," Tetrahedron Lett. 34(10):1639-1642.
Wang et al., (2003) "Addition of the keto functional group to the genetic code of *Escherichia coli*," Proc. Natl. Acad. Sci. USA 100(1):56-61.
Witus et al., (2010) "Identification of Highly Reactive Sequences for PLP-Mediated Bioconjugation Using a Combinatorial Peptide Library," J. Am. Chem. Soc. 132(47):16812-16817.
Wong et al., (2009) "Selective Covalent Protein Immobilization: Strategies and Applications," Chem. Rev. 109(9):4025-4053.
Wu et al., (2009) "Site-specific chemical modification of recombinant proteins produced in mammalian cells by using the genetically encoded aldehyde tag," Proc. Natl. Acad. Sci. USA 106:3000-3005.
Yeom et al., (2007) "1,8-Diazabicylo[5.4.0]undec-7-ene (DBU)-promoted efficient and versatile aza-Mchael addition," Tetrahedron 63(4):904-909.
Yi et al., (2010) "A Highly Efficient Strategy for Modification of Proteins at the C Terminus," Angew. Chem. Int. Ed. 49(49):9417-9421.
Pudlo et al., (1998) "Synthesis and Antiviral Activity of Certain 4 and 4,5-Disubstituted 7-[(2-Hydroxyethoxy) methyl] pyrrolo[2,3-d]pyrimidines," J. Med. Chem 31(11) 2086-2092.
Seela et al., (1994) "Synthesis of pyrrolo[3,2-c] pyridine and pyrazolo[3,4-d] pyrimidine B-d-arabinonucleosides via gucleobase anion glycosylation" Nucleosides & Nucleotides 10(1-3) 713-714.
Smith et al. (1974) "Improved methods for the study of drug effects of purine metabolism and their application to nebularine and 7-deazanebularine," Biotechnology Pharmacology 23(14) 2023-2035.

A

B

C

HYDRAZINYL-INDOLE COMPOUNDS AND METHODS FOR PRODUCING A CONJUGATE

CROSS-REFERENCE TO RELATED APPLICATIONS

This application is a continuation of U.S. application Ser. No. 15/799,846, filed Oct. 31, 2017, now U.S. Pat. No. 10,314,919, which is a divisional of U.S. application Ser. No. 15/057,847, filed Mar. 1, 2016, now U.S. Pat. No. 9,833,515, which is a divisional of U.S. application Ser. No. 13/794,159, filed Mar. 11, 2013, now U.S. Pat. No. 9,310,374, which claims priority pursuant to 35 U.S.C. § 119(e) to U.S. Provisional Application No. 61/727,603, filed Nov. 16, 2012, the disclosures of each of which are incorporated herein by reference.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

A number of standard chemical transformations are commonly used to create and manipulate post-translational modifications on proteins. There are a number of methods where one is able to modify the side chains of certain amino acids selectively. For example, carboxylic acid side chains (aspartate and glutamate) may be targeted by initial activation with a water-soluble carbodiimide reagent and subsequent reaction with an amine. Similarly, lysine can be targeted through the use of activated esters or isothiocyanates, and cysteine thiols can be targeted with maleimides and α-halo-carbonyls.

One significant obstacle to the creation of a chemically altered protein therapeutic or reagent is the production of the protein in a biologically active, homogenous form. Conjugation of a drug or detectable label to a polypeptide can be difficult to control, resulting in a heterogeneous mixture of conjugates that differ in the number of drug molecules attached and in the position of chemical conjugation. In some instances, it may be desirable to control the site of conjugation and/or the drug or detectable label conjugated to the polypeptide using the tools of synthetic organic chemistry to direct the precise and selective formation of chemical bonds on a polypeptide.

SUMMARY

The present disclosure provides conjugate structures and hydrazinyl-indole compounds used to produce these conjugates. The present disclosure also provides methods of production of such conjugates, as well as methods of using the same.

Embodiments of the present disclosure include a conjugate that includes at least one modified amino acid residue of formula (I):

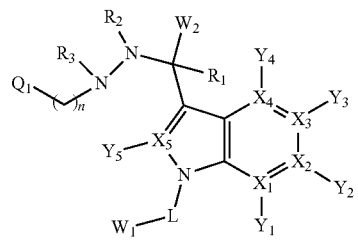

wherein n is 0 or 1;

$R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$X_1$, $X_2$, $X_3$ and $X_4$ are each independently selected from C, N, O and S;

$X_5$ is C;

$Y_1$, $Y_2$, $Y_3$, $Y_4$ and $Y_5$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$Q_1$ is a bond to either $X_4$ or $X_5$, wherein if $Q_1$ is a bond to $X_4$, then $Y_4$ is absent, or if $Q_1$ is a bond to $X_5$, then $Y_5$ is absent; and L is an optional linker, wherein one of $W_1$ and $W_2$ is a polypeptide and the other is a drug or a detectable label.

In some embodiments, $Q_1$ is a bond to $X_4$ and $Y_4$ is absent.

In some embodiments, $Q_1$ is a bond to $X_5$ and $Y_5$ is absent.

In some embodiments, n is 1.

In some embodiments, $R_2$ and $R_3$ are each independently selected from alkyl and substituted alkyl.

In some embodiments, $R_2$ and $R_3$ are each methyl.

In some embodiments, $X_1$, $X_2$, $X_3$ and $X_4$ are each C.

In some embodiments, $Y_1$, $Y_2$ and $Y_3$ are each H, and one of either $Y_4$ or $Y_5$ is H.

In some embodiments, L is present and includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl.

In some embodiments, L is present and includes a polymer. In some embodiments, the polymer is a polyethylene glycol.

In some embodiments, the detectable label includes a fluorophore.

In some embodiments, $W_1$ is the drug or the detectable label, and $W_2$ is the polypeptide.

In some embodiments, $W_1$ is the polypeptide, and $W_2$ is the drug or the detectable label.

In some embodiments, the conjugate includes at least one modified amino acid residue of formula (II):

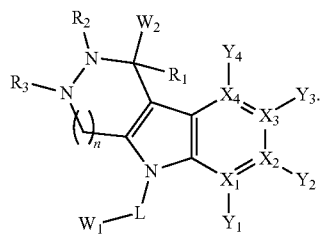

(II)

In some embodiments, the conjugate includes at least one modified amino acid residue of formula (IIa):

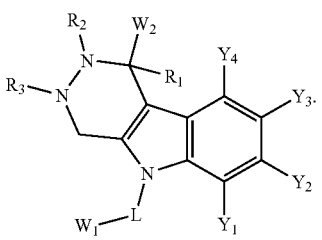

(IIa)

In some embodiments, the conjugate includes at least one modified amino acid residue of formula (III):

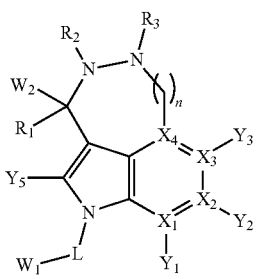

(III)

In some embodiments, the conjugate includes at least one modified amino acid residue of formula (IIIa):

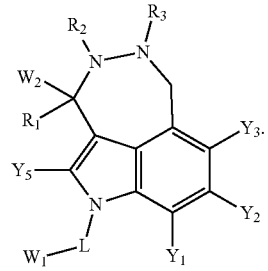

(IIIa)

Embodiments of the present disclosure include a compound of formula (IV):

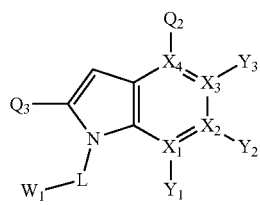

(IV)

wherein one of $Q_2$ and $Q_3$ is —$(CH_2)_n NR_3 NHR_2$ and the other is $Y_4$;

n is 0 or 1;

$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$X_1$, $X_2$, $X_3$ and $X_4$ are each independently selected from C, N, O and S;

$Y_1$, $Y_2$, $Y_3$ and $Y_4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

L is an optional linker; and $W_1$ is selected from a drug, a detectable label and a polypeptide.

In some embodiments, $Q_2$ —$(CH_2)_n NR_3 NHR_2$ and $Q_3$ is $Y_4$.

In some embodiments, $Q_3$ —$(CH_2)_n NR_3 NHR_2$ and $Q_2$ is $Y_4$.

In some embodiments, n is 1.

In some embodiments, $R_2$ and $R_3$ are each independently selected from alkyl and substituted alkyl.

In some embodiments, $R_2$ and $R_3$ are each methyl.

In some embodiments, $X_1$, $X_2$, $X_3$ and $X_4$ are each C.

In some embodiments, $Y_1$, $Y_2$, $Y_3$ and $Y_4$ are each H.

In some embodiments, L is present and includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl.

In some embodiments, L is present and includes a polymer. In some embodiments, the polymer is a polyethylene glycol.

In some embodiments, the detectable label includes a fluorophore.

In some embodiments, the compound is a compound of formula (V):

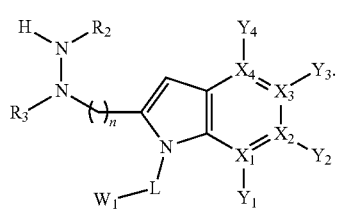

(V)

In some embodiments, the compound is a compound of formula (Va):

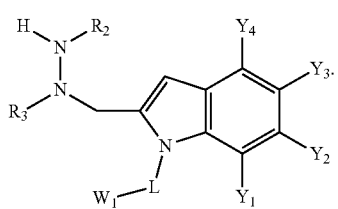

(Va)

In some embodiments, the compound is a compound of formula (VI):

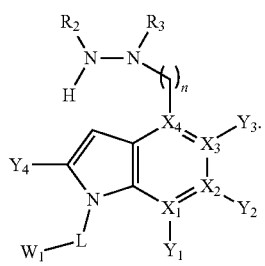

(VI)

In some embodiments, the compound is a compound of formula (VIa):

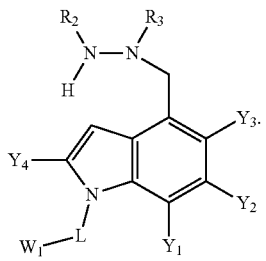

(VIa)

Embodiments of the present disclosure include a method of producing a conjugate. The method includes combining in a reaction mixture a compound of formula (IV) and a second compound that includes a reactive group, where the combining is under reaction conditions suitable to promote reaction between the compound and the reactive group of the second compound to form a conjugate. The method also includes isolating the conjugate from the reaction mixture.

In some embodiments, $W_1$ is the drug or the detectable label, and the second compound is the polypeptide.

In some embodiments, $W_1$ is the polypeptide, and the second compound is the drug or the detectable label.

In some embodiments, the reactive group includes a reactive aldehyde group or a reactive ketone group.

In some embodiments, the reaction mixture includes water.

In some embodiments, the reaction mixture has a pH of 7.

In some embodiments, the reaction conditions are at a temperature of 37° C.

Embodiments of the present disclosure include a pharmaceutical composition that includes a conjugate of formula (I) and a pharmaceutically acceptable excipient.

Embodiments of the present disclosure include a method of delivering a conjugate to a subject. The method includes administering to the subject an effective amount of a conjugate of formula (I).

Embodiments of the present disclosure include a method of treating a condition in a subject. The method includes administering to the subject having the condition a therapeutically effective amount of a pharmaceutical composition that includes a conjugate of formula (I), where the administering is effective to treat the condition in the subject.

BRIEF DESCRIPTION OF THE DRAWINGS

FIG. 2, panel B, shows a schematic of a conjugation reaction of the functionalized detectable label to an antibody, according to embodiments of the present disclosure. FIG. 2, panel C, shows images of SDS-PAGE gels showing the results of the reaction, according to embodiments of the present disclosure.

FIG. 5, panel A, shows the chemical structures of a panel of amines used in the experiment. FIG. 5, panel B, shows a graph of percent conversion to product in sodium citrate (pH 4.0-5.5) or sodium phosphate (pH 6.0-7.5) buffers. Reactions contained 50 µM amine and benzyloxyacetaldehyde and proceeded at room temperature for 2 h prior to HPLC analysis.

FIG. 7, panel A, shows structures of the HIPS ligation reagent (Compound 9), the hydrazide reagent (Compound 10), the Pictet-Spengler ligation reagent (Compound 11), and the aminooxy reagent (Compound 12). Gel scans show the relative labeling of FGly-MBP (FIG. 7, panel B), FGly-α-HER2 (FIG. 7, panel C), and N-terminally transaminated Mb with reagents 9-12 (FIG. 7, panel D). In all cases, buffered protein solutions at pH 6.0 were treated with 400 µM fluorophore for 2 h at 37° C. prior to analysis by SDS-PAGE.

DEFINITIONS

Figure 1:
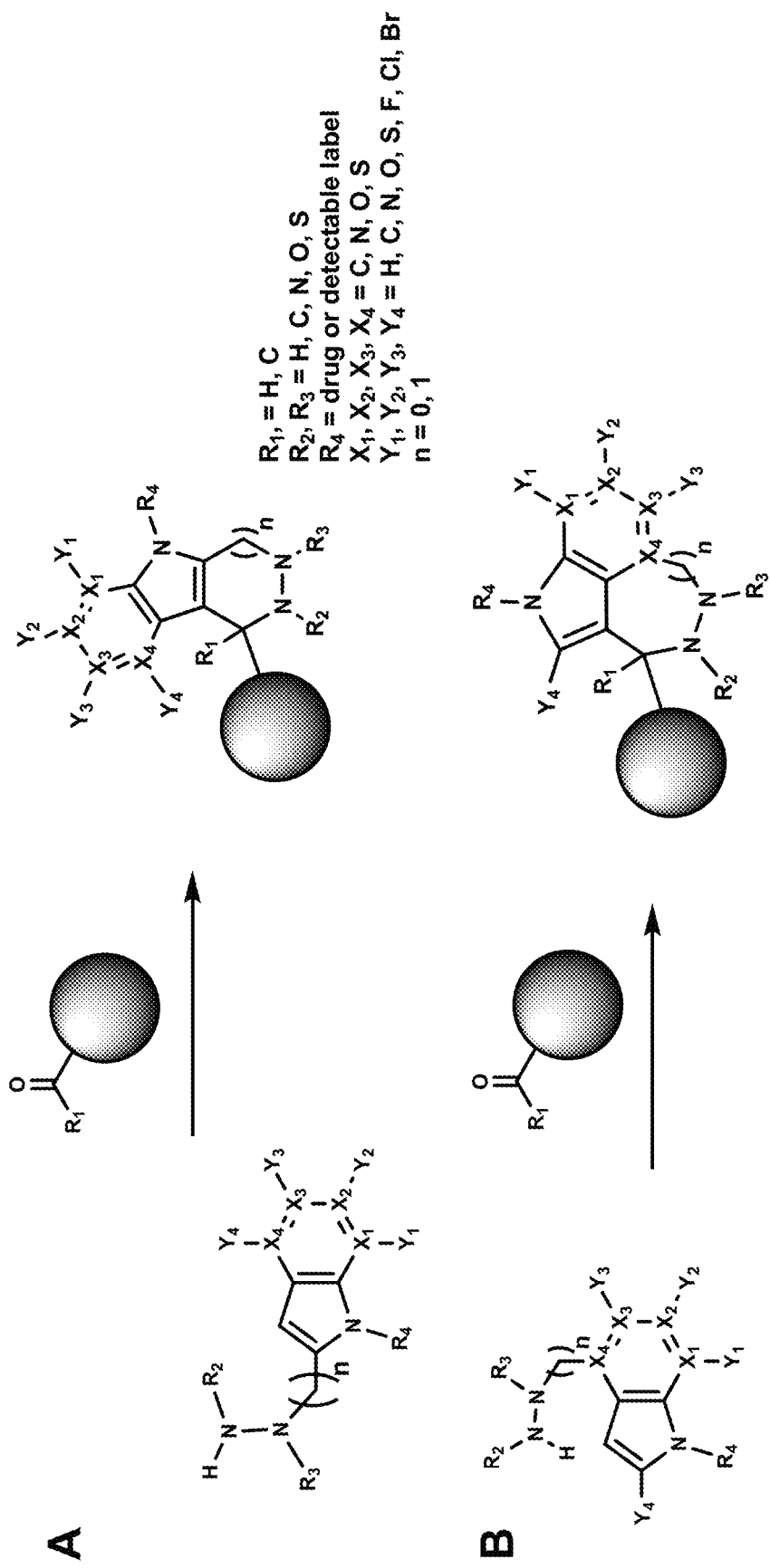
FIG. 1, panel A, and FIG. 1, panel B, show reaction schemes for the production of a polypeptide conjugate that includes a hydrazinyl-indole coupling moiety, according to embodiments of the present disclosure.

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocloooxy, thiol, thioalkoxy, substituted thioalkoxy, aryl, aryloxy, heteroaryl, heteroaryloxy, heterocyclyl, heterocloooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N—O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$OM$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O) NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{s8}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acids also include naturally occurring amino acids in D-, rather than L-form. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of sulfatase motif and Formylglycine Generating Enzyme (FGE), which react to form a reaction product of a converted aldehyde tag containing a formylglycine (fGly) in lieu of cysteine or serine in the motif. Other exemplary reactive partners include an aldehyde of an fGly residue of a converted aldehyde tag and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides conjugates (e.g., polypeptide conjugates), hydrazinyl-indole compounds for producing the conjugates and methods of making and using the same. Embodiments of each are described in more detail in the sections below.

Conjugates

The present disclosure provides conjugates. By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide conjugated to a second moiety. As described in more detail below, the moiety conjugated to the polypeptide can be any of a variety of moieties such as, but not limited to, a detectable label, a drug, a water-soluble polymer, or a moiety for immobilization of the polypeptide to a membrane or a surface. The moiety of interest can be conjugated to the polypeptide at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, a polypeptide may be conjugated to one moiety, e.g., one moiety may be conjugated to a single amino acid residue of the polypeptide. In some cases, a first moiety is conjugated to a first amino acid residue of the polypeptide and a second moiety is conjugated to a second amino acid residue of the polypeptide. Additional moieties may be conjugated to other amino acid residues of the polypeptide.

The one or more amino acid residues that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to a moiety, such that multiple sites in the polypeptide are modified.

Although described herein in terms of a polypeptide conjugated to one or more moieties (e.g., a drug, a detectable label, a polypeptide, etc.), embodiments of the present disclosure also include conjugates where a moiety (e.g., a drug, a detectable label, a polypeptide, etc.) is conjugated to one or more other moieties (e.g., a drug, a detectable label, a polypeptide, etc.). For example, a drug may be conjugated to one or more other moieties (e.g., a drug, a detectable label, a polypeptide, etc.), or in other embodiments, a detectable label may be conjugated to one or more other moieties (e.g., a drug, a detectable label, a polypeptide, etc.). Thus, for instance, embodiments of the present disclosure include, but are not limited to, the following: a conjugate of a polypeptide and a drug; a conjugate of a polypeptide and a detectable label; a conjugate of two or more polypeptides; a conjugate of two or more drugs; a conjugate of two of more detectable labels; a conjugate of a drug and a detectable label; a conjugate of a polypeptide, a drug and a detectable label; a conjugate of a polypeptide and two or more drugs; a conjugate of a polypeptide and two or more detectable labels; a conjugate of a drug and two or more polypeptides; a conjugate of a detectable label and two or more polypeptides; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest together through the coupling moiety. In some cases, the coupling moiety includes a hydrazinyl-indole compound or a derivative of a hydrazinyl-indole compound. For instance, a general scheme for coupling a moiety of interest to a polypeptide through a hydrazinyl-indole coupling moiety is shown in the general reaction scheme below.

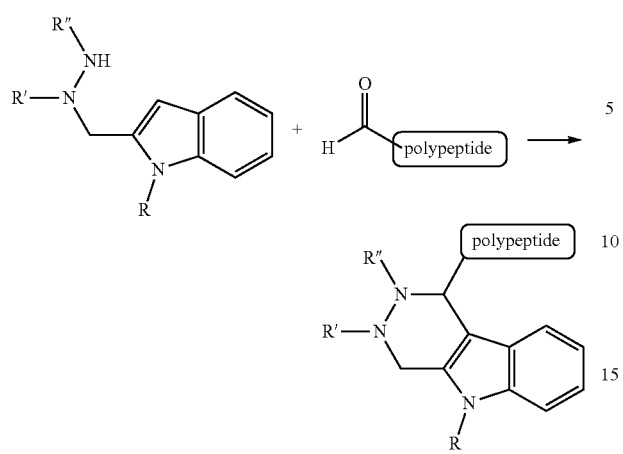

In the reaction scheme above, R may be the moiety of interest conjugated to the polypeptide. As described herein, the moiety can be any of a variety of moieties such as, but not limited to, a detectable label, a drug, a water-soluble polymer, or a moiety for immobilization of the polypeptide to a membrane or a surface of a substrate. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

Other hydrazinyl-indole coupling moieties are also possible. For example, another general scheme for coupling a moiety of interest to a polypeptide through a hydrazinyl-indole coupling moiety is shown in the general reaction scheme below.

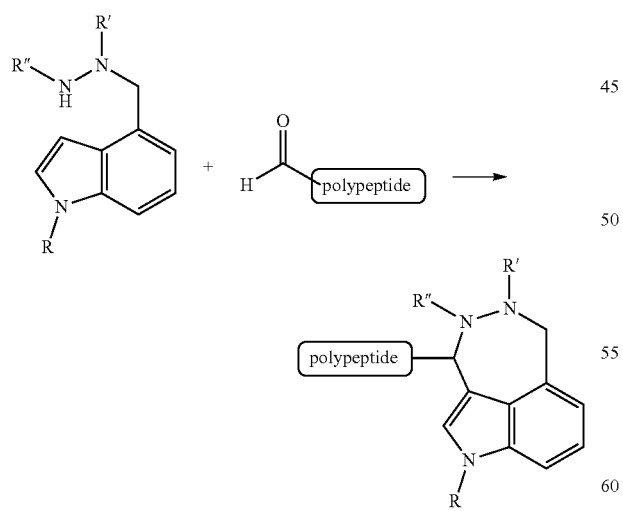

In the reaction scheme above, R may be the moiety of interest conjugated to the polypeptide. As described above, the moiety can be any of a variety of moieties such as, but not limited to, a detectable label, a drug, a water-soluble polymer, or a moiety for immobilization of the polypeptide to a membrane or a surface of a substrate. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. Other coupling moieties are also possible, as shown in the conjugates and compounds described in more detail below.

In certain embodiments, the conjugate includes at least one modified amino acid residue of formula (I):

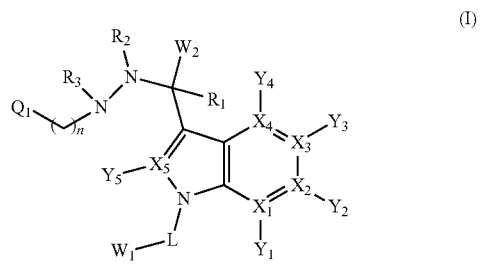

(I)

wherein n is 0 or 1;

$R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$X_1$, $X_2$, $X_3$ and $X_4$ are each independently selected from C, N, O and S;

$X_5$ is C;

$Y_1$, $Y_2$, $Y_3$, $Y_4$ and $Y_5$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$Q_1$ is a bond to either $X_4$ or $X_5$, wherein if $Q_1$ is a bond to $X_4$, then $Y_4$ is absent, or if $Q_1$ is a bond to $X_5$, then $Y_5$ is absent; and L is an optional linker, wherein one of $W_1$ and $W_2$ is a polypeptide and the other is a drug or a detectable label.

In certain embodiments, n is 0 or 1. In certain embodiments, n is 0. In certain embodiments, n is 1.

In certain embodiments, $R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R_1$ is hydrogen. In certain embodiments, $R_1$ is alkyl or substituted alkyl. In certain embodiments, $R_1$ is alkenyl or substituted alkenyl. In certain embodiments, $R_1$ is alkynyl or substituted alkynyl. In certain embodiments, $R_1$ is aryl or substituted aryl. In certain embodiments, $R_1$ is heteroaryl or substituted heteroaryl. In certain embodiments, $R_1$ is cycloalkyl or substituted cycloalkyl. In certain embodiments, $R_1$ is heterocyclyl or substituted heterocyclyl.

In certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments, $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments, $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments, $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments, $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments, $X_1$ is selected from C, N, O and S. In certain embodiments, $X_1$ is C. In certain embodiments, $X_1$ is N. In certain embodiments, $X_1$ is O. In certain embodiments, $X_1$ is S.

In certain embodiments, $X_2$ is selected from C, N, O and S. In certain embodiments, $X_2$ is C. In certain embodiments, $X_2$ is N. In certain embodiments, $X_2$ is O. In certain embodiments, $X_2$ is S.

In certain embodiments, $X_3$ is selected from C, N, O and S. In certain embodiments, $X_3$ is C. In certain embodiments, $X_3$ is N. In certain embodiments, $X_3$ is O. In certain embodiments, $X_3$ is S.

In certain embodiments, $X_4$ is selected from C, N, O and S. In certain embodiments, $X_4$ is C. In certain embodiments, $X_4$ is N. In certain embodiments, $X_4$ is O. In certain embodiments, $X_4$ is S.

Various combinations of $X_1$, $X_2$, $X_3$ and $X_4$ are possible. For example, in certain embodiments, each of $X_1$, $X_2$, $X_3$ and $X_4$ is C. In other instances, three of $X_1$, $X_2$, $X_3$ and $X_4$ are C and one of $X_1$, $X_2$, $X_3$ and $X_4$ is N. In other embodiments, two of $X_1$, $X_2$, $X_3$ and $X_4$ are C and two of $X_1$, $X_2$, $X_3$ and $X_4$ are N. In other embodiments, one of $X_1$, $X_2$, $X_3$ and $X_4$ is C and three of $X_1$, $X_2$, $X_3$ and $X_4$ is are N. Other combinations of C, N, O and S are possible for $X_1$, $X_2$, $X_3$ and $X_4$ as desired.

In certain embodiments, $X_5$ is C.

In certain embodiments, $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments, $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments, $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments, $Y_4$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments, $Y_5$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_5$ is hydrogen. In certain embodiments, $Y_5$ is halogen, such as F, Cl, Br or I. In certain embodiments, $Y_5$ is F. In certain embodiments, $Y_5$ is Cl. In certain embodiments, $Y_5$ is Br. In certain embodiments, $Y_5$ is I. In certain embodiments, $Y_5$ is alkyl or substituted alkyl. In certain embodiments, $Y_5$ is alkenyl or substituted alkenyl. In certain embodiments, $Y_5$ is alkynyl or substituted alkynyl. In certain embodiments, $Y_5$ is alkoxy or substituted alkoxy. In certain embodiments, $Y_5$ is amino or substituted amino. In certain embodiments, $Y_5$ is carboxyl or carboxyl ester. In certain embodiments, $Y_5$ is acyl or acyloxy. In certain embodiments, $Y_5$ is acyl amino or amino acyl. In certain embodiments, $Y_5$ is alkylamide or substituted alkylamide. In certain embodiments, $Y_5$ is sulfonyl. In certain embodiments, $Y_5$ is thioalkoxy or substituted thioalkoxy. In certain embodiments, $Y_5$ is aryl or substituted aryl. In certain embodiments, $Y_5$ is heteroaryl or substituted heteroaryl. In certain embodiments, $Y_5$ is cycloalkyl or substituted cycloalkyl. In certain embodiments, $Y_5$ is heterocyclyl or substituted heterocyclyl.

In certain embodiments, $Q_1$ is a bond to either $X_4$ or $X_5$. In certain embodiments, $Q_1$ is a bond to $X_4$. In certain embodiments, if $Q_1$ is a bond to $X_4$, then $Y_4$ is absent. In certain embodiments, $Q_1$ is a bond to $X_5$. In certain embodiments, if $Q_1$ is a bond to $X_5$, then $Y_5$ is absent.

In certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments, $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments, $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments, one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

In certain embodiments, the conjugate includes at least one modified amino acid residue of formula (II):

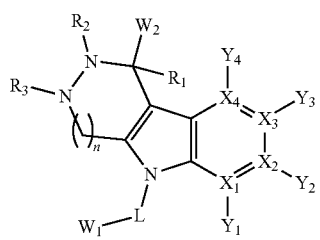

(II)

wherein n is 0 or 1;

$R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$X_1$, $X_2$, $X_3$ and $X_4$ are each independently selected from C, N, O and S;

$Y_1$, $Y_2$, $Y_3$ and $Y_4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

L is an optional linker; and wherein one of $W_1$ and $W_2$ is a polypeptide and the other is a drug or a detectable label.

In certain embodiments, the substituents for formula (II) are the same as for formula (I) described above. For example, in certain embodiments, n is 0 or 1. In certain embodiments, n is 0. In certain embodiments, n is 1.

In certain embodiments, $R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R_1$ is hydrogen. In certain embodiments, $R_1$ is alkyl or substituted alkyl. In certain embodiments, $R_1$ is alkenyl or substituted alkenyl. In certain embodiments, $R_1$ is alkynyl or substituted alkynyl. In certain embodiments, $R_1$ is aryl or substituted aryl. In certain embodiments, $R_1$ is heteroaryl or substituted heteroaryl. In certain embodiments, $R_1$ is cycloalkyl or substituted cycloalkyl. In certain embodiments, $R_1$ is heterocyclyl or substituted heterocyclyl.

In certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments, $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments, $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments, $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments, $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments, $X_1$ is selected from C, N, O and S. In certain embodiments, $X_1$ is C. In certain embodiments, $X_1$ is N. In certain embodiments, $X_1$ is O. In certain embodiments, $X_1$ is S.

In certain embodiments, $X_2$ is selected from C, N, O and S. In certain embodiments, $X_2$ is C. In certain embodiments, $X_2$ is N. In certain embodiments, $X_2$ is O. In certain embodiments, $X_2$ is S.

In certain embodiments, $X_3$ is selected from C, N, O and S. In certain embodiments, $X_3$ is C. In certain embodiments, $X_3$ is N. In certain embodiments, $X_3$ is O. In certain embodiments, $X_3$ is S.

In certain embodiments, $X_4$ is selected from C, N, O and S. In certain embodiments, $X_4$ is C. In certain embodiments, $X_4$ is N. In certain embodiments, $X_4$ is O. In certain embodiments, $X_4$ is S.

Various combinations of $X_1$, $X_2$, $X_3$ and $X_4$ are possible. For example, in certain embodiments, each of $X_1$, $X_2$, $X_3$ and $X_4$ is C. In other instances, three of $X_1$, $X_2$, $X_3$ and $X_4$ are C and one of $X_1$, $X_2$, $X_3$ and $X_4$ is N. In other embodiments, two of $X_1$, $X_2$, $X_3$ and $X_4$ are C and two of $X_1$, $X_2$, $X_3$ and $X_4$ are N. In other embodiments, one of $X_1$, $X_2$, $X_3$ and $X_4$ is C and three of $X_1$, $X_2$, $X_3$ and $X_4$ is are N. Other combinations of C, N, O and S are possible for $X_1$, $X_2$, $X_3$ and $X_4$ as desired.

In certain embodiments, $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments, $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments, $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments, $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments, $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments, $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments, one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

In certain embodiments, the conjugate includes at least one modified amino acid residue of formula (IIa):

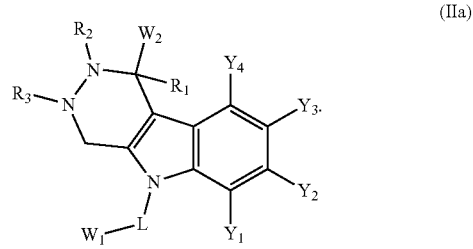

(IIa)

In certain embodiments, the substituents in formula (IIa) are as described above for formula (II). For example, in certain embodiments, $R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R_1$ is hydrogen. In certain embodiments, $R_1$ is alkyl or substituted alkyl. In certain embodiments, $R_1$ is alkenyl or substituted alkenyl. In certain embodiments, $R_1$ is alkynyl or substituted alkynyl. In certain embodiments, $R_1$ is aryl or substituted aryl. In certain embodiments, $R_1$ is heteroaryl or substituted heteroaryl. In certain embodiments, $R_1$ is cycloalkyl or substituted cycloalkyl. In certain embodiments, $R_1$ is heterocyclyl or substituted heterocyclyl.

In certain embodiments of formula (IIa), $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments of formula (IIa), $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments of formula (IIa), $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments of formula (IIa), $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments of formula (IIa), $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments of formula (IIa), $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments of formula (IIa), $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments of formula (IIa), $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments of formula (IIa), $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments of formula (IIa), L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (IIa), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (IIa), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (IIa), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments of formula (IIa), $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments of formula (IIa), one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

In certain embodiments, the conjugate includes at least one modified amino acid residue of formula (IIb):

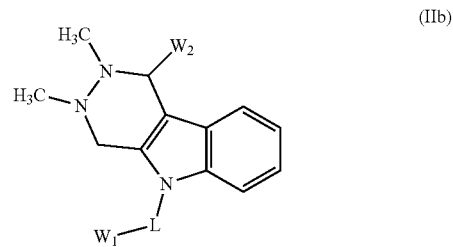

(IIb)

In certain embodiments, the substituents in formula (IIb) are as described above for formula (II). For example, in certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (IIb), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (IIb), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (IIb), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments of formula (IIb), $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments of formula (IIb), one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

In certain embodiments, the conjugate includes at least one modified amino acid residue of formula (III):

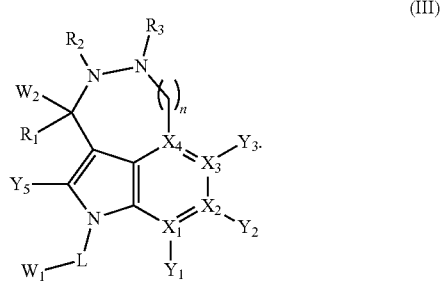

(III)

wherein
n is 0 or 1;
$R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$X_1$, $X_2$, $X_3$ and $X_4$ are each independently selected from C, N, O and S;
$Y_1$, $Y_2$, $Y_3$ and $Y_5$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
L is an optional linker; and
wherein one of $W_1$ and $W_2$ is a polypeptide and the other is a drug or a detectable label.

In certain embodiments, n is 0 or 1. In certain embodiments, n is 0. In certain embodiments, n is 1.

In certain embodiments, $R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R_1$ is hydrogen. In certain embodiments, $R_1$ is alkyl or substituted alkyl. In certain embodiments, $R_1$ is alkenyl or substituted alkenyl. In certain embodiments, $R_1$ is alkynyl or substituted alkynyl. In certain embodiments, $R_1$ is aryl or substituted aryl. In certain embodiments, $R_1$ is heteroaryl or substituted heteroaryl. In certain embodiments, $R_1$ is cycloalkyl or substituted cycloalkyl. In certain embodiments, $R_1$ is heterocyclyl or substituted heterocyclyl.

In certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments, $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments, $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments, $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments, $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments, $X_1$ is selected from C, N, O and S. In certain embodiments, $X_1$ is C. In certain embodiments, $X_1$ is N. In certain embodiments, $X_1$ is O. In certain embodiments, $X_1$ is S.

In certain embodiments, $X_2$ is selected from C, N, O and S. In certain embodiments, $X_2$ is C. In certain embodiments, $X_2$ is N. In certain embodiments, $X_2$ is O. In certain embodiments, $X_2$ is S.

In certain embodiments, $X_3$ is selected from C, N, O and S. In certain embodiments, $X_3$ is C. In certain embodiments, $X_3$ is N. In certain embodiments, $X_3$ is O. In certain embodiments, $X_3$ is S.

In certain embodiments, $X_4$ is selected from C, N, O and S. In certain embodiments, $X_4$ is C. In certain embodiments, $X_4$ is N. In certain embodiments, $X_4$ is O. In certain embodiments, $X_4$ is S.

Various combinations of $X_1$, $X_2$, $X_3$ and $X_4$ are possible. For example, in certain embodiments, each of $X_1$, $X_2$, $X_3$ and $X_4$ is C. In other instances, three of $X_1$, $X_2$, $X_3$ and $X_4$ are C and one of $X_1$, $X_2$, $X_3$ and $X_4$ is N. In other embodiments, two of $X_1$, $X_2$, $X_3$ and $X_4$ are C and two of $X_1$, $X_2$, $X_3$ and $X_4$ are N. In other embodiments, one of $X_1$, $X_2$, $X_3$ and $X_4$ is C and three of $X_1$, $X_2$, $X_3$ and $X_4$ is are N. Other combinations of C, N, O and S are possible for $X_1$, $X_2$, $X_3$ and $X_4$ as desired.

In certain embodiments, $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments, $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments, $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments, $Y_5$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_5$ is hydrogen. In certain embodiments, $Y_5$ is halogen, such as F, Cl, Br or I. In certain embodiments, $Y_5$ is F. In certain embodiments, $Y_5$ is Cl. In certain embodiments, $Y_5$ is Br. In certain embodiments, $Y_5$ is I. In certain embodiments, $Y_5$ is alkyl or substituted alkyl. In certain embodiments, $Y_5$ is alkenyl or substituted alkenyl. In certain embodiments, $Y_5$ is alkynyl or substituted alkynyl. In certain embodiments, $Y_5$ is alkoxy or substituted alkoxy. In certain embodiments, $Y_5$ is amino or substituted amino. In certain embodiments, $Y_5$ is carboxyl or carboxyl ester. In certain embodiments, $Y_5$ is acyl or acyloxy. In certain embodiments, $Y_5$ is acyl amino or amino acyl. In certain embodiments, $Y_5$ is alkylamide or substituted alkylamide. In certain embodiments, $Y_5$ is sulfonyl. In certain embodiments, $Y_5$ is thioalkoxy or substituted thioalkoxy. In certain embodiments, $Y_5$ is aryl or substituted aryl. In certain embodiments, $Y_5$ is heteroaryl or substituted heteroaryl. In certain embodiments, $Y_5$ is cycloalkyl or substituted cycloalkyl. In certain embodiments, $Y_5$ is heterocyclyl or substituted heterocyclyl.

In certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments, $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments, $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments, one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

In certain embodiments, the conjugate includes at least one modified amino acid residue of formula (IIIa):

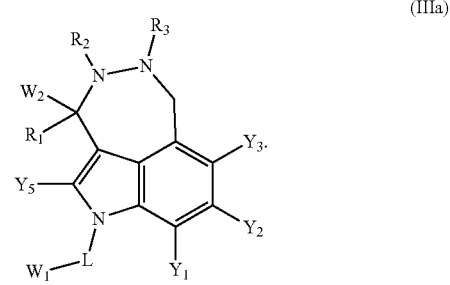

(IIIa)

In certain embodiments, the substituents in formula (IIIa) are as described above for formula (III). For example, in certain embodiments, $R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R_1$ is hydrogen. In certain embodiments, $R_1$ is alkyl or substituted alkyl. In certain embodiments, $R_1$ is alkenyl or substituted alkenyl. In certain embodiments, $R_1$ is alkynyl or substituted alkynyl. In certain embodiments, $R_1$ is aryl or substituted aryl. In certain embodiments, $R_1$ is heteroaryl or substituted heteroaryl. In certain embodiments, $R_1$ is cycloalkyl or substituted cycloalkyl. In certain embodiments, $R_1$ is heterocyclyl or substituted heterocyclyl.

In certain embodiments of formula (IIIa), $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments of formula (IIIa), $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments of formula (IIIa), $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments of formula (IIIa), $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments of formula (IIIa), $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments of formula (IIIa), $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments of formula (IIIa), $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments of formula (IIIa), $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments of formula (IIIa), $Y_5$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_5$ is hydrogen. In certain embodiments, $Y_5$ is halogen, such as F, Cl, Br or I. In certain embodiments, $Y_5$ is F. In certain embodiments, $Y_5$ is Cl. In certain embodiments, $Y_5$ is Br. In certain embodiments, $Y_5$ is I. In certain embodiments, $Y_5$ is alkyl or substituted alkyl. In certain embodiments, $Y_5$ is alkenyl or substituted alkenyl. In certain embodiments, $Y_5$ is alkynyl or substituted alkynyl. In certain embodiments, $Y_5$ is alkoxy or substituted alkoxy. In certain embodiments, $Y_5$ is amino or substituted amino. In certain embodiments, $Y_5$ is carboxyl or carboxyl ester. In certain embodiments, $Y_5$ is acyl or acyloxy. In certain embodiments, $Y_5$ is acyl amino or amino acyl. In certain embodiments, $Y_5$ is alkylamide or substituted alkylamide. In certain embodiments, $Y_5$ is sulfonyl. In certain embodiments, $Y_5$ is thioalkoxy or substituted thioalkoxy. In certain embodiments, $Y_5$ is aryl or substituted aryl. In certain embodiments, $Y_5$ is heteroaryl or substituted heteroaryl. In certain embodiments, $Y_5$ is cycloalkyl or substituted cycloalkyl. In certain embodiments, $Y_5$ is heterocyclyl or substituted heterocyclyl.

In certain embodiments of formula (IIIa), L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (IIIa), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (IIIa), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (IIIa), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments of formula (IIIa), $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments of formula (IIIa), one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

In certain embodiments, the conjugate includes at least one modified amino acid residue of formula (IIIb):

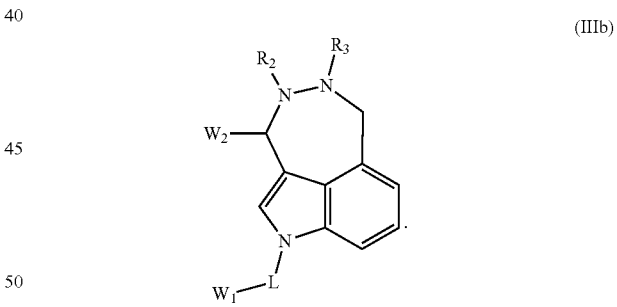

(IIIb)

In certain embodiments, the substituents in formula (IIIb) are as described above for formula (III). For example, in certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (IIIb), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (IIb), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (IIIb), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments of formula (IIIb), $W_2$ is selected from a drug, a detectable label and a polypeptide. In certain embodiments, $W_2$ is a drug. In certain embodiments, $W_2$ is a detectable label. In certain embodiments, $W_2$ is a polypeptide.

In certain embodiments of formula (IIIb), one of $W_1$ and $W_2$ is a polypeptide and the other is a drug or a detectable label. In certain embodiments, $W_1$ is the drug or the detectable label, and $W_2$ is the polypeptide. In certain embodiments, $W_1$ is the polypeptide, and $W_2$ is the drug or the detectable label.

Hydrazinyl-Indole Compounds Useful for Producing Conjugates

The present disclosure provides compounds (e.g., hydrazinyl-indole compounds) useful for producing the conjugates described herein. In certain embodiments, the compound may be a coupling moiety useful for conjugation of a polypeptide and a second moiety. For example, the compound may be bound to the polypeptide and also bound to the second moiety, thus indirectly binding the polypeptide and the second moiety together.

In certain instances, the compound may be a hydrazinyl-indole derivative. Embodiments of the compound include a compound of formula (IV):

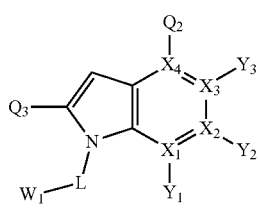

(IV)

wherein
one of $Q_2$ and $Q_3$ is $-(CH_2)_n NR_3 NHR_2$ and the other is $Y_4$;
n is 0 or 1;
$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$X_1$, $X_2$, $X_3$ and $X_4$ are each independently selected from C, N, O and S;
$Y_1$, $Y_2$, $Y_3$ and $Y_4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
L is an optional linker; and
$W_1$ is selected from a drug, a detectable label and a polypeptide.

In certain embodiments, one of $Q_2$ and $Q_3$ is $-(CH_2)_n NR_3 NHR_2$ and the other is $Y_4$. In certain embodiments, $Q_2$ is $-(CH_2)_n NR_3 NHR_2$ and $Q_3$ is $Y_4$. In certain embodiments, $Q_3$ is $-(CH_2)_n NR_3 NHR_2$ and $Q_2$ is $Y_4$.

In certain embodiments, n is 0 or 1. In certain embodiments, n is 0. In certain embodiments, n is 1.

In certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments, $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments, $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments, $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments, $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments, $X_1$ is selected from C, N, O and S. In certain embodiments, $X_1$ is C. In certain embodiments, $X_1$ is N. In certain embodiments, $X_1$ is O. In certain embodiments, $X_1$ is S.

In certain embodiments, $X_2$ is selected from C, N, O and S. In certain embodiments, $X_2$ is C. In certain embodiments, $X_2$ is N. In certain embodiments, $X_2$ is O. In certain embodiments, $X_2$ is S.

In certain embodiments, $X_3$ is selected from C, N, O and S. In certain embodiments, $X_3$ is C. In certain embodiments, $X_3$ is N. In certain embodiments, $X_3$ is O. In certain embodiments, $X_3$ is S.

In certain embodiments, $X_4$ is selected from C, N, O and S. In certain embodiments, $X_4$ is C. In certain embodiments, $X_4$ is N. In certain embodiments, $X_4$ is O. In certain embodiments, $X_4$ is S.

Various combinations of $X_1$, $X_2$, $X_3$ and $X_4$ are possible. For example, in certain embodiments, each of $X_1$, $X_2$, $X_3$ and $X_4$ is C. In other instances, three of $X_1$, $X_2$, $X_3$ and $X_4$ are C and one of $X_1$, $X_2$, $X_3$ and $X_4$ is N. In other embodiments, two of $X_1$, $X_2$, $X_3$ and $X_4$ are C and two of $X_1$, $X_2$, $X_3$ and $X_4$ are N. In other embodiments, one of $X_1$, $X_2$, $X_3$ and $X_4$ is C and three of $X_1$, $X_2$, $X_3$ and $X_4$ is are N. Other combinations of C, N, O and S are possible for $X_1$, $X_2$, $X_3$ and $X_4$ as desired.

In certain embodiments, $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments, $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments, $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments, $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments, $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

Embodiments of the compound include a compound of formula (V):

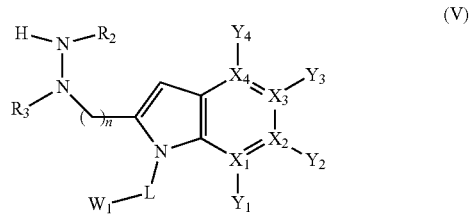

(V)

wherein
n is 0 or 1;
$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$X_1$, $X_2$, $X_3$ and $X_4$ are each independently selected from C, N, O and S;
$Y_1$, $Y_2$, $Y_3$ and $Y_4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
L is an optional linker; and
$W_1$ is selected from a drug, a detectable label and a polypeptide.

In certain embodiments, the substituents for formula (V) are the same as for formula (IV) described above. For example, in certain embodiments, n is 0 or 1. In certain embodiments, n is 0. In certain embodiments, n is 1.

In certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments, $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments, $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments, $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments, $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments, $X_1$ is selected from C, N, O and S. In certain embodiments, $X_1$ is C. In certain embodiments, $X_1$ is N. In certain embodiments, $X_1$ is O. In certain embodiments, $X_1$ is S.

In certain embodiments, $X_2$ is selected from C, N, O and S. In certain embodiments, $X_2$ is C. In certain embodiments, $X_2$ is N. In certain embodiments, $X_2$ is O. In certain embodiments, $X_2$ is S.

In certain embodiments, $X_3$ is selected from C, N, O and S. In certain embodiments, $X_3$ is C. In certain embodiments, $X_3$ is N. In certain embodiments, $X_3$ is O. In certain embodiments, $X_3$ is S.

In certain embodiments, $X_4$ is selected from C, N, O and S. In certain embodiments, $X_4$ is C. In certain embodiments, $X_4$ is N. In certain embodiments, $X_4$ is O. In certain embodiments, $X_4$ is S.

Various combinations of $X_1$, $X_2$, $X_3$ and $X_4$ are possible. For example, in certain embodiments, each of $X_1$, $X_2$, $X_3$ and $X_4$ is C. In other instances, three of $X_1$, $X_2$, $X_3$ and $X_4$ are C and one of $X_1$, $X_2$, $X_3$ and $X_4$ is N. In other embodiments, two of $X_1$, $X_2$, $X_3$ and $X_4$ are C and two of $X_1$, $X_2$, $X_3$ and $X_4$ are N. In other embodiments, one of $X_1$, $X_2$, $X_3$ and $X_4$ is C and three of $X_1$, $X_2$, $X_3$ and $X_4$ is are N. Other combinations of C, N, O and S are possible for $X_1$, $X_2$, $X_3$ and $X_4$ as desired.

In certain embodiments, $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments, $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments, $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments, $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments, $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

Embodiments of the compound include a compound of formula (Va):

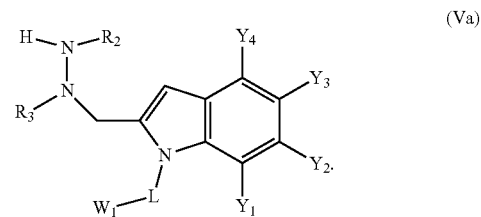

(Va)

In certain embodiments, the substituents in formula (Va) are as described above for formula (V). For example, in certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments of formula (Va), $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments of formula (Va), $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments of formula (Va), $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments of formula (Va), $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments of formula (Va), $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments of formula (Va), $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments of formula (Va), $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments of formula (Va), $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments of formula (Va), L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (Va), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (Va), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (Va), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

Embodiments of the compound include a compound of formula (Vb):

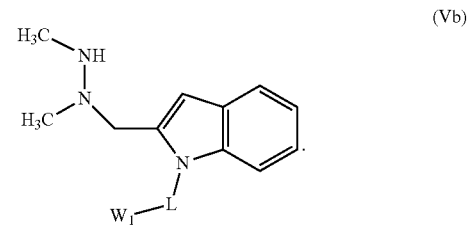

In certain embodiments, the substituents in formula (Vb) are as described above for formula (V). For example, in certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (Vb), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (Vb), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (Vb), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

In certain embodiments, the compound may be a hydrazinyl-indole derivative of formula (VI):

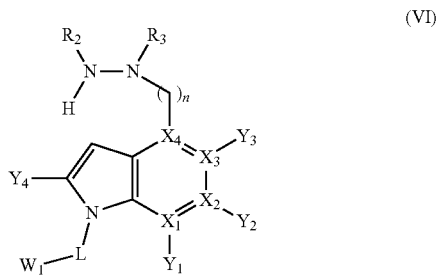

(VI)

wherein
n is 0 or 1;
$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$X_1$, $X_2$, $X_3$ and $X_4$ are each independently selected from C, N, O and S;
$Y_1$, $Y_2$, $Y_3$ and $Y_4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
L is an optional linker; and
$W_1$ is selected from a drug, a detectable label and a polypeptide.

In certain embodiments, the substituents in formula (VI) are as described above for formula (IV). For example, in certain embodiments, n is 0 or 1. In certain embodiments, n is 0. In certain embodiments, n is 1.

In certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments, $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments, $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments, $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments, $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments, $X_1$ is selected from C, N, O and S. In certain embodiments, $X_1$ is C. In certain embodiments, $X_1$ is N. In certain embodiments, $X_1$ is O. In certain embodiments, $X_1$ is S.

In certain embodiments, $X_2$ is selected from C, N, O and S. In certain embodiments, $X_2$ is C. In certain embodiments, $X_2$ is N. In certain embodiments, $X_2$ is O. In certain embodiments, $X_2$ is S.

In certain embodiments, $X_3$ is selected from C, N, O and S. In certain embodiments, $X_3$ is C. In certain embodiments, $X_3$ is N. In certain embodiments, $X_3$ is O. In certain embodiments, $X_3$ is S.

In certain embodiments, $X_4$ is selected from C, N, O and S. In certain embodiments, $X_4$ is C. In certain embodiments, $X_4$ is N. In certain embodiments, $X_4$ is O. In certain embodiments, $X_4$ is S.

Various combinations of $X_1$, $X_2$, $X_3$ and $X_4$ are possible. For example, in certain embodiments, each of $X_1$, $X_2$, $X_3$ and $X_4$ is C. In other instances, three of $X_1$, $X_2$, $X_3$ and $X_4$ are C and one of $X_1$, $X_2$, $X_3$ and $X_4$ is N. In other embodiments, two of $X_1$, $X_2$, $X_3$ and $X_4$ are C and two of $X_1$, $X_2$, $X_3$ and $X_4$ are N. In other embodiments, one of $X_1$, $X_2$, $X_3$ and $X_4$ is C and three of $X_1$, $X_2$, $X_3$ and $X_4$ is are N. Other combinations of C, N, O and S are possible for $X_1$, $X_2$, $X_3$ and $X_4$ as desired.

In certain embodiments, $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments, $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments, $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments, $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments, $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

Embodiments of the compound include a compound of formula (VIa):

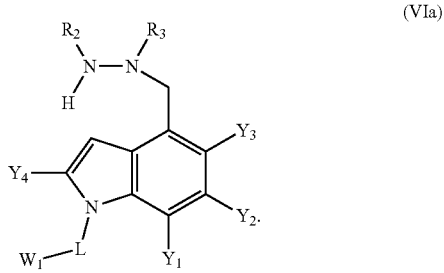

(VIa)

In certain embodiments, the substituents in formula (VIa) are as described above for formula (VI). For example, in certain embodiments, $R_2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_2$ is hydrogen. In certain embodiments, $R_2$ is alkyl or substituted alkyl. In certain embodiments, $R_2$ is alkenyl or substituted alkenyl. In certain embodiments, $R_2$ is alkynyl or substituted alkynyl. In certain embodiments, $R_2$ is alkoxy or substituted alkoxy. In certain embodiments, $R_2$ is amino or substituted amino. In certain embodiments, $R_2$ is carboxyl or carboxyl ester. In certain embodiments, $R_2$ is acyl or acyloxy. In certain embodiments, $R_2$ is acyl amino or amino acyl. In certain embodiments, $R_2$ is alkylamide or substituted alkylamide. In certain embodiments, $R_2$ is sulfonyl. In certain embodiments, $R_2$ is thioalkoxy or substituted thioalkoxy. In certain embodiments, $R_2$ is aryl or substituted aryl. In certain embodiments, $R_2$ is heteroaryl or substituted heteroaryl. In certain embodiments, $R_2$ is cycloalkyl or substituted cycloalkyl. In certain embodiments, $R_2$ is heterocyclyl or substituted heterocyclyl.

In certain embodiments of formula (VIa), $R_2$ is alkyl or substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ is methyl, ethyl, n-propyl, iso-propyl, n-butyl, sec-butyl, isobutyl, t-butyl, or the like. In certain cases, $R_2$ is methyl.

In certain embodiments of formula (VIa), $R_3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R_3$ is hydrogen. In certain embodiments, $R_3$ is alkyl or substituted alkyl. In certain embodiments, $R_3$ is alkenyl or substituted alkenyl. In certain embodiments, $R_3$ is alkynyl or substituted alkynyl. In certain embodiments, $R_3$ is alkoxy or substituted alkoxy. In certain embodiments, $R_3$ is amino or substituted amino. In certain embodiments, $R_3$ is carboxyl or carboxyl ester. In certain embodiments, $R_3$ is acyl or acyloxy. In certain embodiments, $R_3$ is acyl amino or amino acyl. In certain embodiments, $R_3$ is alkylamide or substituted alkylamide. In certain embodiments, $R_3$ is sulfonyl. In certain embodiments, $R_3$ is thioalkoxy or substituted thioalkoxy. In certain embodiments, $R_3$ is aryl or substituted aryl. In certain embodiments, $R_3$ is heteroaryl or substituted heteroaryl. In certain embodiments, $R_3$ is cycloalkyl or substituted cycloalkyl. In certain embodiments, $R_3$ is heterocyclyl or substituted heterocyclyl.

In certain embodiments of formula (VIa), $R_3$ is alkyl or substituted alkyl. For example, $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_3$ is methyl, ethyl, n-propyl, iso-propyl, n-butyl, sec-butyl, isobutyl, t-butyl, or the like. In certain cases, $R_3$ is methyl.

In certain embodiments of formula (VIa), $R_2$ and $R_3$ are each independently selected from alkyl and substituted alkyl. For example, $R_2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R_3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R_2$ and $R_3$ are each independently selected from methyl, ethyl, n-propyl, iso-propyl, n-butyl, sec-butyl, isobutyl, t-butyl, or the like. In certain cases, $R_2$ and $R_3$ are each methyl.

In certain embodiments of formula (VIa), $Y_1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_1$ is hydrogen. In certain embodiments, $Y_1$ is halogen, such as F, Cl, Br or I. In certain embodiments, $Y_1$ is F. In certain embodiments, $Y_1$ is Cl. In certain embodiments, $Y_1$ is Br. In certain embodiments, $Y_1$ is I. In certain embodiments, $Y_1$ is alkyl or substituted alkyl. In certain embodiments, $Y_1$ is alkenyl or substituted alkenyl. In certain embodiments, $Y_1$ is alkynyl or substituted alkynyl. In certain embodiments, $Y_1$ is alkoxy or substituted alkoxy. In certain embodiments, $Y_1$ is amino or substituted amino. In certain embodiments, $Y_1$ is carboxyl or carboxyl ester. In certain embodiments, $Y_1$ is acyl or acyloxy. In certain embodiments, $Y_1$ is acyl amino or amino acyl. In certain embodiments, $Y_1$ is alkylamide or substituted alkylamide. In certain embodiments, $Y_1$ is sulfonyl. In certain embodiments, $Y_1$ is thioalkoxy or substituted thioalkoxy. In certain embodiments, $Y_1$ is aryl or substituted aryl. In certain embodiments, $Y_1$ is heteroaryl or substituted heteroaryl. In certain embodiments, $Y_1$ is cycloalkyl or substituted cycloalkyl. In certain embodiments, $Y_1$ is heterocyclyl or substituted heterocyclyl.

In certain embodiments of formula (VIa), $Y_2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_2$ is hydrogen. In certain embodiments, $Y_2$ is halogen, such as F, Cl, Br or I. In certain embodiments, $Y_2$ is F. In certain embodiments, $Y_2$ is Cl. In certain embodiments, $Y_2$ is Br. In certain embodiments, $Y_2$ is I. In certain embodiments, $Y_2$ is alkyl or substituted alkyl. In certain embodiments, $Y_2$ is alkenyl or substituted alkenyl. In certain embodiments, $Y_2$ is alkynyl or substituted alkynyl. In certain embodiments, $Y_2$ is alkoxy or substituted alkoxy. In certain embodiments, $Y_2$ is amino or substituted amino. In certain embodiments, $Y_2$ is carboxyl or carboxyl ester. In certain embodiments, $Y_2$ is acyl or acyloxy. In certain embodiments, $Y_2$ is acyl amino or amino acyl. In certain embodiments, $Y_2$ is alkylamide or substituted alkylamide. In certain embodiments, $Y_2$ is sulfonyl. In certain embodiments, $Y_2$ is thioalkoxy or substituted thioalkoxy. In certain embodiments, $Y_2$ is aryl or substituted aryl. In certain embodiments, $Y_2$ is heteroaryl or substituted heteroaryl. In certain embodiments, $Y_2$ is cycloalkyl or substituted cycloalkyl. In certain embodiments, $Y_2$ is heterocyclyl or substituted heterocyclyl.

In certain embodiments of formula (VIa), $Y_3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_3$ is hydrogen. In certain embodiments, $Y_3$ is halogen, such as F, Cl, Br or I. In certain embodiments, $Y_3$ is F. In certain embodiments, $Y_3$ is Cl. In certain embodiments, $Y_3$ is Br. In certain embodiments, $Y_3$ is I. In certain embodiments, $Y_3$ is alkyl or substituted alkyl. In certain embodiments, $Y_3$ is alkenyl or substituted alkenyl. In certain embodiments, $Y_3$ is alkynyl or substituted alkynyl. In certain embodiments, $Y_3$ is alkoxy or substituted alkoxy. In certain embodiments, $Y_3$ is amino or substituted amino. In certain embodiments, $Y_3$ is carboxyl or carboxyl ester. In certain embodiments, $Y_3$ is acyl or acyloxy. In certain embodiments, $Y_3$ is acyl amino or amino acyl. In certain embodiments, $Y_3$ is alkylamide or substituted alkylamide. In certain embodiments, $Y_3$ is sulfonyl. In certain embodiments, $Y_3$ is thioalkoxy or substituted thioalkoxy. In certain embodiments, $Y_3$ is aryl or substituted aryl. In certain embodiments, $Y_3$ is heteroaryl or substituted heteroaryl. In certain embodiments, $Y_3$ is cycloalkyl or substituted cycloalkyl. In certain embodiments, $Y_3$ is heterocyclyl or substituted heterocyclyl.

In certain embodiments of formula (VIa), $Y_4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y_4$ is hydrogen. In certain embodiments, $Y_4$ is halogen, such as F, Cl, Br or I. In certain embodiments, $Y_4$ is F. In certain embodiments, $Y_4$ is Cl. In certain embodiments, $Y_4$ is Br. In certain embodiments, $Y_4$ is I. In certain embodiments, $Y_4$ is alkyl or substituted alkyl. In certain embodiments, $Y_4$ is alkenyl or substituted alkenyl. In certain embodiments, $Y_4$ is alkynyl or substituted alkynyl. In certain embodiments, $Y_4$ is alkoxy or substituted alkoxy. In certain embodiments, $Y_4$ is amino or substituted amino. In certain embodiments, $Y_4$ is carboxyl or carboxyl ester. In certain embodiments, $Y_4$ is acyl or acyloxy. In certain embodiments, $Y_4$ is acyl amino or amino acyl. In certain embodiments, $Y_4$ is alkylamide or substituted alkylamide. In certain embodiments, $Y_4$ is sulfonyl. In certain embodiments, $Y_4$ is thioalkoxy or substituted thioalkoxy. In certain embodiments, $Y_4$ is aryl or substituted aryl. In certain embodiments, $Y_4$ is heteroaryl or substituted heteroaryl. In certain embodiments, $Y_4$ is cycloalkyl or substituted cycloalkyl. In certain embodiments, $Y_4$ is heterocyclyl or substituted heterocyclyl.

In certain embodiments of formula (VIa), L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (VIa), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (VIa), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (VIa), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

Embodiments of the compound include a compound of formula (VIb):

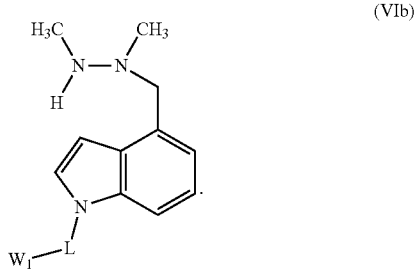

(VIb)

In certain embodiments, the substituents in formula (VIb) are as described above for formula (VI). For example, in certain embodiments, L is an optional linker. In certain embodiments, L is not present, and thus the nitrogen of the indole ring is directly bonded to $W_1$. In certain embodiments, L is present, and thus the nitrogen of the indole ring is indirectly bonded to $W_1$ through the linker L.

In certain embodiments of formula (VIb), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments of formula (VIb), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain embodiments of formula (VIb), $W_1$ is selected from a drug, a detectable label and a polypeptide. In certain embodiments, $W_1$ is a drug. In certain embodiments, $W_1$ is a detectable label. In certain embodiments, $W_1$ is a polypeptide.

Target Polypeptides

Any of a wide variety of polypeptides can be modified to be conjugated to a second moiety as described above. Polypeptides suitable for modification include both proteins having a naturally-occurring amino acid sequence, fragments of naturally-occurring polypeptides, and non-naturally occurring polypeptides and fragments thereof.

The following are examples of classes and types of polypeptides which are of interest for modification using the compounds and methods described herein to produce the polypeptide conjugates described herein.

Therapeutic Polypeptides

In certain embodiments, the methods of producing a conjugate are applied to modification of polypeptides that may provide for a therapeutic benefit, such as those polypeptides for which attachment to a moiety can provide for one or more of, for example, an increase in serum half-life, a decrease in an adverse immune response, additional or alternate biological activity or functionality, and the like, or other benefit or reduction of an adverse side effect. Where the therapeutic polypeptide is an antigen for a vaccine, modification can provide for an enhanced immunogenicity of the polypeptide.

Examples of classes of therapeutic proteins include those that are cytokines, chemokines, growth factors, hormones, antibodies, and antigens. Further examples include, but are not limited to, the following: erythropoietin (EPO, e.g., native EPO or synthetic EPO (see, e.g., US 2003/0191291), such as, but not limited to, e.g., PROCRIT®, EPREX®, or EPOGEN® (epoetin-α), ARANESP® (darbepoietin-α), NEORECORMON®, EPOGIN® (epoetin-β), and the like); a growth hormone (e.g., a somatotropin, e.g., GENOTROPIN®, NUTROPIN®, NORDITROPIN®, SAIZEN®, SEROSTIM®, HUMATROPE®, etc.); human growth hormone (hGH); bovine growth hormone (bGH); follicle stimulating hormone (FSH); interferon (e.g., IFN-γ, IFN-α, IFN-β, IFN-ω; IFN-τ, consensus interferon, and the like); insulin (e.g., Novolin, Humulin, Humalog, Lantus, Ultralente, etc.), insulin-like growth factor (e.g., IGF-I, IGF-II); blood factors (e.g., Factor X, tissue plasminogen activator (TPA), and the like, such as, but not limited to, e.g., ACTIVASE® (alteplase) tissue plasminogen activator, NOVOSEVEN® (recombinant human factor VIIa), Factor VIIa, Factor VIII (e.g., KOGENATE®), Factor IX, 3-globin, hemoglobin, and the like); colony stimulating factors (e.g., granulocyte-CSF (G-CSF, e.g., NEUPOGEN® (filgrastim)), macrophage-CSF (M-CSF), granulocyte-macrophage-CSF (GM-CSF), Neulasta (pegfilgrastim), granulocyte-monocyte colony stimulating factor, megakaryocyte colony stimulating factor, and the like), transforming growth factors (e.g., TGF-beta, TGF-alpha); interleukins (e.g., IL-1, IL-2 (e.g., Proleukin®), IL-3, IL-4, IL-5, IL-6, IL-7, IL-8, IL-9, IL-12, and the like); a growth factor (e.g., epidermal growth factor (EGF), platelet-derived growth factor (PDGF, e.g., REGRANEX® (beclapermin)), fibroblast growth factors (FGFs, e.g., aFGF, bFGF, such as FIBLAST® (trafermin)), glial cell line-derived growth factor (GDNF), nerve growth factor (NGF), stem cell factor (e.g., STEMGEN® (ancestim)), keratinocyte growth factor, a hepatocyte growth factor, and the like); a soluble receptor (e.g., a TNF-α-binding soluble receptor such as ENBREL® (etanercept), a soluble VEGF receptor, a soluble interleukin receptor, a soluble γ/δ T cell receptor, and the like); an enzyme (e.g., α-glucosidase, CERAZYME® (imiglucarase, β-glucocerebrosidase, CEREDASE® (alglucerase); an enzyme activator (e.g., tissue plasminogen activator); a chemokine (e.g., IP-10, Mig, Groα/IL-8, regulated and normal T cell expressed and secreted (RANTES), MIP-1α, MIP-1β, MCP-1, PF-4, and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); and the like. It will be readily appreciated that native forms of the above therapeutic proteins are also of interest as target polypeptides in the present disclosure.

Further examples include antibodies, e.g., polyclonal antibodies, monoclonal antibodies, humanized antibodies, antigen-binding fragments (e.g., F(ab)', Fab, Fv), single chain antibodies, and the like (e.g., RITUXAN® (rituximab); REMICADE® (infliximab); HERCEPTIN® (trastuzumab); HUMIRA™ (adalimumab); XOLAIR® (omalizumab); BEXXAR® (tositumomab); RAPTIVA™ (efalizumab); ERBITUX™ (cetuximab); and the like. In some instances, antibodies include antibodies that specifically bind to a tumor antigen, an immune cell antigen (e.g., CD4, CD8, and the like), an antigen of a microorganism, particularly a pathogenic microorganism (e.g., a bacterial, viral, fungal, or parasitic antigen), and the like.

In some instances, the methods, conjugates and compounds described herein can be applied to provide for a moiety (e.g., a water-soluble polymer) at a native or engineered site of glycosylation, such as found in hyperglycosylated forms of a therapeutic protein.

The biological activity of a modified target polypeptide can be assayed according to methods known in the art. Modified polypeptides that retain at least one desired pharmacologic activity of the corresponding parent protein are of interest.

Immunogenic Compositions

The methods, conjugates and compounds disclosed herein also find application in production of components of immunogenic compositions (e.g., therapeutic vaccines). For example, the compounds can be used to facilitate attachment of moieties that increase serum half-life of a polypeptide antigen, that increase immunogenicity of the polypeptide, or that link a non-amino acid antigen to a polypeptide carrier. In this regard, the compounds can be used to facilitate modification of microbial antigens (e.g., a bacterial, viral, fungal, or parasitic antigen), tumor antigens, and other antigens which are of interest for administration to a subject to elicit an immune response in the subject. Also of interest is modification of antigens that are useful in eliciting antibodies which can be useful as research tools.

Further examples of polypeptides of interest for modification using the compounds disclosed herein include those that are of interest for detection or functional monitoring in an assay (e.g., as a research tool, in a drug screening assay, and the like). Examples of polypeptides of this type include receptors (e.g., G-protein coupled receptors (GPCRs, including orphan GPCRs)), receptor ligands (including naturally-occurring and synthetic), protein channels (e.g., ion channels (e.g., potassium channels, calcium channels, sodium channels, and the like), and other polypeptides. In some embodiments, modification of cell surface-associated polypeptides, such as transmembrane polypeptides) is of interest, for example where such modification is accomplished while the polypeptide is present in a membrane. Methods for modification of a polypeptide under physiological conditions are described further below.

Methods of Polypeptide Production

In general, the polypeptides described herein may be expressed in prokaryotes or eukaryotes in accordance with conventional ways, depending upon the purpose for expression. Thus, the present invention further provides a host cell, e.g., a genetically modified host cell that comprises a nucleic acid encoding a polypeptide.

Host cells for production (including large scale production) of an unconjugated or modified polypeptide suitable to form a conjugate as described herein can be selected from any of a variety of available host cells. Examples of host cells include those of a prokaryotic or eukaryotic unicellular organism, such as bacteria (e.g., *Escherichia coli* strains, *Bacillus* spp. (e.g., *B. subtilis*), and the like) yeast or fungi (e.g., *S. cerevisiae, Pichia* spp., and the like), and other such host cells can be used. Examples of host cells originally derived from a higher organism such as insects, vertebrates, including mammals, (e.g., CHO, HEK, and the like), may be used as the expression host cells.

Suitable mammalian cell lines include, but are not limited to, HeLa cells (e.g., American Type Culture Collection (ATCC) No. CCL-2), CHO cells (e.g., ATCC Nos. CRL9618 and CRL9096), CHO DG44 cells (Urlaub (1983) Cell 33:405), CHO-K1 cells (ATCC CCL-61), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Specific expression systems of interest include bacterial, yeast, insect cell and mammalian cell derived expression systems.

The expressed polypeptide can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the desired polypeptide, and purified using high performance liquid chromatography (HPLC), exclusion chromatography, gel electrophoresis, affinity chromatography, and the like.

Methods for Modification of a Polypeptide

In certain embodiments, the polypeptide may be conjugated to a moiety of interest without first modifying the polypeptide. For instance, the polypeptide may include one or more reactive groups suitable for conjugation to the moiety of interest (e.g., a moiety comprising a coupling moiety, such as a hydrazinyl-indole compound or hydrazinyl-indole derivative as described herein). In other embodiments, the polypeptide may be modified before conjugation to the moiety of interest. Modification of the polypeptide may produce a modified polypeptide that contains one or more reactive groups suitable for conjugation to the moiety of interest.

In some cases, the polypeptide may be modified at one or more amino acid residues to provide one or more reactive groups suitable for conjugation to the moiety of interest (e.g., a moiety comprising a coupling moiety, such as a hydrazinyl-indole compound or hydrazinyl-indole derivative as described herein). For example, carbonyls introduced into a polypeptide can be selectively reacted with α-nucleophiles, such as aminooxy- and hydrazide-bearing compounds. Chemistries selective for carbonyl functional groups on a protein with enhanced kinetics, site selectivity and conjugate stability may result in improved bioconjugates and provide access to new products and therapeutic targets as disclosed herein.

In certain embodiments, the polypeptide may be modified to include an aldehyde tag. By "aldehyde tag" or "ald-tag" is meant an amino acid sequence that contains an amino acid sequence derived from a sulfatase motif which is capable of being converted, or which has been converted, by action of a formylglycine generating enzyme (FGE) to contain a 2-formylglycine residue (referred to herein as "fGly"). The fGly residue generated by an FGE is often referred to in the literature as a "formylglycine". Stated differently, the term "aldehyde tag" is used herein to refer to an amino acid sequence comprising an "unconverted" sulfatase motif (i.e., a sulfatase motif in which the cysteine or serine residues has not been converted to fGly by an FGE, but is capable of being converted, such as a sulfatase motif with the sequence: L(C/S)TPSR) as well as to an amino acid sequence comprising a "converted" sulfatase motif (i.e., a sulfatase motif in which the cysteine or the serine residue has been converted to fGly by action of an FGE, e.g., L(fGly)TPSR). By "conversion" as used in the context of action of a formylglycine generating enzyme (FGE) on a sulfatase motif refers to biochemical modification of a cysteine or serine residue in a sulfatase motif to a formylglycine (fGly) residue (e.g., Cys to fGly, or Ser to fGly). Additional aspects of aldehyde tags and uses thereof in site-specific protein modification are described in U.S. Pat. No. 7,985,783, the disclosure of which is incorporated herein by reference.

Conversion of a polypeptide to include fGly can be accomplished by cell-based (in vivo) or cell-free methods (in vitro). Similarly, modification of a polypeptide to produce a polypeptide suitable for conjugation (e.g., modification to produce a polypeptide containing a reactive group suitable for conjugation) can be accomplished by cell-based (in vivo) or cell-free methods (in vitro).

Alternatively, isolated, unmodified polypeptides can be isolated following recombinant production in a host cell lacking a suitable enzyme or by synthetic production. The isolated polypeptide may then be contacted with a suitable enzyme under conditions to provide for the desired modification of the polypeptide to include fGly. The polypeptide can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable enzyme. The modified polypeptide can then be refolded under suitable conditions.

In some cases, the modified polypeptide containing the fGly residue may be conjugated to the moiety of interest by reaction of the fGly with a compound as described herein (e.g., a compound containing a coupling moiety, such as a hydrazinyl-indole or hydrazinyl-indole derivative as described herein). For example, an fGly-containing polypeptide may be isolated from a production source (e.g., recombinant host cell production, synthetic production), and contacted with a reactive partner-containing drug or other moiety (e.g., detectable label) under conditions suitable to provide for conjugation of the drug or other moiety to the polypeptide. For example, the reactive partner-containing drug or other moiety may include a reactive moiety (e.g., a hydrazinyl-indole compound or hydrazinyl-indole derivative as described herein). The hydrazinyl-indole-containing drug or other moiety may be reacted with the polypeptide to produce a polypeptide conjugate as described herein. For example, FIG. 1, panels A and B, show schematic drawings of polypeptide conjugates according to embodiments of the present disclosure. FIG. 1, panel A, shows a reaction scheme for the production of a polypeptide conjugate that includes a hydrazinyl-indole coupling moiety. In FIG. 1, panel A, a polypeptide (indicated by the shaded sphere in the figure) that includes an fGly is reacted with a hydrazinyl-indole coupling moiety (e.g., a hydrazinyl-indole compound or hydrazinyl-indole derivative) to produce a polypeptide conjugate that includes the coupling moiety. As shown in FIG. 1, panel A, the hydrazine of the hydrazinyl-indole coupling moiety undergoes an intramolecular cyclization to form a partially unsaturated pyrazole or pyridazine ring depending on whether n is 0 or 1, respectively. In FIG. 1, panel A, the shaded sphere may represent a polypeptide and $R_4$ may be a drug or a detectable label, however in other embodiments, the shaded sphere may represent a drug or a detectable label and $R_4$ may be a polypeptide. FIG. 1, panel B, shows a reaction scheme for the production of a polypeptide conjugate that includes a different hydrazinyl-indole coupling moiety. In FIG. 1, panel B, a polypeptide that includes an fGly is reacted with the hydrazinyl-indole coupling moiety to produce a polypeptide conjugate that includes the coupling moiety. As shown in FIG. 1, panel B, the hydrazine of the hydrazinyl-indole coupling moiety undergoes an intramolecular cyclization to form a partially unsaturated pyridazine or 1,2-diazepine ring depending on whether n is 0 or 1, respectively. In FIG. 1, panel B, the shaded sphere may represent a polypeptide and $R_4$ may be a drug or a detectable label, however in other embodiments, the shaded sphere may represent a drug or a detectable label and $R_4$ may be a polypeptide.

Polypeptide Conjugates

The polypeptides can be subjected to conjugation to provide for attachment of a wide variety of moieties. Examples of moieties of interest include, but are not limited to, a drug, a detectable label, a small molecule, a water-soluble polymer, a peptide, and the like. Thus, the present disclosure provides a polypeptide conjugate as described above.

The moiety of interest is provided as a component of a reactive partner for reaction with a residue of a polypeptide. In certain embodiments, the methods of polypeptide conjugation are compatible with reaction conditions suitable for the polypeptide. For example, the reaction conditions may include a reaction mixture that includes water. In some cases, the reaction mixture may have a pH compatible with the polypeptide, such as, but not limited to, a pH of 4 to 11, or a pH of 5 to 10, or a pH of 6 to 9, or a pH of 6 to 8. In certain instances, the reaction mixture has a pH of 7. In some embodiments, the reaction conditions are performed at a temperature compatible with the polypeptide. For example, the reaction conditions may be at a temperature of 20° C. to 45° C., such as 25° C. to 40° C., or 30° C. to 40° C., or 35° C. to 40° C. In some cases, the reaction conditions are at room temperature (e.g., 25° C.). In some instances, the reaction conditions are at a temperature of 37° C.

Provided the present disclosure, the ordinarily skilled artisan can readily adapt any of a variety of moieties to provide a reactive partner for conjugation to a polypeptide as contemplated herein. The ordinarily skilled artisan will appreciate that factors such as pH and steric hindrance (i.e., the accessibility of the modified amino acid residue to reaction with a reactive partner of interest) are of importance. Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

In certain embodiments, the present disclosure provides a polypeptide conjugate, where the polypeptide is an antibody. As such, embodiments include an antibody conjugated to a moiety of interest, where an antibody conjugated to a moiety of interest is referred to as an "antibody conjugate." An Ig polypeptide generally includes at least an Ig heavy chain constant region or an Ig light chain constant region, and can further include an Ig variable region (e.g., a $V_L$ region and/or a $V_H$ region). Ig heavy chain constant regions include Ig constant regions of any heavy chain isotype, non-naturally occurring Ig heavy chain constant regions (including consensus Ig heavy chain constant regions). An Ig constant region can be modified to be conjugated to a moiety of interest, where the moiety of interest is present in or adjacent a solvent-accessible loop region of the Ig constant region.

In some cases, an antibody conjugate of the present disclosure can include: 1) Ig heavy chain constant region conjugated to one or more moieties of interest, and an Ig light chain constant region conjugated to one or more moieties of interest; 2) an Ig heavy chain constant region conjugated to one or more moieties of interest, and an Ig light chain constant region that is not conjugated to a moiety of interest; or 3) an Ig heavy chain constant region that is not conjugated to a moiety of interest, and an Ig light chain constant region conjugated to one or more moieties of interest. A subject antibody conjugate can also include variable VH and/or VL domains. As described above, the one or more moieties of interest may be conjugated to the Ig heavy chain constant region or the Ig light chain constant region at a single amino acid residue (e.g., one or two moieties of interest conjugated to a single amino acid residue), or conjugated to the Ig heavy chain constant region and/or the Ig light chain constant region at two or more different amino acid residues.

An antibody conjugate of the present disclosure can include, as the conjugated moiety, any of a variety of compounds, as described herein, e.g., a drug (e.g., a peptide drug, a small molecule drug, and the like), a water-soluble polymer, a detectable label, a synthetic peptide, etc.

An antibody conjugate can have any of a variety of antigen-binding specificities, as described above, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, an antibody conjugate can bind an antigen, as noted above, where the antigen is present on the surface of the cell. An antibody conjugate of the present disclosure can bind antigen with a suitable binding affinity, e.g., from $5 \times 10^{-6}$ M to $10^{-7}$ M, from $10^{-7}$ M to $5 \times 10^{-7}$ M, from $5 \times 10^{-7}$ M to $10^{-8}$ M, from $10^{-8}$ M to $5 \times 10^{-8}$ M, from $5 \times 10^{-8}$ M to $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the conjugated moiety can be a drug (e.g., a small molecule drug, a peptide drug, etc.). For example, a subject antibody conjugate can be specific for CD19, where the conjugated moiety is a drug (e.g., a small molecule drug, a peptide drug, etc.). As another example, a subject antibody conjugate can be specific for CD22, where the conjugated moiety can be a drug (e.g., a small molecule drug, a peptide drug, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the conjugated moiety can be a viral fusion inhibitor. For example, a subject antibody conjugate can bind CD4, and the conjugated moiety can be a viral fusion inhibitor. As another example, a subject antibody conjugate can bind gp120, and the conjugated moiety can be a viral fusion inhibitor.

Embodiments of the present disclosure also include polypeptide conjugates where the polypeptide is a carrier protein. For example, carrier proteins can be covalently and site-specifically bound to drug to provide a drug-containing scaffold. A carrier protein can be site-specifically conjugated to a covalently bound molecule of interest, such as a drug (e.g., a peptide, a small molecule drug, and the like), detectable label, etc. In certain embodiments, drug-scaffold conjugates can provide for enhanced serum half-life of the drug.

In general a "carrier protein" is a protein that is biologically inert, is susceptible to modification as disclosed herein, and which can provide for solvent-accessible presentation of the moiety of interest conjugated to the carrier protein through a modified amino acid residue in the carrier protein (e.g., through an oxime or hydrazone bond within the converted sulfatase motif of an aldehyde tagged carrier protein) in a physiological environment. "Biologically inert" is meant to indicate the carrier protein exhibits clinically insignificant or no detectable biological activity when administered to the appropriate subject, such as when administered to a human subject. Thus, carrier proteins are biologically inert in that they, for example, are of low immunogenicity, do not exhibit significant or detectable targeting properties (e.g., do not exhibit significant or detectable activity in binding to a specific receptor), and exhibit little or no detectable biological activity that may interfere with activity of the moiety (e.g., drug or detectable label) conjugated to the aldehyde-tagged carrier protein. By "low immunogenicity" is meant that the carrier protein elicits little or no detectable immune response upon administration to a subject, such as a mammalian subject, e.g., a human subject. Carrier proteins can be provided in monomeric or multimeric (e.g., dimeric) forms.

Carrier proteins having a three-dimensional structure when folded that provides for multiple different solvent-accessible sites that are amenable to modification (and thus conjugation to a moiety of interest) are of interest. In general, carrier proteins of interest are those that are of a size and three-dimensional folded structure so as to provide for presentation of the conjugated moiety of interest on solvent accessible surfaces in a manner that is sufficiently spatially separated so as to provide for activity and bioavailability of the conjugated moiety or moieties of interest. The carrier protein may be selected according to a variety of factors including, but not limited to, the moiety (e.g., drug or detectable label) to be conjugated to the carrier protein.

Accordingly, any of a wide variety of polypeptides can be suitable for use as carrier proteins for use in the carrier protein conjugates of the present disclosure. Such carrier proteins can include those having a naturally-occurring amino acid sequence, fragments of naturally-occurring polypeptides, and non-naturally occurring polypeptides and fragments thereof.

Examples of carrier proteins include, but are not limited to, albumin and fragments thereof (e.g., human serum albumin, bovine serum albumin, and the like), transferrin and fragments thereof (e.g. human transferrin), and Fc fragments having reduced binding to a mammalian Fc receptor, particularly a human Fc receptor (e.g., a modified Fc fragment of an antibody (e.g., IgG), such as a mammalian antibody, e.g., a human antibody). Examples of modified Fc fragments having reduced Fc receptor binding are exemplified by the Fc fragments of Herceptin (trastuzumab) and Rituxan (Rituximab), which contain point mutations that provide for reduced Fc receptor binding (see, e.g., Clynes et al., Nature Medicine (2000), 6, 443-446). Alternatively or in addition, the isotype of the Fc fragment can be selected according to a desired level of Fc receptor binding (e.g., use of an Fc fragment of an IgG4 isotype human heavy chain constant region rather than from IgG1 or IgG3. (see, e.g., Fridman FASEB J 1991 September; 5 (12): 2684-90). In general, carrier proteins can be at least about 4 kDa (e.g., about 50 amino acid residues in length), usually at least about 25 kDa, and can be larger in size (e.g., transferrin has a molecular weight of 90 kDa while Fc fragments can have molecular weights of 30 kDa to 50 kDa).

The conjugates described herein can be used for a variety of applications including, but not limited to, visualization using fluorescence or epitope labeling (e.g., electron microscopy using gold particles equipped with reactive groups for conjugation to the compounds and conjugates described herein); protein immobilization (e.g., protein microarray production); protein dynamics and localization studies and applications; and conjugation of proteins with a moiety of interest (e.g., moieties that improve a parent protein's half-life (e.g., poly(ethylene glycol)), targeting moieties (e.g., to enhance delivery to a site of action), and biologically active moieties (e.g., a therapeutic moiety).

The polypeptide conjugate may include a polypeptide conjugated to a moiety or moieties that provide for one or more of a wide variety of functions or features. In general, examples of moieties include, but are not limited to, the following: detectable labels (e.g., fluorescent labels or fluorophores); light-activated dynamic moieties (e.g., azobenzene mediated pore closing, azobenzene mediated structural changes, photodecaging recognition motifs); water soluble polymers (e.g., PEGylation); purification tags (e.g., to facilitate isolation by affinity chromatography (e.g., attachment of a FLAG epitope); membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); targeted delivery moieties, (e.g., ligands for binding to a target receptor (e.g., to facilitate viral attachment, attachment of a targeting protein present on a liposome, etc.)), and the like.

Specific, non-limiting examples are provided below.

Drugs for Conjugation to a Polypeptide

Any of a number of drugs are suitable for use, or can be modified to be rendered suitable for use, as a reactive partner to conjugate to a polypeptide. Examples of drugs include small molecule drugs and peptide drugs. Thus, the present disclosure provides drug-polypeptide conjugates.

"Small molecule drug" as used herein refers to a compound, e.g., an organic compound, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof. See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); and duocarmycins and active analogs and derivatives thereof (e.g., including the synthetic analogues, KW-2189 and CB 1-TM1).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™ TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Methods for Modification of Drugs to Contain a Reactive Partner

Drugs to be conjugated to a polypeptide may be modified to incorporate a reactive partner for reaction with the polypeptide. Where the drug is a peptide drug, the reactive moiety (e.g., aminooxy or hydrazide can be positioned at an N-terminal region, the N-terminus, a C-terminal region, the C-terminus, or at a position internal to the peptide. For example, an example of a method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethylcarbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the amino acid residue to reaction with a reactive partner of interest) are of importance, Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with a compound or conjugate disclosed herein are also contemplated for use as drugs in the polypeptide-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Peptide Drugs

In some cases, a conjugate comprises a covalently linked peptide. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

In some embodiments, the peptide can be chemically synthesized to include a group reactive with an amino acid residue or a modified amino acid residue of the polypeptide. A suitable synthetic peptide has a length of from 5 amino acids to 100 amino acids, or longer than 100 amino acids; e.g., a suitable peptide has a length of from 5 amino acids (aa) to 10 aa, from 10 aa to 15 aa, from 15 aa to 20 aa, from 20 aa to 25 aa, from 25 aa to 30 aa, from 30 aa to 40 aa, from 40 aa to 50 aa, from 50 aa to 60 aa, from 60 aa to 70 aa, from 70 aa to 80 aa, from 80 aa to 90 aa, or from 90 aa to 100 aa.

In certain embodiments, a peptide can be modified to contain an α-nucleophile-containing moiety (e.g., an aminooxy or hydrazide moiety), e.g., can be reacted with an fGly-containing polypeptide to yield a conjugate in which the polypeptide and peptide are linked by a hydrazone or oxime bond, respectively. Examples of methods of synthesizing a peptide, such that the synthetic peptide comprising a reactive group reactive with an amino acid residue or a modified amino acid residue of the polypeptide, are described above.

Suitable peptides include, but are not limited to, hLF-11 (an 11-amino acid N-terminal fragment of lactoferrin), an anti-microbial peptide; granulysin, an anti-microbial peptide; Plectasin (NZ2114; SAR 215500), an anti-microbial peptide; viral fusion inhibitors such as Fuzeon (enfuvirtide), TRI-1249 (T-1249; see, e.g., Matos et al. (2010) *PLoS One* 5:e9830), TRI-2635 (T-2635; see, e.g., Eggink et al. (2009) *J. Biol. Chem.* 284:26941), T651, and TRI-1144; C5a receptor inhibitors such as PMX-53, JPE-1375, and JSM-7717; POT-4, a human complement factor C3 inhibitor; Pancreate (an INGAP derivative sequence, a HIP-human proislet protein); somatostatin; a somatostatin analog such as DEBIO 8609 (Sanvar), octreotide, octreotide (C2L), octreotide QLT, octreotide LAR, Sandostatin LAR, SomaLAR, Somatuline (lanreotide), see, e.g., Deghenghi et al. (2001) *Endocrine* 14:29; TH9507 (Tesamorelin, a growth hormone-releasing factor); POL7080 (a protegrin analog, an anti-microbial peptide); relaxin; a corticotropin releasing factor agonist such as urotensin, sauvagine, and the like; a heat shock protein derivative such as DiaPep277; a human immunodeficiency virus entry inhibitor; a heat shock protein-20 mimic such as AZX100; a thrombin receptor activating peptide such as TP508 (Chrysalin); a urocortin 2 mimic (e.g., a CRF2 agonist) such as urocortin-2; an immune activator such as Zadaxin (thymalfasin; thymosin-al), see, e.g., Sjogren (2004) *J. Gastroenterol. Hepatol.* 19:S69; a hepatitis C virus (HCV) entry inhibitorE2 peptide such as HCV3; an atrial natriuretic peptide such as HANP (Sun 4936; carperitide); an annexin peptide; a defensin (anti-microbial peptide) such as hBD2-4; a defensin (anti-microbial peptide) such as hBD-3; a defensin (anti-microbial peptide) such as PMX-30063; a histatin (anti-microbial peptide) such as histatin-3, histatin-5, histatin-6, and histatin-9; a histatin (anti-microbial peptide) such as PAC-113; an indolicidin (anti-microbial peptide) such as MX-594AN (Omniganin; CLS001); an indolicidin (anti-microbial peptide) such as Omnigard (MBI-226; CPI-226); an anti-microbial peptide such as an insect cecropin; an anti-microbial peptide such as a lactoferrin (talactoferrin); an LL-37/cathelicidin derivative (an anti-microbial peptide) such as P60.4 (OP-145); a magainin (an anti-microbial peptide) such as Pexiganan (MSI-78; Suponex); a protegrin (an anti-microbial peptide) such as IB-367 (Iseganan); an agan peptide; a beta-natriuretic peptide such as Natrecor, or Noratak (Nesiritide), or ularitide; bivalarudin (Angiomax), a thrombin inhibitor; a C peptide derivative; a calcitonin such as Miacalcin (Fortical); an enkephalin derivative; an erythropoiesis-stimulating peptide such as Hematide; a gap junction modulator such as Danegaptide (ZP1609); a gastrin-releasing peptide; a ghrelin; a glucagon-like peptide; a glucagon-like peptide-2 analog such as ZP1846 or ZP1848; a glucosaminyl muramyl dipeptide such as GMDP; a glycopeptide antibiotic such as Oritavancin; a teicoplanin derivative such as Dalbavancin; a gonadotropin releasing hormone (GnRH) such as Zoladex (Lupon) or Triptorelin; a histone deacetylase (HDAC) inhibitor depsipeptide such as PM02734 (Irvalec); an integrin such as eptifibatide; an insulin analog such as Humulog; a kahalalide depsipeptide such as PM02734; a kallikrein inhibitor such as Kalbitor (ecallantide); an antibiotic such as Telavancin; a lipopeptide such as Cubicin or MX-2401; a lutenizing hormone releasing hormone (LHRH) such as goserelin; an LHRH synthetic decapeptide agonist analog such as Treistar (triptorelin pamoate); an LHRH such as Eligard; an M2 protein channel peptide inhibitor; metreleptin; a melanocortin receptor agonist peptide such as bremalanotide/PT-141; a melanocortin; a muramyl tripeptide such as Mepact (mifamurtide); a myelin basic protein peptide such as MBP 8298 (dirucotide); an N-type voltage-gated calcium channel blocker such as Ziconotide (Prialt); a parathyroid hormone peptide; a parathyroid analog such as 768974; a peptide hormone analog such as UGP281; a prostaglandin F2-α receptor inhibitor such as PDC31; a protease inhibitor such as PPL-100; surfaxin; a thrombospondin-1 (TSP-1) mimetic such as CVX-045 or ABT 510; a vasoactive intestinal peptide; vasopressin; a Y2R agonist peptide such as RG7089; obinepeptide; and TM30339.

Detectable Labels

The conjugates, compounds and methods of the present disclosure can be used to conjugate a detectable label to polypeptide. Examples of detectable labels include, but are not limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh and the like), biotin (e.g., to be detected through reaction of biotin and avidin), fluorescent tags, imaging reagents, and the like. Detectable labels also include peptides or polypeptides that can be detected by antibody binding, e.g., by binding of a detectably labeled antibody or by detection of bound antibody through a sandwich-type assay. Further examples of detectable labels include, but are not limited to, dye labels (e.g., chromophores, fluorophores, such as, but not limited to, Alexa Fluor® fluorescent dyes (e.g., Alexa Fluor® 350, 405, 430, 488, 532, 546, 555, 568, 594, 595, 610, 633, 635, 647, 660, 680, 700, 750, 790, and the like)), biophysical probes (spin labels, nuclear magnetic resonance (NMR) probes), Firster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like), localization tags (e.g., to identify association of a tagged polypeptide at the tissue or molecular cell level (e.g., association with a tissue type, or particular cell membrane), and the like.

Attachment of Moieties for Delivery to a Target Site

Embodiments of the present disclosure also include a polypeptide conjugated to one or more moieties, such as, but not limited to, a drug (e.g., a small molecule drug), toxin, or other molecule for delivery to a target site (e.g., a cell) and which can provide for a pharmacological activity or can serve as a target for delivery of other molecules.

Also contemplated are conjugates that include one of a pair of binding partners (e.g., a ligand, a ligand-binding portion of a receptor, a receptor-binding portion of a ligand, etc.). For example, the conjugate can include a polypeptide that serves as a viral receptor and, upon binding with a viral envelope protein or viral capsid protein, facilitates attachment of virus to the cell surface on which the modified polypeptide is expressed. Alternatively, the conjugate may include an antigen that is specifically bound by an antibody (e.g., monoclonal antibody), to facilitate detection and/or separation of host cells expressing the modified polypeptide.

Attachment of Target Molecules to a Support

The methods can provide for conjugation of a polypeptide to a moiety to facilitate attachment of the polypeptide to a solid substrate (e.g., to facilitate assays), or to a moiety to facilitate easy separation (e.g., a hapten recognized by an antibody bound to a magnetic bead). In some embodiments, the methods are used to provide for attachment of a protein to an array (e.g., chip) in a defined orientation. For example, a polypeptide modified at a selected site (e.g., at or near the N-terminus) can be generated, and the methods, conjugates and compounds used to deliver a moiety to the modified polypeptide. The moiety can then be used as the attachment site for affixing the polypeptide to a support (e.g., solid or semi-solid support, such as a support suitable for use as a microchip in high-throughput assays).

Water-Soluble Polymers

In some cases, a conjugate includes a covalently linked water-soluble polymer. A moiety of particular interest is a water-soluble polymer. A "water-soluble polymer" refers to a polymer that is soluble in water and is usually substantially non-immunogenic, and usually has an atomic molecular weight greater than 1,000 Daltons. The methods, conjugates and compounds described herein can be used to attach one or more water-soluble polymers to a polypeptide. Attachment of a water-soluble polymer (e.g., PEG) to a polypeptide, such as a pharmaceutically active (e.g., therapeutic) polypeptide can be desirable as such modification can increase the therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In some embodiments, the water-soluble polymer has an effective hydrodynamic molecular weight of greater than 5,000 Da, greater than 10,000 Da, greater than 20,000 to 500,000 Da, greater than 40,000 Da to 300,000 Da, greater than 50,000 Da to 70,000 Da, such as greater than 60,000 Da. In some embodiments, the water-soluble polymer has an effective hydrodynamic molecular weight of from 10 kDa to 20 kDa, from 20 kDa to 25 kDa, from 25 kDa to 30 kDa, from 30 kDa to 50 kDa, or from 50 kDa to 100 kDa. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of 200 Da to 80,000 Da, or 1,500 Da to 42,000 Da, including 2,000 to 20,000 Da. Unless referred to specifically, molecular weight is intended to refer to atomic molecular weight. Linear, branched, and terminally charged water soluble polymers (e.g., PEG) may be used.

Polymers useful as moieties to be attached to a polypeptide can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalkylene glycol and derivatives thereof, including polyethylene glycol, methoxy-polyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above include polyalkylene oxide based polymers, such as polyethylene glycol "PEG" (See. e.g., "Poly(ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Examples of polymers of interest include those containing a polyalkylene oxide, polyamide alkylene oxide, or derivatives thereof, including polyalkylene oxide and polyamide alkylene oxide comprising an ethylene oxide repeat unit of the formula $-(CH_2-CH_2-O)-$. Further examples of polymers of interest include a polyamide having a molecular weight greater than 1,000 Daltons of the formula $-[C(O)-X-C(O)-NH-Y-NH]_n-$ or $-[NH-Y-NH-C(O)-X-C(O)]_n-$, where X and Y are divalent radicals that may be the same or different and may be branched or linear, and n is a discrete integer from 2-100, such as from 2 to 50, and where either or both of X and Y comprises a biocompatible, substantially non-antigenic water-soluble repeat unit that may be linear or branched. Further examples of water-soluble repeat units comprise an ethylene oxide of the formula $-(CH_2-CH_2-O)-$ or $-(CH_2-CH_2-O)-$. The number of such water-soluble repeat units can vary significantly, with the number of such units being from 2 to 500, 2 to 400, 2 to 300, 2 to 200, 2 to 100, for example from 2 to 50. An example of an embodiment is one in which one or both of X and Y is selected from: $-((CH_2)_{n1}-(CH_2-CH_2-O)_{n2}-(CH_2)-$ or $-((CH_2)_{n1}-(O-CH_2-CH_2)_{n2}-(CH_2)_{n-1}-)$, where n1 is 1 to 6, 1 to 5, 1 to 4, or 1 to 3, and where n2 is 2 to 50, 2 to 25, 2 to 15, 2 to 10, 2 to 8, or 2 to 5. A further example of an embodiment is one in which X is $-(CH_2-CH_2)-$, and where Y is $-(CH_2-(CH_2-CH_2-O)_3-CH_2-CH_2-CH_2)-$ or $-(CH_2-CH_2-CH_2-(O-CH_2-CH_2)_3-CH_2)-$.

The polymer can include one or more spacers or linkers. Examples of spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes ($-NH-C(O)-O-$)>polyorthoesters ($-O-C((OR)(R'))-O-$)>polyamides ($-C(O)-NH-$). Similarly, the linkage systems attaching a water-soluble polymer to a target molecule may be biostable or biodegradable, e.g., from less stable to more stable: carbonate ($-O-C(O)-O-$)>ester ($-C(O)-O-$)>urethane ($-NH-C(O)-O-$)>orthoester ($-O-C((OR)(R'))-O-$)>amide ($-C(O)-NH-$). In general, it may be desirable to avoid use of a sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Formulations

The conjugates (including antibody conjugates) of the present disclosure can be formulated in a variety of different ways. In general, where the conjugate is a polypeptide-drug conjugate, the conjugate is formulated in a manner compatible with the drug conjugated to the polypeptide, the condition to be treated, and the route of administration to be used.

The conjugate (e.g., polypeptide-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those available in the art. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The polypeptide-drug conjugates of the present disclosure find use in treatment of a condition or disease in a subject that is amenable to treatment by administration of the parent drug (i.e., the drug prior to conjugation to the polypeptide). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the parent drug. Accordingly, a variety of subjects may be amenable to treatment using the polypeptide-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of polypeptide-drug conjugate administered can be initially determined based on guidance of a dose and/or dosage regimen of the parent drug. In general, the polypeptide-drug conjugates can provide for targeted delivery and/or enhanced serum half-life of the bound drug, thus providing for at least one of reduced dose or reduced administrations in a dosage regimen. Thus, the polypeptide-drug conjugates can provide for reduced dose and/or reduced administration in a dosage regimen relative to the parent drug prior to being conjugated in an polypeptide-drug conjugate of the present disclosure.

Furthermore, as noted above, because the polypeptide-drug conjugates can provide for controlled stoichiometry of drug delivery, dosages of polypeptide-drug conjugates can be calculated based on the number of drug molecules provided on a per polypeptide-drug conjugate basis.

In some embodiments, multiple doses of a polypeptide-drug conjugate are administered. The frequency of administration of a polypeptide-drug conjugate can vary depending on any of a variety of factors, e.g., severity of the symptoms, condition of the subject, etc. For example, in some embodiments, a polypeptide-drug conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

Methods of Treating Cancer

The present disclosure provides methods for delivering a cancer chemotherapeutic agent to an individual having a cancer. The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Synthesis of HIPS-AF594

A hydrazinyl-indole detectable label conjugate (HIPS-AF594) was synthesized as illustrated in Scheme 1, below:

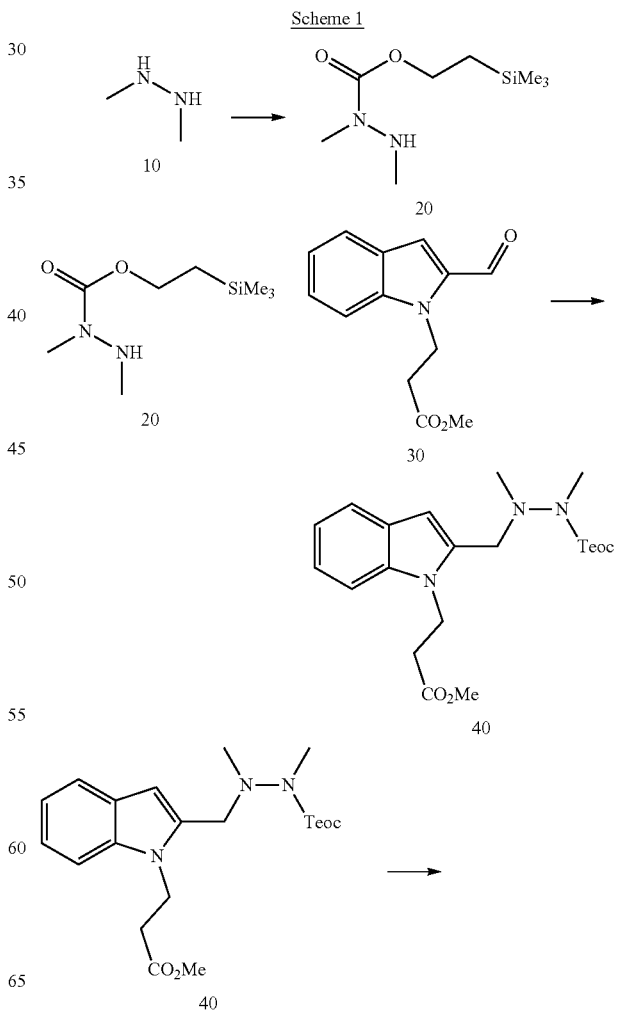

93
-continued

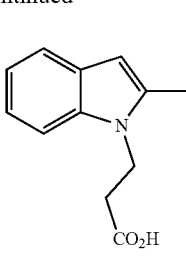

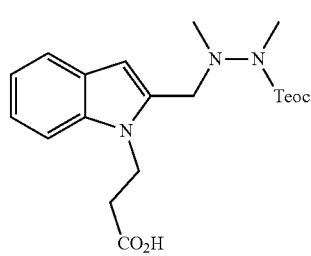
50
(Teoc-HIPS-OH)

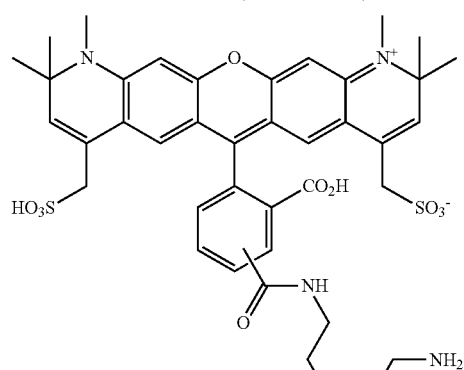
60
(AF594)

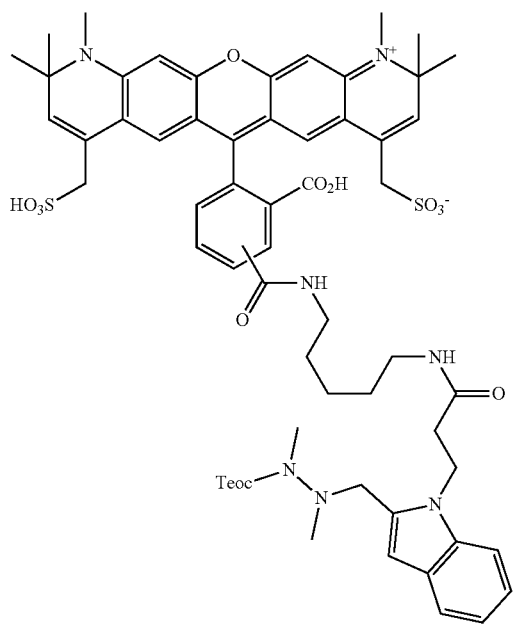
70
(Teoc-HIPS-AF594)

94
-continued

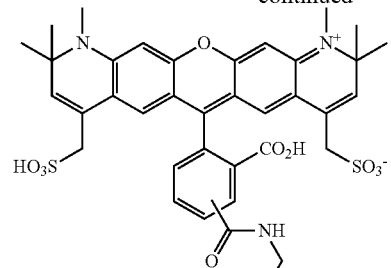

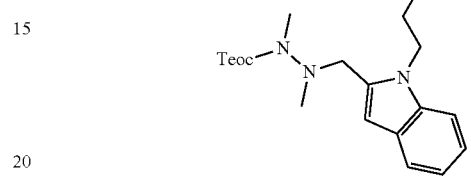
70
(Teoc-HIPS-AF594)

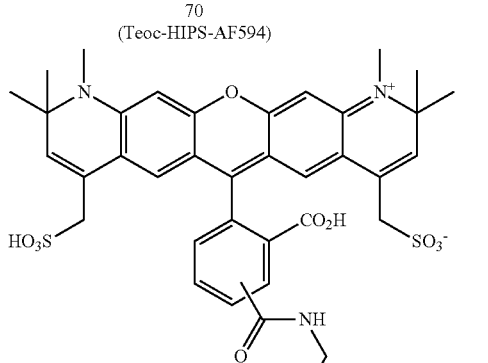
80
(HIPS-AF594)

Compound 20 (2-(trimethylsilyl)ethyl 1,2-dimethylhydrazinecarboxylate) was synthesized from Compound 10 as follows. To a vigorously stirred suspension of sym-dimethylhydrazine dihydrochloride (7.5 mmol) in 15 mL MeCN was added triethylamine (18.8 mmol). The resulting white suspension was filtered and cooled to 0° C. While stirring, N-[2-(trimethylsilyl)ethoxycarbonyloxy]succinimide (3.7 mmol) in 2 mL MeCN was added dropwise over 10 min. The reaction was allowed to warm to RT over 16 hr with stirring. The crude reaction was concentrated in vacuo, then partitioned between 100 mL EtOAc and 30 mL water. The organic phase was washed 3×30 mL brine, dried over $MgSO_4$, filtered and concentrated in vacuo to afford the product in a 64% yield. The product required no further purification. $^1$H NMR (400 MHz, $CDCl_3$) δ 4.5 (bs, 1H), 4.20 (dd, J=8.8, 8.4 Hz, 2H), 3.03 (s, 3H), 2.57 (s, 3H), 1.02 (dd, J=8.8, 8.4 Hz, 2H), 0.04 (s, 9H).

Compound 40 (2-(trimethylsilyl)ethyl 2-((1-(3-methoxy-3-oxopropyl)-1H-indol-2-yl)methyl)-1,2-dimethylhydrazinecarboxylate) was synthesized from Compound 20 and Compound 30 as follows. An oven dried 4 mL vial was charged with Compound 30 (methyl 3-(2-formyl-1H-indol-1-yl)propanoate; 0.0606 mmol), Compound 20 (2-(trimethylsilyl)ethyl 1,2-dimethylhydrazinecarboxylate; 0.0828 mmol), acetic acid (0.0727 mmol) in 150 µL anhydrous methanol. Sodium cyanoborohydride (0.0727 mmol) was added in 100 µL anhydrous methanol and stirred for 16 hr. The crude reaction mixture was purified by preparatory TLC (500 m thickness, silica gel) using a mobile phase of 15% EtOAc:Hexanes to afford the product in a 45% yield. $^1$H NMR (400 MHz, CDCl$_3$) δ7.57 (d, J=7.6 Hz, 1H), 7.35 (d, J=8.4 Hz, 1H), 7.22 (ddd, J=8.0, 7.2, 1.2 Hz, 1H), 7.10 (ddd, J=8.0, 7.2, 1.2 Hz, 1H), 6.40 (s, 1H), 4.65 (bs, 2H), 4.26-4.11 (m, 4H), 3.70 (s, 3H), 2.90 (m, 5H), 2.66 (s, 3H), 0.99 (t, J=8.4, 2H), 0.05 (s, 9H).

Compound 50 (3-(2-((1,2-dimethyl-2-((2-(trimethylsilyl)ethoxy)carbonyl)hydrazinyl)methyl)-1H-indol-1-yl)propanoic acid; also referred to as Teoc-HIPS-OH) was synthesized from Compound 40 as follows. A 4 mL vial was charged with Compound 40 (2-(trimethylsilyl)ethyl 2-((1-(3-methoxy-3-oxopropyl)-1H-indol-2-yl)methyl)-1,2-dimethylhydrazinecarboxylate; 0.027 mmol), lithium hydroxide (0.054 mmol) and 250 µL of methanol and stirred for 24 h. The solution was concentrated in vacuo, then chromatographed in 1% AcOH:EtOAc to yield the desired product in an 89% yield. $^1$H NMR (400 MHz, CDCl$_3$) δ7.57 (d, J=7.6 Hz, 1H), 7.38 (d, J=8.0 Hz, 1H), 7.24 (ddd, J=8.0, 7.6, 0.8 Hz, 1H), 7.12 (ddd, J=7.6, 7.6, 0.8 Hz, 1H), 6.40 (s, 1H), 4.63 (bs, 2H), 4.20 (t, J=8.4 Hz, 2H), 4.13 (s, 2H), 3.11-2.97 (m, 5H), 2.58 (s, 3H), 2.66 (s, 3H), 0.99 (t, J=8.4, 2H), 0.05 (s, 9H). LRMS (ESI) calcd for C$_{20}$H$_{31}$N$_3$O$_4$Si [M+H]$^+$: 406.22; found 405.9.

Compound 70 (Teoc-HIPS-AF594) was synthesized from Compound 50 (Teoc-HIPS-OH) and Compound 60 (AF594) as follows. To a solution of Compound 60 (AF594; 0.00124 mmol), Compound 50 (Teoc-HIPS-OH; 0.0059 mmol), triethylamine (0.0059 mmol) in 200 µL 1:1 DCM:DMF was added HATU ((dimethylamino)-N,N-dimethyl(3H-[1,2,3]triazolo[4,5-b]pyridin-3-yloxy)methaniminium hexafluorophosphate; 0.0031). The reaction was stirred for 4 h. The crude reaction was mixture was purified by flash chromatography (C18) using a 0-33% MeCN:water gradient. LRMS (ESI) calcd for C$_{61}$H$_{77}$N$_7$O$_{12}$S$_2$Si [M+H]$^+$: 1192.49; found 1194.1.

Compound 80 (HIPS-AF594) was synthesized from Compound 70 (Teoc-HIPS-AF594) as follows. To a solution of Compound 70 (Teoc-HIPS-AF594; 0.67 µmol) in 100 µL DMF was added 1 mg of CsF (6.6 µmol) and heated to 60° C. for 2 hr. The reaction was then cooled to room temperature and chromatographed (C18) with a gradient of 0-50% MeCN:water to yield 0.4 mg of a mixture of desired product and desired product+CH$_2$ (addition of formaldehyde). LRMS (ESI) calcd for C$_{54}$H$_{63}$N$_7$O$_{11}$S$_2$[M+H]$^+$: 1050.41; found 1151.4.

Synthesis of Fmoc-HIPS-OPFP

Fmoc-HIPS-OPFP ((9H-fluoren-9-yl)methyl 1,2-dimethyl-2-((1-(3-oxo-3-(perfluorophenoxy)propyl)-1H-indol-2-yl)methyl)hydrazinecarboxylate) was synthesized as illustrated in Scheme 2, below:

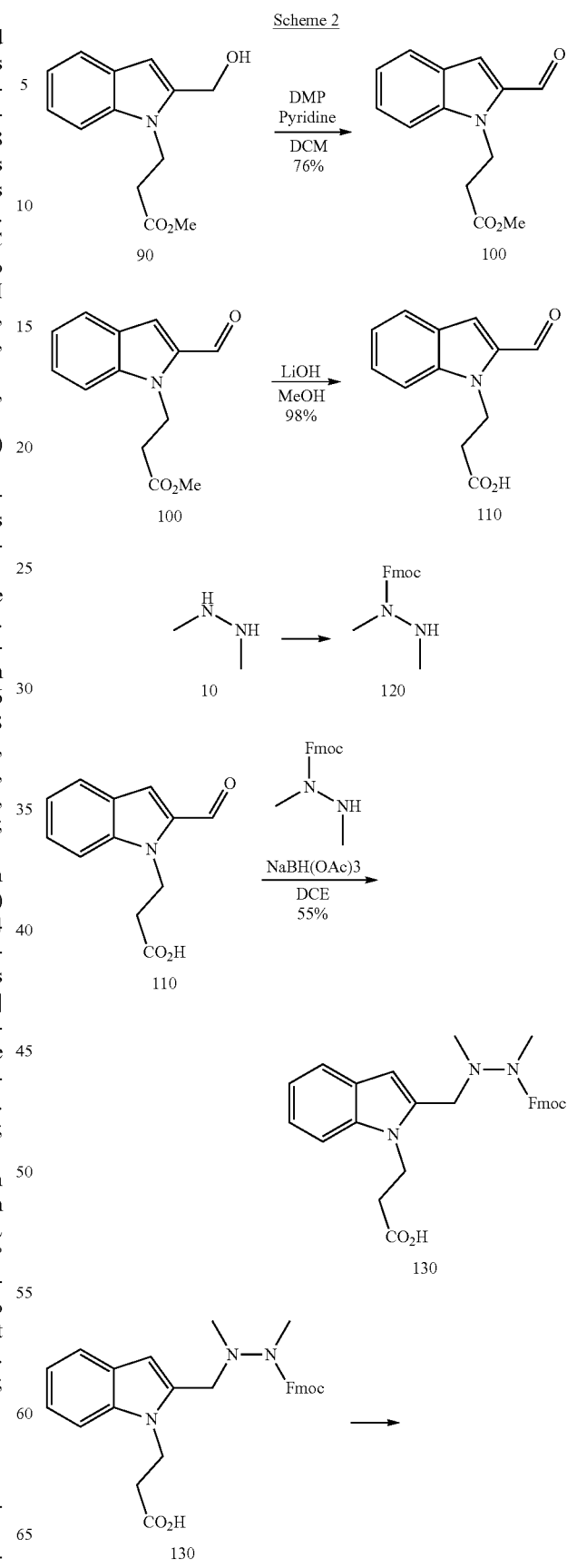

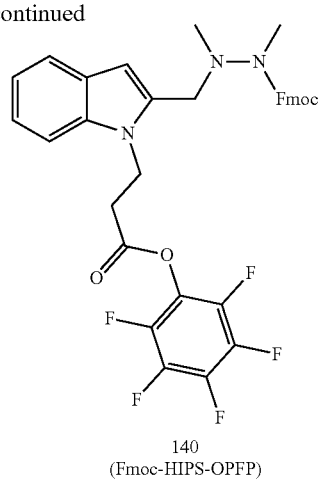

140
(Fmoc-HIPS-OPFP)

Compound 100 (methyl 3-(2-formyl-1H-indol-1-yl)propanoate) was synthesized from Compound 90 as follows. To a solution of Dess-Martin Periodinane (1.2 mmol) in 5 mL DCM was added 3 mmol of pyrindine and sonicated until soluble, whereupon 1 mmol of Compound 90 (methyl 3-(2-(hydroxymethyl)-1H-indol-1-yl)propanoate) was added and the solution stirred for 2.5 h. The reaction mixture was then concentrated and chromatographed in DCM to afford 0.76 mmol of product. $^1$H NMR (400 MHz, CDCl$_3$) δ 9.90 (s, 1H), 7.75 (d, J=8.4 Hz, 1H), 7.53 (dd, J=8.4, 0.8 Hz, 1H), 7.45 (ddd, J=8.0, 6.8, 0.8 Hz, 1H), 7.32 (d, J=0.8 Hz, 1H), 7.19 (ddd, J=8.0, 6.8, 0.8 Hz, 1H), 4.86 (t, J=7.2 Hz, 2H), 3.64 (s, 3H), 2.86 (t, J=7.2 Hz, 2H).

Compound 110 (3-(2-formyl-1H-indol-1-yl)propanoic acid) was synthesized from Compound 100 as follows. To a solution of 1.03 mmol of Compound 100 (methyl 3-(2-formyl-1H-indol-1-yl)propanoate) in 5 mL methanol was added 3.09 mmol of lithium hydroxide and stirred for 5 h, upon which the solution was acidified to pH 2 and partitioned between 5 mL water and 15 mL ethyl acetate. The aqueous phase was washed 2×10 mL ethyl acetate. The combined organic phases were washed 1×10 mL Brine, then dried over magnesium sulfate, filtered and concentrated by rotary evaporation to yield 1.01 mmol of product. The crude material was pure by NMR and taken on to the subsequent reaction. $^1$H NMR (400 MHz, CDCl$_3$) δ 9.89 (s, 1H), 7.76 (d, J=8.4 Hz, 1H), 7.52 (d, J=8.4 Hz, 1H), 7.45 (ddd, J=8.4, 6.8, 1.2 Hz, 1H), 7.33 (s), 7.22 (dd, J=6.8, 0.8 Hz, 1H), 4.86 (t, J=7.2 Hz, 2H), 2.91 (t, J=7.2 Hz, 2H).

Compound 120 ((9H-fluoren-9-yl)methyl 1,2-dimethylhydrazinecarboxylate) was synthesized from Compound 10 according to literature procedure as described in Nicolas, I. et al. Synlett. 2011, 3, 327-330, the disclosure of which is incorporated herein by reference.

Compound 130 (3-(2-((2-(((9H-fluoren-9-yl)methoxy)carbonyl)-1,2-dimethylhydrazinyl)methyl)-1H-indol-1-yl)propanoic acid) was synthesized from Compound 110 and Compound 120 as follows. A 50 mL flame dried round bottom flask was charged with Compound 110 (3-(2-formyl-1H-indol-1-yl)propanoic acid; 3.22 mmol), Compound 120 ((9H-fluoren-9-yl)methyl 1,2-dimethylhydrazinecarboxylate; 5.0 mmol) and dissolved in 26 mL dichloroethane (DCE). To this flask, sodium triacetoxyborohydride (3.54 mmol) was added portionwise and stirred for three hours then quenched with 5 mL lM NaOH (aq) and stirred for 5 min. The reaction was acidified to pH 2 and partitioned with 50 mL DCM. The organic phase was extracted three times with 10 mL 5% citric acid (aq), then dried over MgSO$_4$, filtered and concentrated in vacuo to afford 55% of the desired product.

Compound 140 ((9H-fluoren-9-yl)methyl 1,2-dimethyl-2-((1-(3-oxo-3-(perfluorophenoxy)propyl)-1H-indol-2-yl)methyl)hydrazinecarboxylate; also referred to as Fmoc-HIPS-OPFP) was synthesized from Compound 130 as follows. A flame dried round bottom flask was charged with Compound 130 (3-(2-((2-(((9H-fluoren-9-yl)methoxy)carbonyl)-1,2-dimethylhydrazinyl)methyl)-1H-indol-1-yl)propanoic acid; 0.574 mmol), pentafluorophenol (PFP; 0.631 mmol), 5 mL ethyl acetate (dry) and then cooled to 0° C. To this solution was added N,N'-dicyclohexylcarbodiimide (0.631 mmol) in 0.5 mL EtOAc and allowed to warm to 20° C. with stirring. Upon consumption of starting material by TLC (~2 h), the crude reaction was diluted in 60 mL EtOAc, washed 2×20 mL water, 2×20 mL brine, dried over MgSO$_4$, filtered and concentrated in vacuo. This material was used in subsequent reactions without further purification.

Synthesis of HIPS-6PEG-Maytansine

HIPS-6PEG-Maytansine was synthesized as illustrated in Scheme 3, below:

Scheme 3

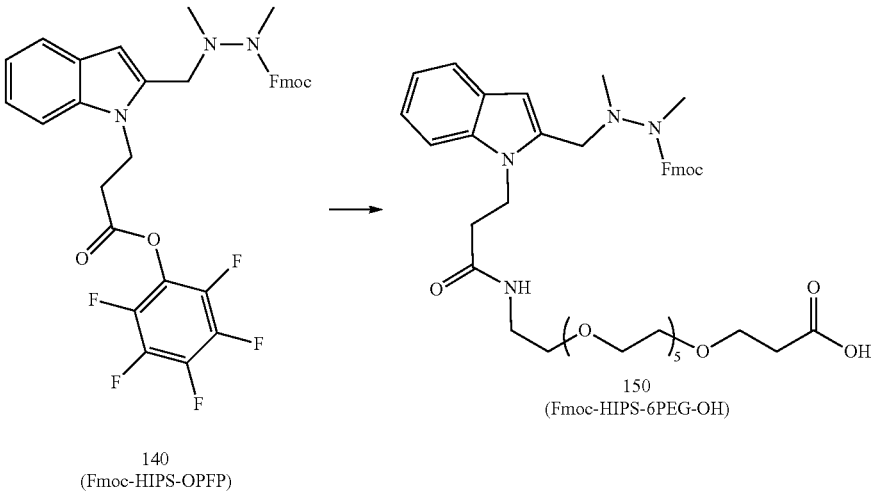

140
(Fmoc-HIPS-OPFP)

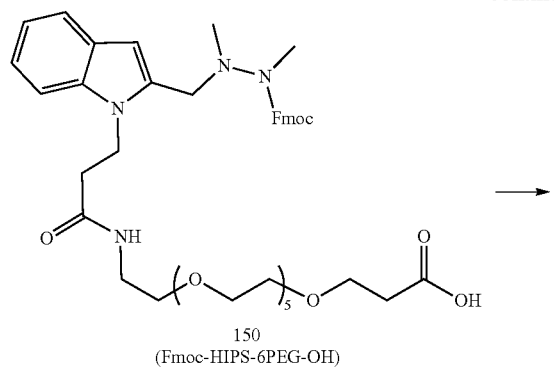
150
(Fmoc-HIPS-6PEG-OH)
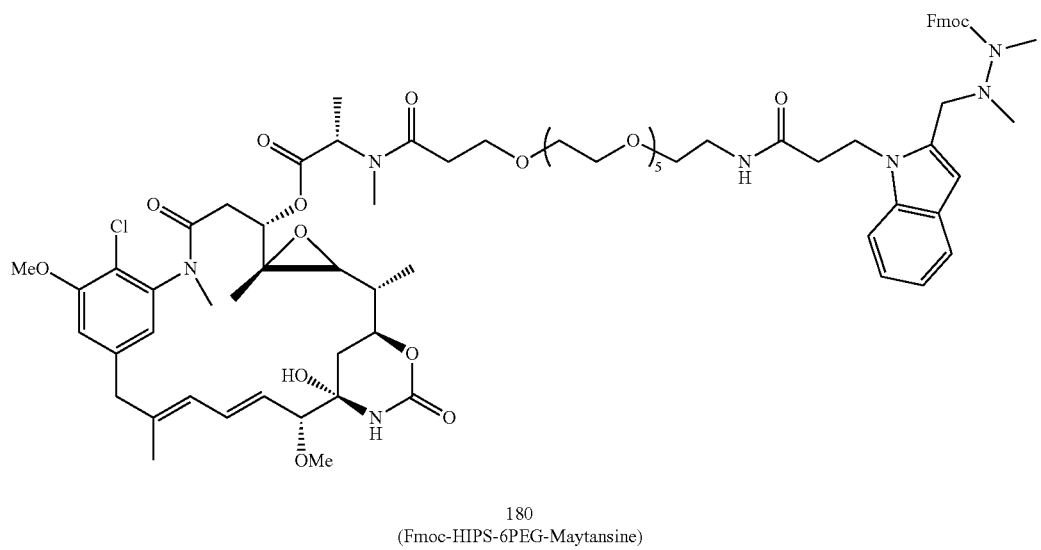
180
(Fmoc-HIPS-6PEG-Maytansine)
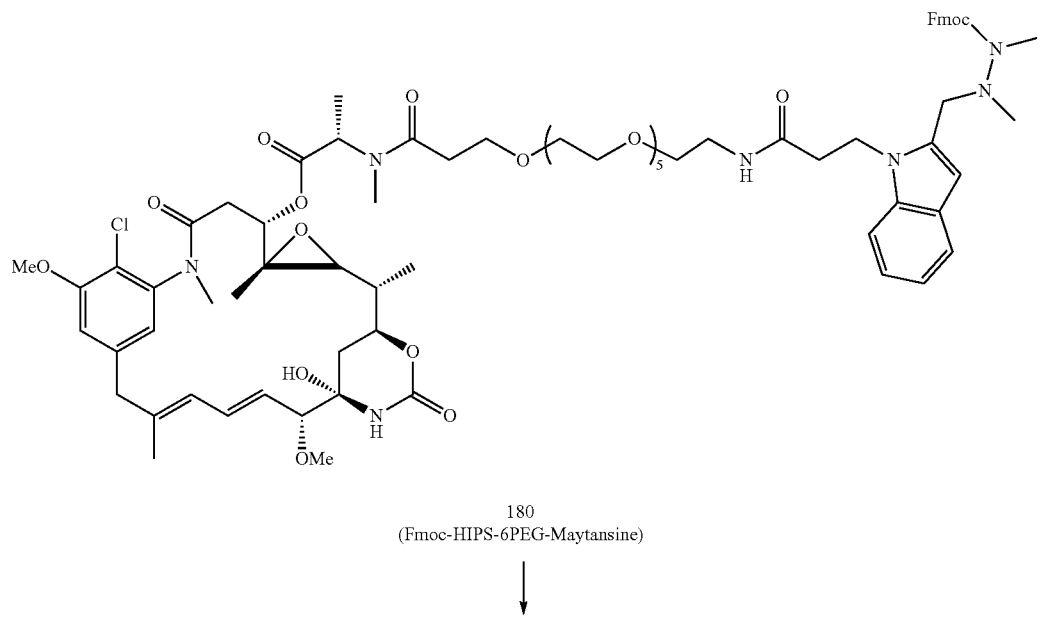
180
(Fmoc-HIPS-6PEG-Maytansine)

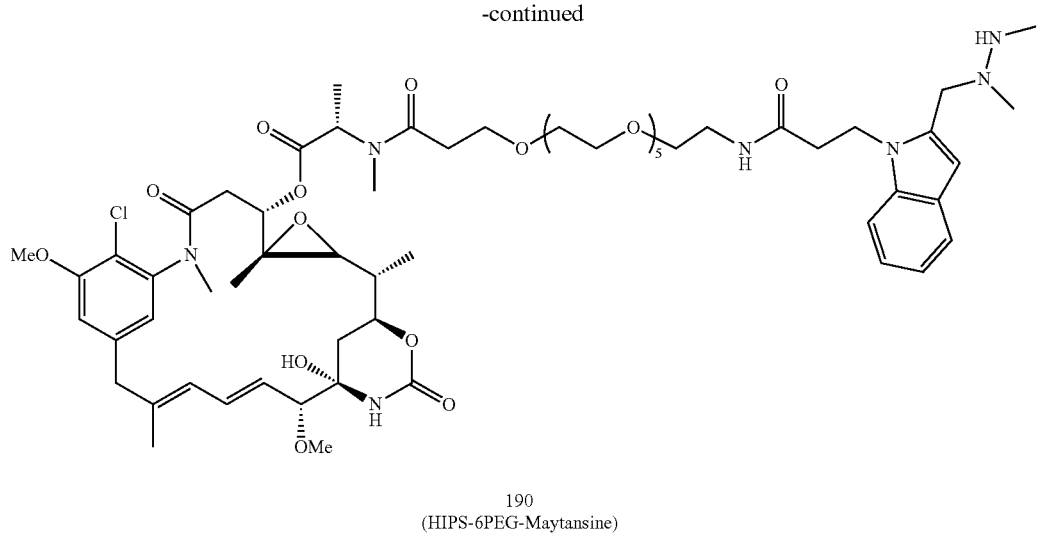

190
(HIPS-6PEG-Maytansine)

Compound 150 (Fmoc-HIPS-6PEG-OH) was synthesized from Compound 140 (Fmoc-HIPS-OPFP) as follows. A 1.6 mL vial was charged with Compound 140 (Fmoc-HIPS-OPFP; 66.6 mg, 0.1 mmol), 1-amino-3,6,9,12,15,18-hexaoxahenicosan-21-oic acid (74.9 mg, 0.2 mmol), DIPEA (79.5 mg, 107.1 μL, 0.6 mmol) and 1 mL of anhydrous DMF. The reaction was stirred for 2 h and then chromatographed (C18) with a gradient of 0-100% MeCN:water to afford the product as a white film (48.6 mg, 58% yield).

Compound 170 was synthesized from Compound 160, as shown in the scheme below, according to literature procedure as described in PCT/US2006/030857 (published as WO 2007/021674), the disclosure of which is incorporated herein by reference.

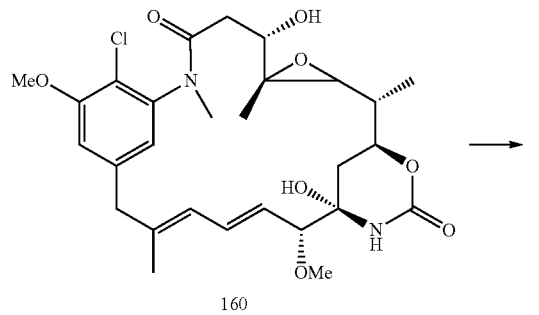

160

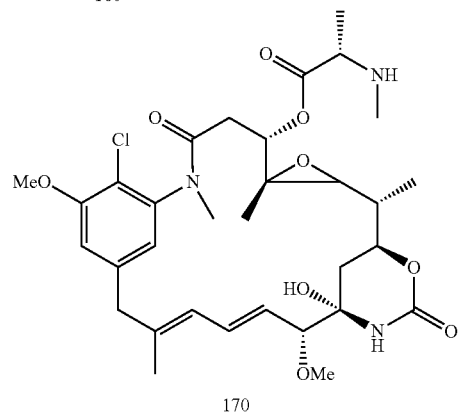

170

Compound 180 (Fmoc-HIPS-6PEG-deacyl-maytansine) was synthesized from Compound 150 (Fmoc-HIPS-6PEG-OH) and Compound 170 as follows. A 1.6 mL vial was charged with Compound 150 (Fmoc-HIPS-6PEG-OH; 18.5 mg, 0.023 mmol), HATU (8.8 mg, 0.023 mmol), DIPEA (8.8 mg, 11.9 uL, 0.068 mmol), 0.1 mL anhydrous DMF and allowed to stir for 15 min at room temperature. To this was added Compound 170 (N-Methylalanine maytansine; 14.5 mg, 0.022 mmol) in 0.1 mL anhydrous DMF. The reaction was stirred for 2 h, added to 2 mL water, and extracted with 5×1 mL EtOAc. The organic phase was washed with 1×1 mL $H_2O$, 1×1 mL 1 M HCl, 1×1 mL 1.2 M $NaHCO_3$, 1×1 mL $H_2O$, 1×1 mL 5M NaCl, and dried over $Na_2SO_4$. The product was chromatographed (silica) using a gradient of 0-10% $MeOH:CH_2Cl_2$ to afford the desired compound as a pale yellow film (19.9 mg, 62% yield).

Compound 190 (HIPS-6PEG-Maytansine) was synthesized from Compound 180 (Fmoc-HIPS-6PEG-deacyl-maytansine) as follows. A 1.6 mL vial was charged with Compound 180 (Fmoc-HIPS-6PEG-deacyl-maytansine; 19.9 mg, 0.014 mmol), piperidine (116.8 mg, 135.5 uL, 1.37 mmol), and 0.68 mL DMA. Upon consumption of the starting material, as indicated by HPLC, approximately 20 min, the crude reaction was immediately chromatographed (C18) using a 0-100% MeCN:water gradient to afford the desired product as a white film (10.2 mg, 61% yield).

Example 1

Conjugation of HIPS-A594 to an Aldehyde-Tagged IgG Antibody

HIPS-AF594 (Compound 80, above) was conjugated to an aldehyde-tagged antibody over a range of time and pH conditions. HIPS-AF594 (92.6 drug:aldehyde equivalents) was reacted with 5.4 μM aldehyde-tagged IgG antibody for 1, 2, 3, 4, or 24 hr at 37° C. in PBS pH 7.4, PBS with 100 mM potassium acetate pH 4.6, PBS with 50 mM sodium citrate pH 6.0, or PBS with 100 mM Tris pH 8.

Figure 2:
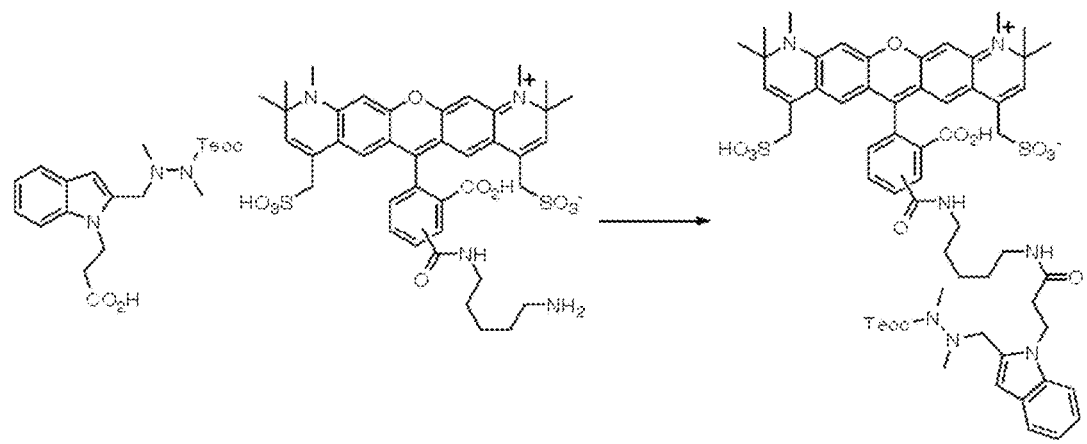
FIG. 2, panel A, shows a reaction scheme for the synthesis of a functionalized detectable label, according to embodiments of the present disclosure.
Figure 2:
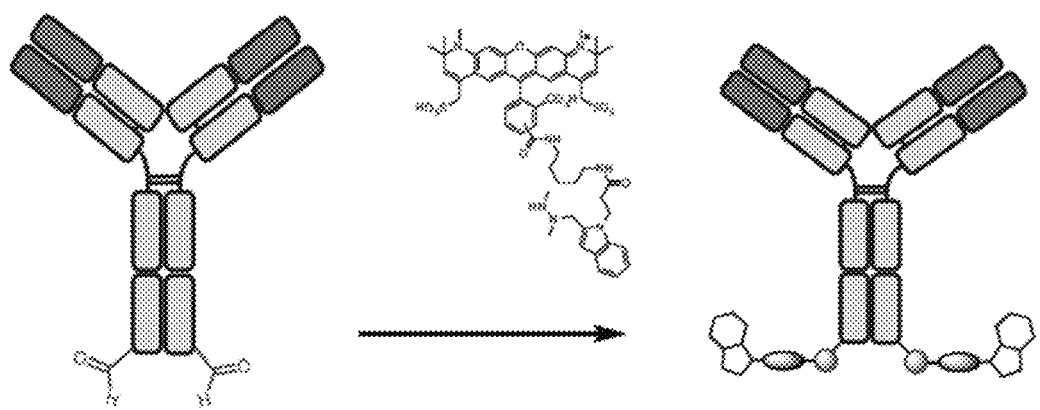
Figure 2:
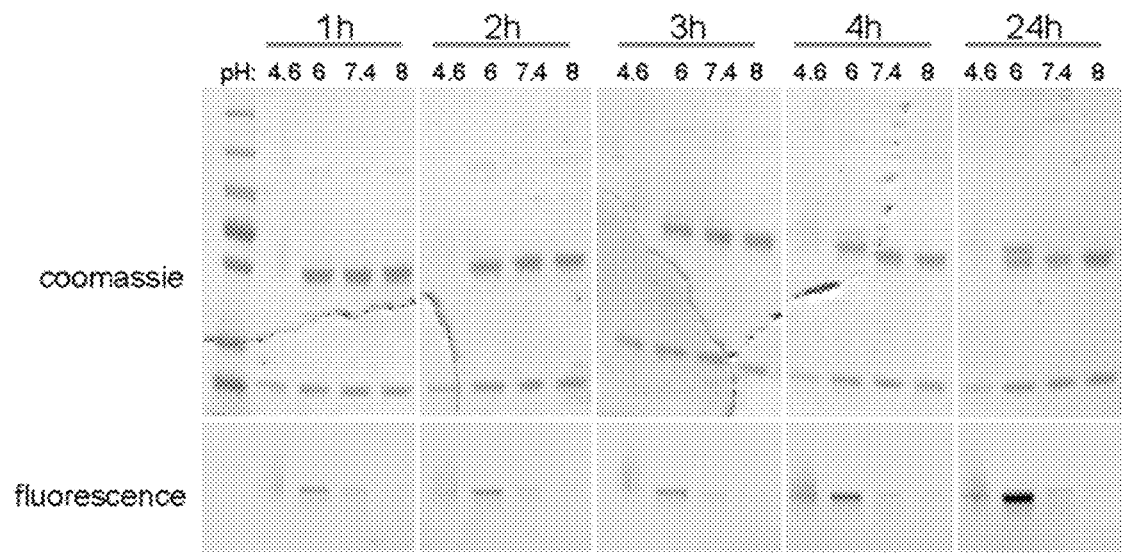

Results of the conjugation reaction are shown in FIG. 2, panels A-C, which shows conjugation of HIPS-AF594 to aldehyde-tagged antibody conjugated over a range of pH conditions. FIG. 2, panel A, shows a reaction scheme for the synthesis of the functionalized detectable label. FIG. 2, panel B, shows a schematic of the conjugation reaction of the functionalized detectable label to the antibody. FIG. 2, panel C, shows images of SDS-PAGE gels, which were used to analyze the conjugate. The presense of conjugate was determined by fluorescence imaging.

Example 2

Stability of Antibody-Detectable Label Conjugate

Figure 3:
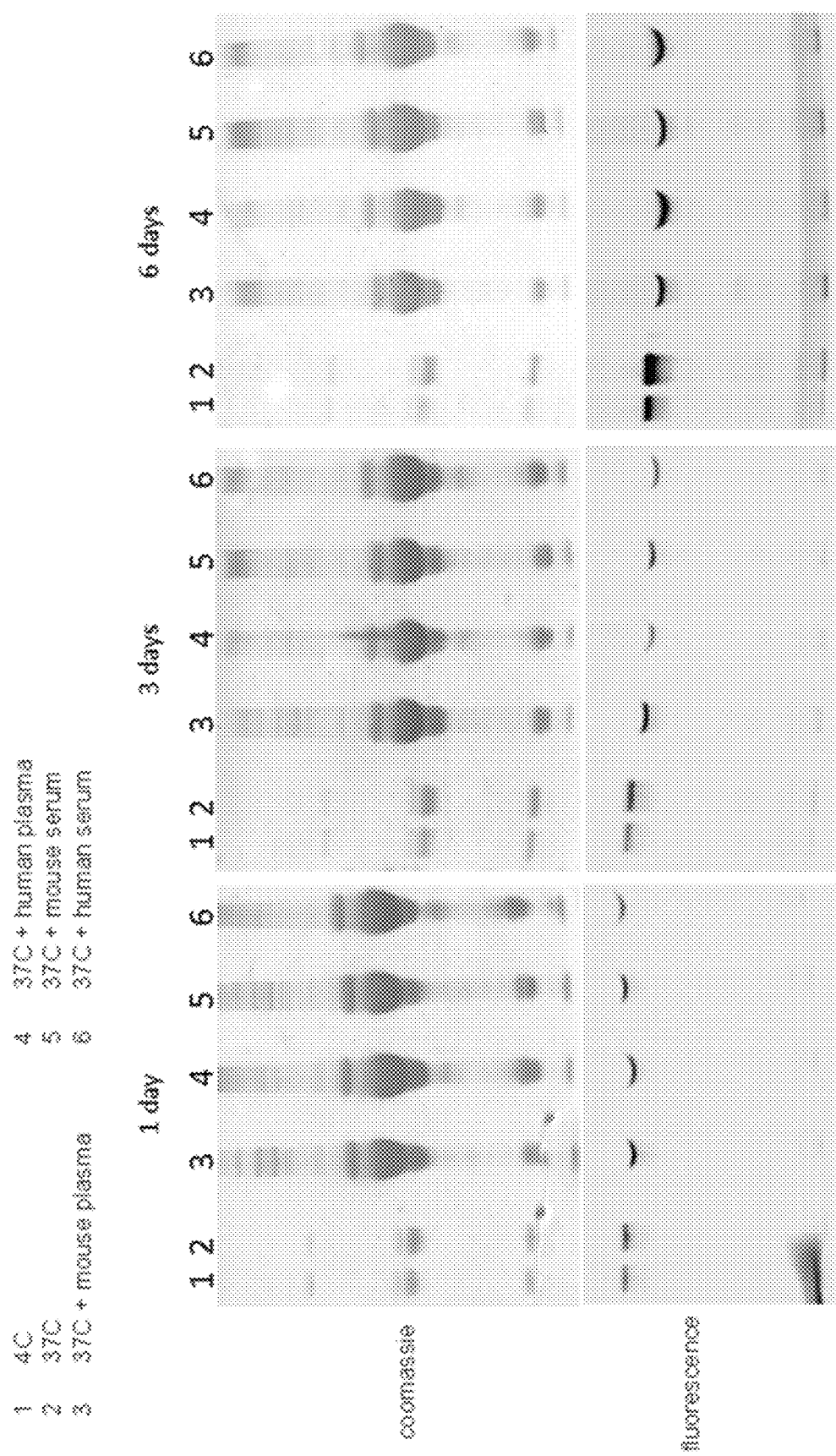
FIG. 3 shows images of SDS-PAGE gels showing the stability of an antibody-detectable label conjugate over a 6 day time period, according to embodiments of the present disclosure.

HIPS-AF594 (Compound 80, above) (42.4 drug:aldehyde equivalents) was reacted with 5.9 µM aldehyde-tagged IgG antibody for 16 hr at 37° C. in 128 mM sodium chloride and 50 mM sodium citrate pH 6. The unreacted HIPS-AF594 was removed from the reaction mixture by size exclusion chromatography. The resulting antibody-fluorophore conjugate was incubated at 4° C. or 37° C. in either plasma or serum (both human and mouse) for 1, 3 or 6 days. SDS-PAGE was used to analyze the conjugate. The presence of conjugate was determined by fluorescence imaging. As shown in FIG. 3, no free dye was observed in either case and the conjugate had not decomposed.

Results of the conjugation reaction are shown in FIG. 3, which shows images of SDS-PAGE gels showing the stability of an antibody-detectable label conjugate over a 6 day time period.

Example 3

Conjugation of HIPS-6PEG-Maytansine to an Aldehyde-Tagged Antibody

HIPS-6PEG-Maytansine (Compound 190, above; 231.5 drug:aldehyde equivalents) was reacted with 5.4 uM aldehyde-tagged antibody (A) in PBS with 50 mM sodium citrate pH 6 and 10% DMA at 37° C. The reaction mixture was analyzed after 48 hours.

Figure 4:
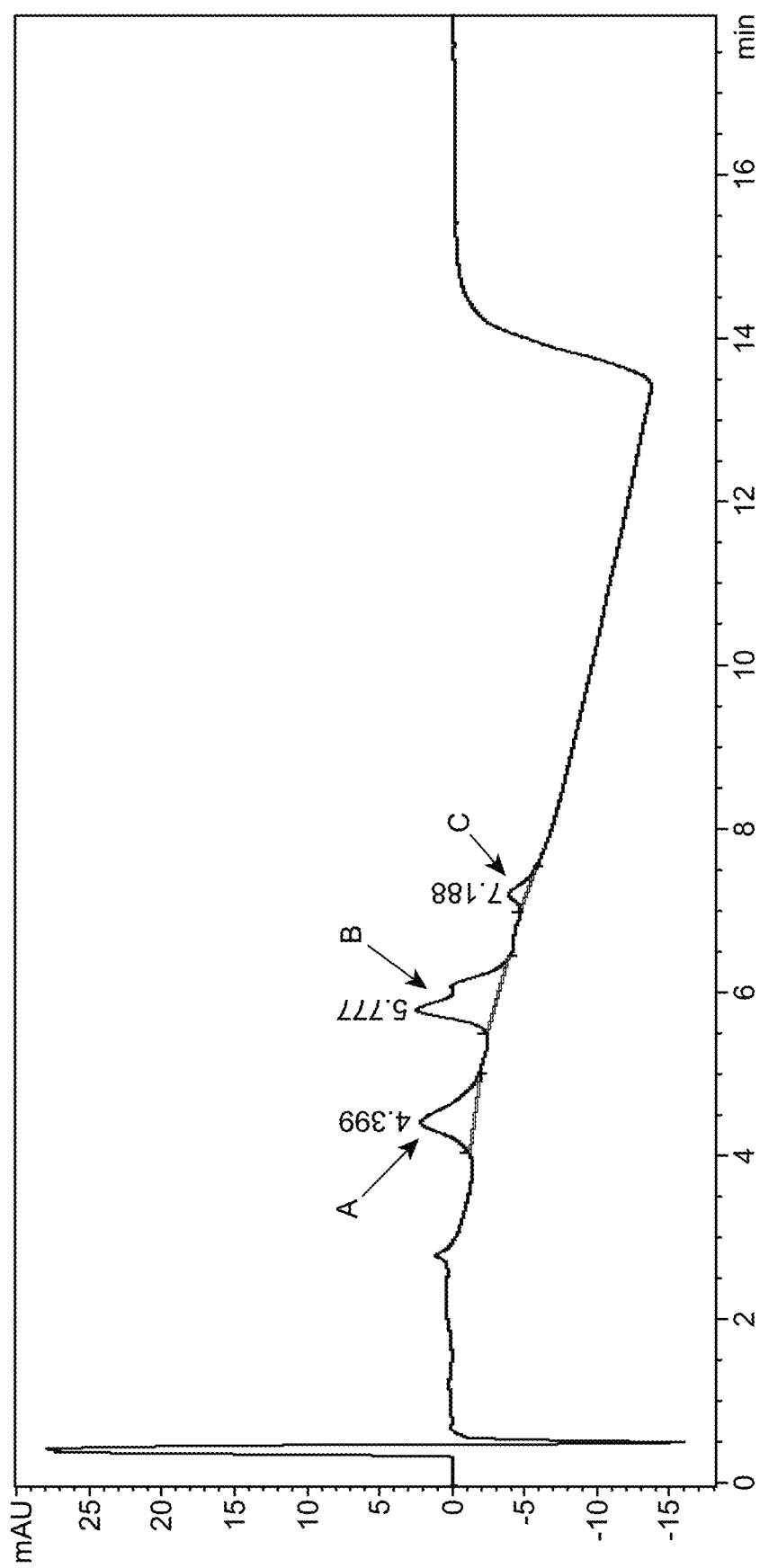
FIG. 4 shows a hydrophobic interaction column (HIC) trace of aldehyde-tagged antibody conjugated to HIPS-6PEG-Maytansine, according to embodiments of the present disclosure.

Results are shown in FIG. 4, which shows a hydrophobic interaction column (HIC) trace of the aldehyde-tagged antibody conjugated to HIPS-6PEG-Maytansine. The unconjugated (A), mono-conjugate (B), and di-conjugate (C) protein conjugate were observed.

Additional compounds were synthesized as described below.

General Synthetic Methods

All reagents were obtained from Sigma-Aldrich, Acros, or TCI and used without further purification except piperidine, which was dried over $CaH_2$ and distilled. Anhydrous solvents were obtained from commercial sources in sealed bottles. Column chromatography was performed with a Biotage Isolera Prime chromatograph. High-pressure liquid chromatography was performed on an Agilent 1100 chromatograph equipped with an Agilent Poroshell 120 column (4.6×150 mm), with UV absorption monitored at 205 nm.

NMR spectra were acquired on a Bruker 400 MHz spectrometer by Emeryville Pharmaceutical Services. $^1$H NMR spectra were referenced to residual $CHCl_3$ (7.26 ppm), $CD_2HCN$ (1.94 ppm), or $CD_2HOD$ (3.31 ppm). $^{13}$C NMR spectra were referenced to $CDCl_3$ (77.16 ppm), $CD_3CN$ (1.32 ppm), or $CD_3OD$ (49.00 ppm). NMR spectra were processed using MestReNova (Mestrelab Research S.L.). High-resolution ESI mass spectra of small molecules were obtained at the UC Berkeley Mass Spectrometery Facility on a Thermo LTQ Orbitrap mass spectrometer.

HIPS ligation reagent (Compound 4) was synthesized as illustrated in Scheme 4, below:

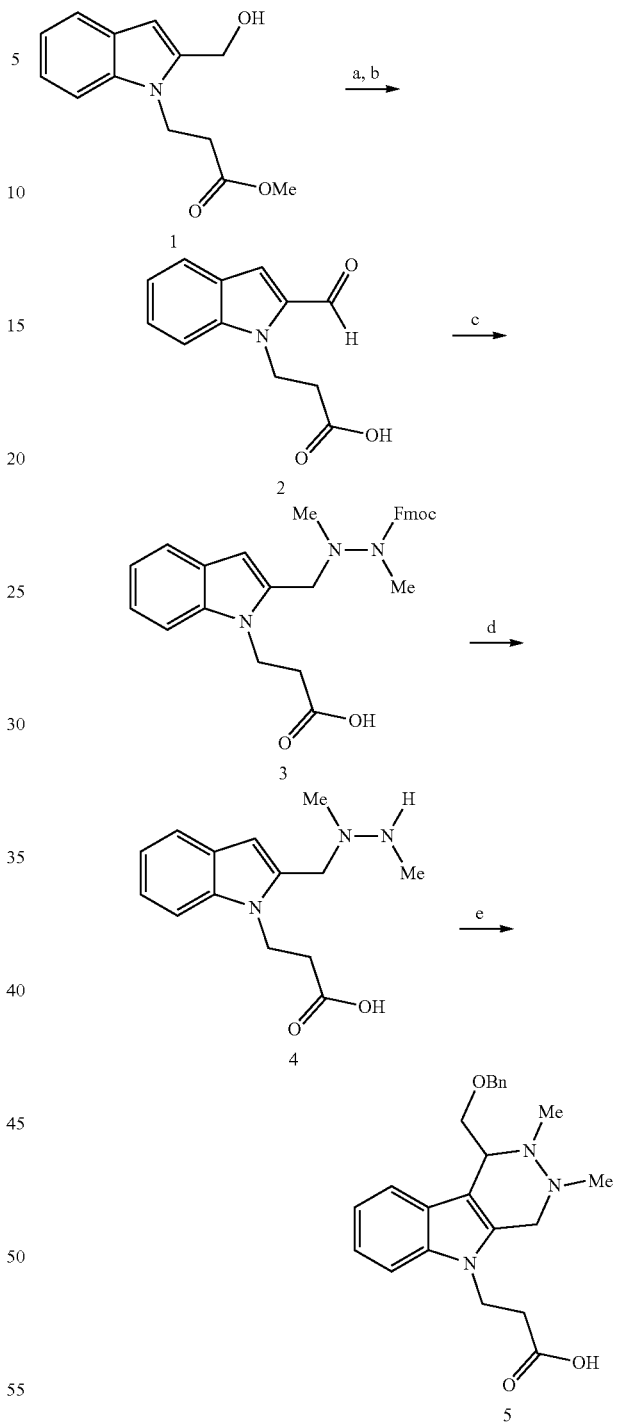

Synthesis of Methyl 3-(2-formyl-1H-indol-1-yl)propanoate (1)

Compound 1 was synthesized as follows. Dess-Martin periodinane (5.195 g, 12.25 mmol, 1.09 equiv) was suspended in a mixture of dichloromethane (20 mL) and pyridine (2.70 mL, 33.5 mmol, 3.0 equiv). After 5 min, the resulting white suspension was transferred to a solution of methyl 3-(2-(hydroxymethyl)-1H-indol-1-yl)propanoate (2.611 g, 11.19 mmol) in dichloromethane (10 mL), resulting in a red-brown suspension. After 1 h, the reaction was quenched with sodium thiosulfate (10% aqueous solution, 5 mL) and sodium bicarbonate (saturated aqueous solution, 5 mL). The aqueous layer was extracted with dichloromethane (3×20 mL), and then dried over sodium sulfate, filtered, and concentrated to a brown oil. Purification by silica gel chromatography (5-50% ethyl acetate in hexanes) yielded the product as a colorless oil (2.165 g, 9.363 mmol, 84%). $^1$H NMR (400 MHz, CDCl$_3$) δ 9.87 (s, 1H), 7.73 (dt, J=8.1, 1.0 Hz, 1H), 7.51 (dd, J=8.6, 0.9 Hz, 1H), 7.45-7.40 (m, 1H), 7.29 (d, J=0.9 Hz, 1H), 7.18 (ddd, J=8.0, 6.9, 1.0 Hz, 1H), 4.84 (t, J=7.2 Hz, 2H), 3.62 (s, 3H), 2.83 (t, J=7.2 Hz, 2H). $^{13}$C NMR (101 MHz, CDCl$_3$) δ 182.52, 171.75, 140.12, 135.10, 127.20, 126.39, 123.46, 121.18, 118.55, 110.62, 51.83, 40.56, 34.97. HRMS (ESI) calcd for C$_{13}$H$_{13}$NO$_3$Na [M+Na]$^+$: 254.0793; found: 254.0786.

Synthesis of 3-(2-formyl-1H-indol-1-yl)propanoic acid (2)

Compound 2 was synthesized from Compound 1 as follows. To a solution of Compound 1 (306 mg, 1.32 mmol) dissolved in dioxane (18 mL) was added LiOH (2 M aqueous solution, 992 µL, 1.98 mmol, 1.5 equiv). After 1 h, hydrochloric acid (1 M aqueous solution) was added dropwise to give a solution with pH=5. The solution was concentrated and the resulting pale brown oil was dissolved in ethyl acetate (20 mL) and washed with acetic acid (5% aqueous solution, 10 mL), water (10 mL), and brine (10 mL). The organic layer was dried over sodium sulfate, filtered, and concentrated to a pale brown oil. Purification by silica gel chromatography (5-50% ethyl acetate in hexanes with 0.1% acetic acid) yielded the product as a pale yellow solid (290 mg, 1.34 mmol, quantitative). $^1$H NMR (400 MHz, CDCl$_3$) δ 9.89 (s, 1H), 7.76 (dt, J=8.1, 0.9 Hz, 1H), 7.53 (dd, J=8.6, 0.9 Hz, 1H), 7.48-7.43 (m, 1H), 7.33 (d, J=0.8 Hz, 1H), 7.21 (ddd, J=8.0, 6.9, 1.0 Hz, 1H), 4.85 (t, J=7.2 Hz, 2H), 2.91 (t, J=7.2 Hz, 2H). $^{13}$C NMR (101 MHz, CDCl$_3$) δ 182.65, 176.96, 140.12, 135.02, 127.33, 126.42, 123.53, 121.27, 118.76, 110.55, 40.19, 34.82. HRMS (ESI) calcd for C$_{12}$H$_{10}$NO$_3$ [M−H]$^−$: 216.0666; found: 216.0665.

Synthesis of 3-(2-((2-(((9H-fluoren-9-yl)methoxy) carbonyl)-1,2-dimethylhydrazinyl)methyl)-1H-indol-1-yl)propanoic acid (3)

Compound 3 was synthesized from Compound 2 as follows. To a solution of Compound 2 (1.193 g, 5.492 mmol) and FmocN(Me)NHMe (2.147 g, 7.604 mmol, 1.38 equiv) in 1,2-dichloroethane (anhydrous, 25 mL) was added sodium triacetoxyborohydride (1.273 g, 6.006 mmol, 1.09 equiv). The resulting yellow suspension was stirred for 2 h and then quenched with sodium bicarbonate (saturated aqueous solution, 10 mL), followed by addition of hydrogen chloride (1 M aqueous solution) to pH 4. The organic layer was separated, and the aqueous layer was extracted with dichloromethane (5×10 mL). The pooled organic extracts were dried over sodium sulfate, filtered, and concentrated to an orange oil. Purification by C18 silica gel chromatography (20-90% acetonitrile in water) yielded 3 as a waxy pink solid (1.656 g, 3.425 mmol, 62%). $^1$H NMR (400 MHz, CDCl$_3$) δ 7.76 (d, J=7.4 Hz, 2H), 7.70-7.47 (br m, 3H), 7.42-7.16 (br m, 6H), 7.12-7.05 (m, 1H), 6.37 (s, 0.6H), 6.05 (s, 0.4H), 4.75-4.30 (br m, 4H), 4.23 (m, 1H), 4.10 (br s, 1H), 3.55 (br d, 1H), 3.11-2.69 (m, 5H), 2.57 (br s, 2H), 2.09 (br s, 1H). $^{13}$C NMR (101 MHz, CDCl$_3$) δ 174.90, 155.65, 143.81, 141.42, 136.98, 134.64, 127.75, 127.48, 127.12, 124.92, 122.00, 120.73, 120.01, 119.75, 109.19, 103.74, 67.33, 66.80, 51.39, 47.30, 39.58, 39.32, 35.23, 32.10. HRMS (ESI) calcd for C$_{29}$H$_{30}$N$_3$O$_4$ [M+H]$^+$: 484.2236; found: 484.2222.

Synthesis of Piperidinium 3-(2-((1,2-dimethylhydrazinyl)methyl)-1H-indol-1-yl)propanoate (4)

Compound 4 was synthesized from Compound 3 as follows. Indole 3 (64.2 mg, 133 µmol) was dissolved in a solution of piperidine in N,N-dimethylacetamide (20% v/v, 1.31 mL, 2.65 mmol, 20.0 equiv). After 20 min, the solution was purified by C18 silica gel chromatography (0-100% acetonitrile in water). The product was isolated as a colorless oil (28.4 mg, 82.0 µmol, 62%). $^1$H NMR (400 MHz, 7:5 D$_2$O:CD$_3$CN) δ 7.84 (d, J=7.9 Hz, 1H), 7.76 (d, J=8.3 Hz, 1H), 7.49 (m, 1H), 7.36 (m, 1H), 6.73 (s, 1H), 4.73-4.69 (m, 2H), 4.25 (s, 2H), 3.36-3.29 (m, 4H), 2.86-2.80 (m, 2H), 2.78 (s, 3H), 2.67 (s, 3H), 1.99-1.95 (m, 4H), 1.88-1.83 (m, 2H). $^{13}$C NMR (151 MHz, 7:5 D$_2$O:CD$_3$CN) δ 179.80, 137.61, 135.78, 128.40, 122.59, 121.29, 120.50, 110.94, 103.70, 53.86, 45.32, 42.79, 41.43, 38.64, 33.95, 23.07, 22.41, 1.32. HRMS (ESI) calcd for C$_{14}$H$_{20}$N$_3$O$_2$ [M−piperidine+H]$^+$: 262.1556; found: 262.1547.

Synthesis of 3-(1-((benzyloxy)methyl)-2,3-dimethyl-3,4-dihydro-1H-pyridazino[4,5-b]indol-5(2H)-yl)propanoic acid (5)

Compound 4 was reacted with benzyloxyacetaldehyde, which was chosen as a model small molecule aldehyde for its UV absorption and aqueous solubility properties, to produce the azacarboline product (Compound 5). To a solution of Compound 4 (16.2 mg, 46.8 µmol) in aqueous acetonitrile (1:3 water:acetonitrile, 800 µL) was added benzyloxyacetaldehyde (7.23 µL, 51.5 µmol, 1.10 equiv). After 1 h, the solution was purified by C18 silica gel chromatography (0-100% acetonitrile in water with 0.1% acetic acid). Toluene was added to the eluent to aid in removal of residual acetic acid, and the product was isolated as a pale brown oil (16.2 mg, 41.2 µmol, 88%). $^1$H NMR (400 MHz, CDCl$_3$) δ 7.41 (d, J=7.8 Hz, 1H), 7.38-7.34 (m, 2H), 7.34-7.30 (m, 3H), 7.18-7.15 (m, 2H), 7.08-7.05 (m, 1H), 4.65 (d, J=12.4 Hz, 1H), 4.58 (d, J=12.4 Hz, 1H), 4.28-4.18 (m, 2H), 4.10 (m, 1H), 3.91 (t, J=9.0 Hz, 1H), 3.81 (s, 1H), 3.76-3.64 (m, 2H), 2.69 (t, J=6.8 Hz, 2H), 2.63 (s, 3H), 2.39 (s, 3H). $^{13}$C NMR (151 MHz, CDCl$_3$) δ 175.08, 138.74, 136.27, 131.75, 128.42, 127.92, 127.60, 126.61, 121.43, 119.61, 118.74, 109.33, 105.41, 73.46, 71.94, 61.61, 44.16, 41.33, 39.19, 34.98, 31.17. HRMS (ESI) calcd for C$_{23}$H$_{28}$N$_3$O$_3$ [M+H]$^+$: 394.2131; found: 394.2120.

Synthesis of Fmoc-HIPS-PFP

Fmoc-HIPS-PFP was synthesized as follows. To a solution of Fmoc-HIPS acid (Compound 4) (1.4673 g, 3.0344 mmol) and pentafluorophenol (608.1 mg, 3.304 mmol, 1.09 equiv) in ethyl acetate (anhydrous, 10 mL) at 0° C. was added a solution of N,N'-dicyclohexylcarbodiimide (684.0 mg, 3.315 mmol, 1.09 equiv) in ethyl acetate (anhydrous, 15 mL). A white precipitate began to form and after 5 min the solution was allowed to warm to room temperature. After 90 min, the suspension was cooled to 0° C. and filtered through Celite; the filter cake was washed with cold ethyl acetate (5 mL). The filtrate was washed with water (4×10 mL) and brine (10 mL), dried over sodium sulfate, filtered, and concentrated to a pale yellow solid (1.979 g, 3.046 mmol, 100%). This material was used in subsequent reactions without further purification.

Synthesis of Fmoc-HIPS-AF488

Fmoc-HIPS-AF488 was synthesized as follows. To a solution of Fmoc-HIPS-PFP (3.0 mg) and Alexa Fluor 488 (AF488) cadaverine (1 mg, 1.6 µmol) in N,N-dimethylformamide (0.2 mL) was added sodium carbonate (100 mM aqueous solution, 31.2 µL, 3.12 □mol). After 2 h, the reaction mixture was concentrated to a red-orange oil which was purified by C18 silica gel chromatography ($H_2O$/MeCN). The product was isolated as a red solid (1.7 mg, 1.54 µmol, 99%). HRMS (ESI) calcd for $C_{55}H_{52}N_7O_{13}S_2$ [M–Na]$^-$: 1082.3070; found: 1082.3064.

Synthesis of HIPS-AF488 Ligation Reagent (Compound 9)

HIPS-AF488 ligation reagent (Compound 9) was synthesized as follows. Fmoc-HIPS-AF488 (1.7 mg, 1.54 µmol) was dissolved in a solution of dioxane:MeOH:2 M aqueous NaOH (30:9:1, 94 µL, 4.7 µmol NaOH, 3.1 equiv NaOH). After 30 min, the pale blue reaction mixture was quenched with acetic acid (5% aqueous solution, 50 µL), resulting in a fluorescent green solution which was concentrated to a red solid. The product was purified by C18 silica gel chromatography and further purified by HPLC on an Agilent Zorbax 300SB-C18 column (9.4×250 mm). The product was isolated as a red solid (1.0 mg, 1.16 µmol, 75%). HRMS (ESI) calcd for $C_{40}H_{42}N_7O_{11}S_2$[M–Na]$^-$: 860.2389; found: 860.2387.

Example 4

Reactivity of HIPS Ligation Reagent (Compound 4)

Figure 5:
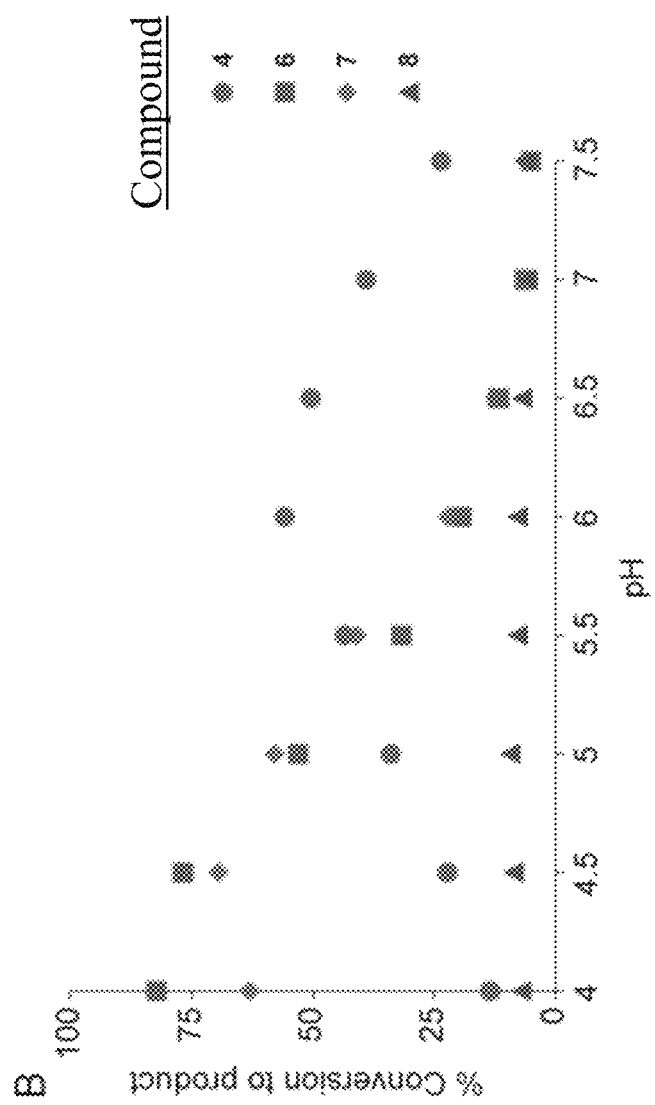
FIG. 5, panels A and B, show kinetics of condensation reactions of model amine compounds with benzyloxyacetaldehyde, according to embodiments of the present disclosure.
Figure 5:
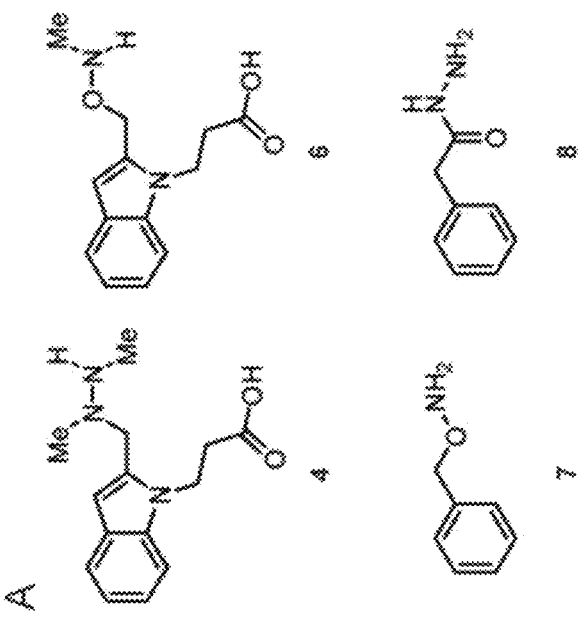
Figure 6:
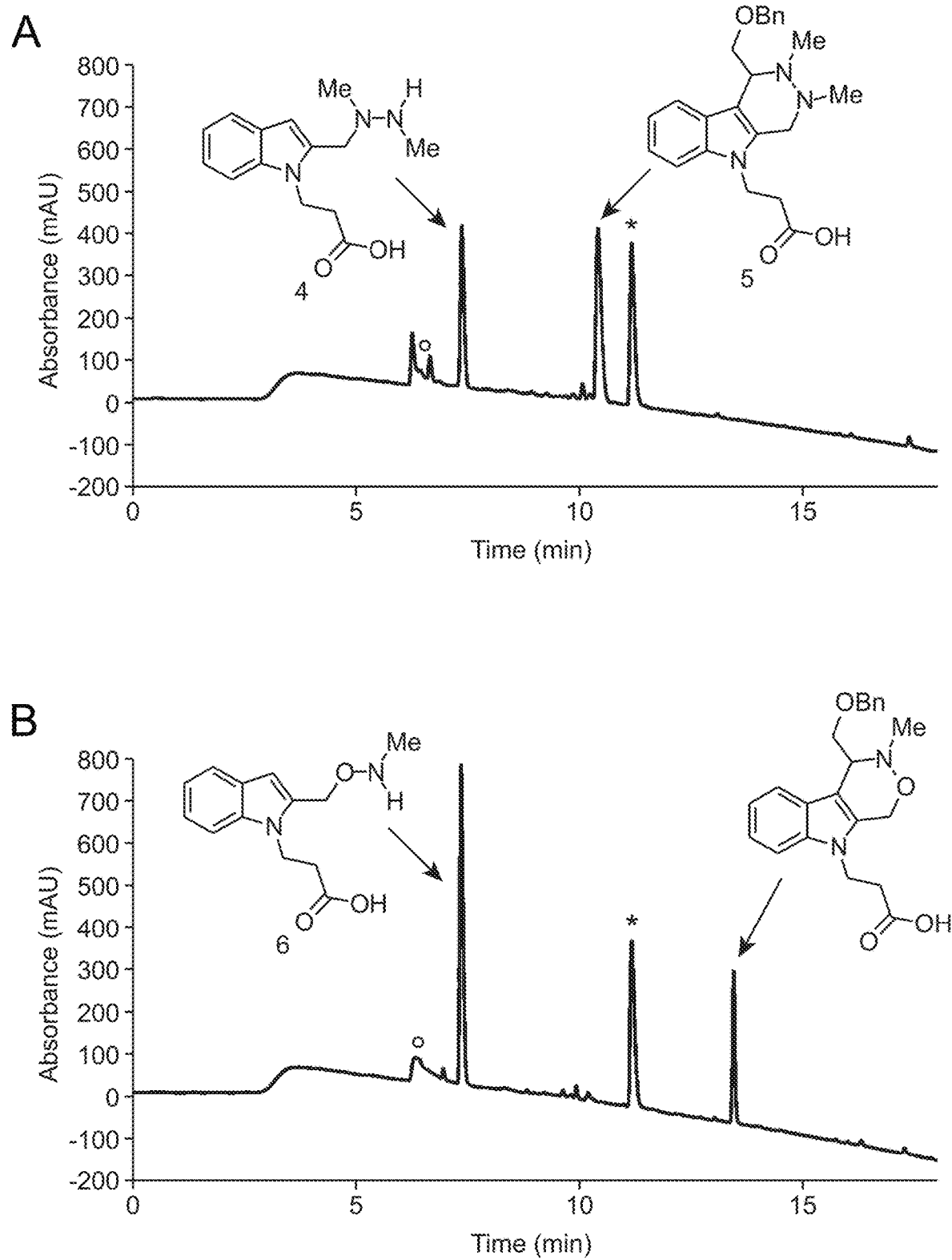
FIG. 6, panels A-D, show HPLC traces for small molecule kinetics experiments, showing reaction of Compound 4 (FIG. 6, panel A), Compound 6 (FIG. 6, panel B), Compound 7 (FIG. 6, panel C), and Compound 8 (FIG. 6, panel D) with benzyloxyacetaldehyde after 2 h at pH 6.0, according to embodiments of the present disclosure. Benzyloxyacetaldehyde (°) and bromocresol green(*), which was added as an internal standard, are marked on each chromatogram.
Figure 6:
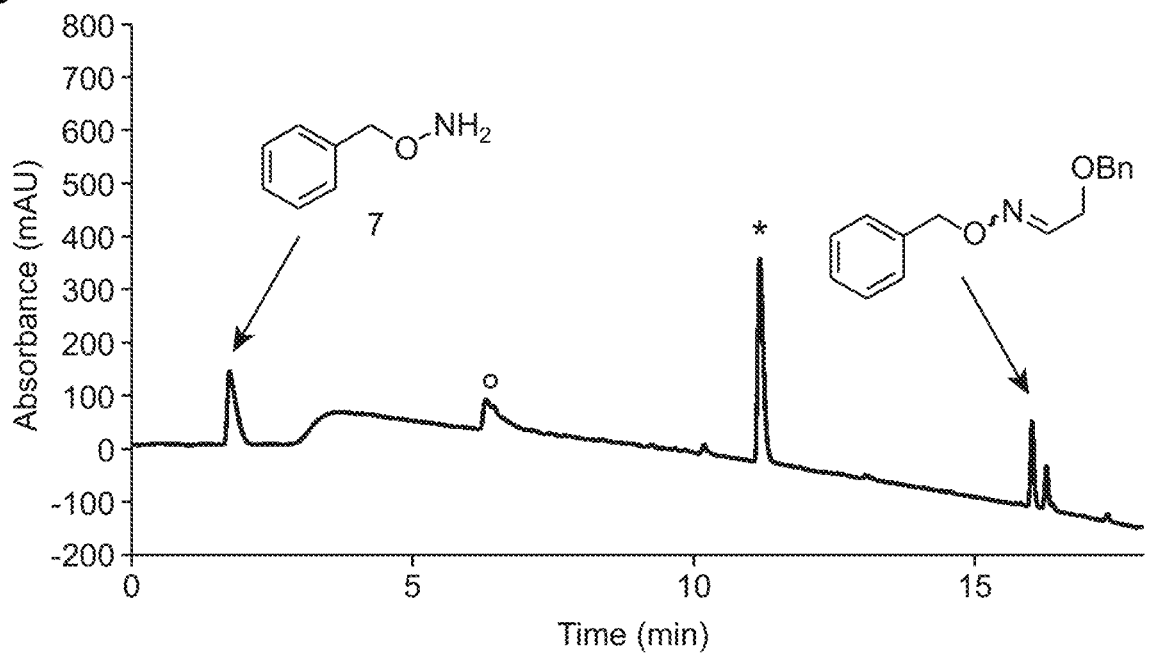
Figure 6:
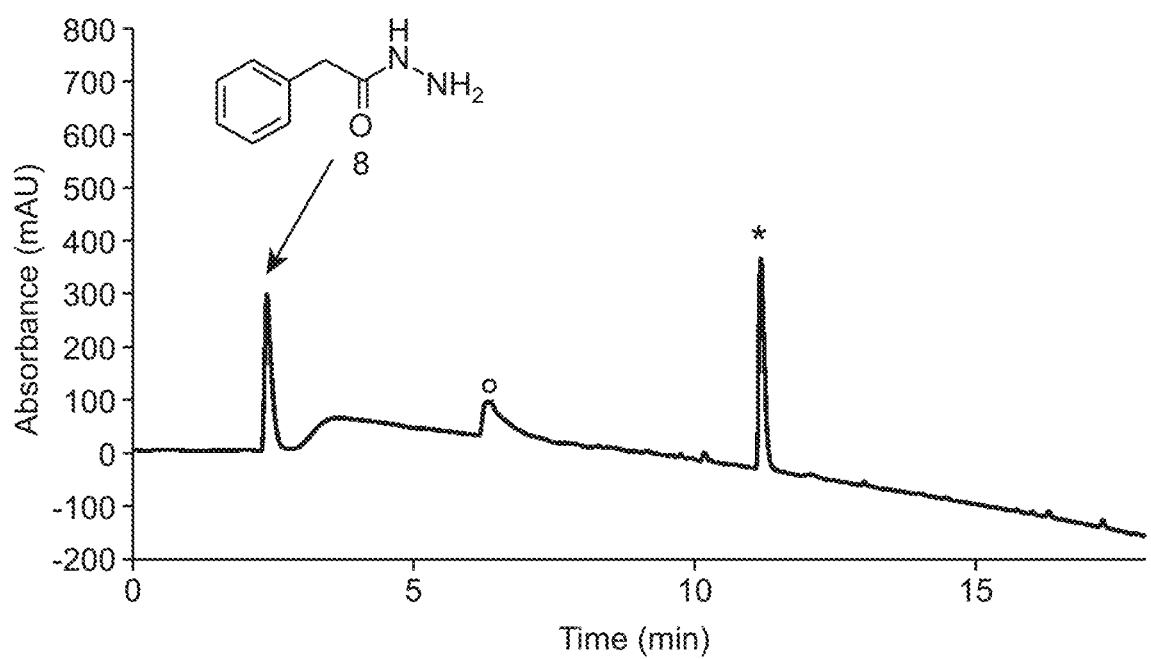

Experiments were performed to study the reactivity of HIPS reagent (Compound 4) relative to model aminooxy, hydrazide, and Pictet-Spengler ligation reagents with benzyloxyacetaldehyde (FIG. 5, panels A and B, and FIG. 6, panels A-D).

Experimental Protocol for HPLC Kinetics Assay:

Reaction mixtures contained amine 4, 6, 7, or 8 (50 µM), benzyloxyacetaldehyde (50 µM), bromocresol green (10 µM), and buffer (10 mM) in a 120 µL aqueous solution containing 6.7% MeCN, which was present to solubilize the stock solution (1 mM) of benzyloxyacetaldehyde. After 2 h at room temperature, a 100 µL aliquot was analyzed by HPLC, employing a gradient of 10 to 100% acetonitrile in water over 18 min.

As described above, buffered solutions containing 50 µM amine and aldehyde were incubated at room temperature for 2 h prior to analysis by HPLC. Within a pH range encompassing conditions commonly used for aldehyde and ketone bioconjugation reactions, aminooxy indole 6 (a model Pictet-Spengler ligation reagent) and model aminooxy compound 7 reacted more quickly under acidic conditions. The reaction of hydrazide 8 did not proceed appreciably under any conditions, which may be due to the low equilibrium constant for hydrazone formation. Above pH 6, indole 4 had a higher % conversion to product than the other amine nucleophiles, which indicated that the HIPS ligation may be useful for labeling proteins near neutral pH. A bell-shaped pH-rate curve was observed for the reaction with Compound 4; the decreased reaction rate at lower pH may be due to rate-limiting carbonyl addition due to protonation of the hydrazine moiety of Compound 4, since trialkylhydrazines such as the one in Compound 4 (pKa~6.56) are more basic than O-alkylaminooxy moieties such as the one in Compound 6 (pKa~4.60).

Example 5

Conjugation of Compound 4 to FGly-MBP

Experiments were performed to selectively label an aldehyde-containing protein (FGly-MBP) with Compound 4 at near-neutral pH.

Experimental Protocol for Conjugation of 4 to FGly-MBP:

Indole 4 (1 mM) and FGly-MBP (1.41 mg/mL) were combined in sodium citrate buffer (50 mM, pH 5.0) and incubated at 37° C. for 24 h. Excess Compound 4 was removed by buffer exchange into PBS in a centrifugal concentrator (Amicon, 10 kDa MWCO) and the sample was then treated with trypsin (1.1 ug, 2 wt %) and incubated at 37° C. for 24 h. The peptides were desalted using a C18 column (The Nest Group), eluting with 70% acetonitrile, 1% formic acid in water. The eluent was concentrated by centrifugal evaporation and then analyzed by nano-LC/MS at the U.C. Berkeley QB3/Chemistry Mass Spectrometry Facility on a Waters Q-Tof premier electrospray ionization time of flight mass spectrometer connected to a Waters nanoAcquity UPLC.

An aldehyde-tagged maltose binding protein (FGly-MBP), which is a variant of MBP that bears a $C_\alpha$-formylglycine (FGly) residue near its C terminus, was used as a substrate. As described previously, the formylglycine residue was installed by inclusion of the short peptide sequence LCTPSR at the C-terminus of the protein. Coexpression of MBP with the *Mycobacterium tuberculosis* formylglycine generating enzyme resulted in cotranslational oxidation of the consensus sequence cysteine residue to formylglycine, which was selectively reactive with the hydrazine-containing reagent 4. FGly-MBP was reacted with indole 4 overnight and then the resulting conjugate was trypsinized. Analysis of the tryptic digest by ESI-MS showed that Compound 4 reacted with the FGly residue.

Example 6

Protein Labeling Experiments

Experiments were performed to determine the speed of the HIPS ligation under mild reaction conditions by assessing labeling kinetics on proteins at pH 6.0.

Experimental Protocol for Protein Labeling Experiments:

Reaction mixtures contained fluorophore 9, 10, 11, or 12 (400 µM) and protein (MBP, 0.67 mg/mL; α-HER2, 0.37 mg/mL; or Mb, 0.51 mg/mL) in sodium phosphate buffer (100 mM, pH 6.0). After 2 h at 37° C., the reaction was stopped by adding Tris-Cl to pH 8.5-9 and immediately analyzed by SDS-PAGE. Since the free fluorophores coeluted with and obscured Mb, the protein was wet transferred to a nitrocellulose membrane to remove free fluorophore prior to fluorescence imaging, and protein loading was assessed using Ponceau S.

Figure 7:
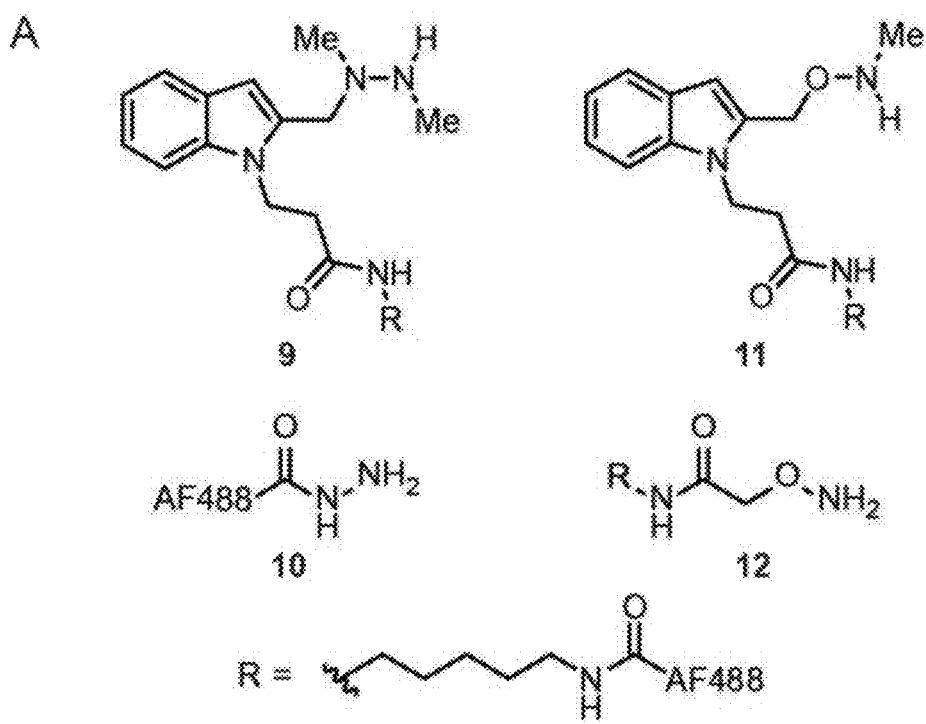
FIG. 7, panels A-D, show fluorescent labeling of aldehyde-bearing proteins with the HIPS ligation and other common aldehyde bioconjugation chemistries, according to embodiments of the present disclosure.
Figure 7:
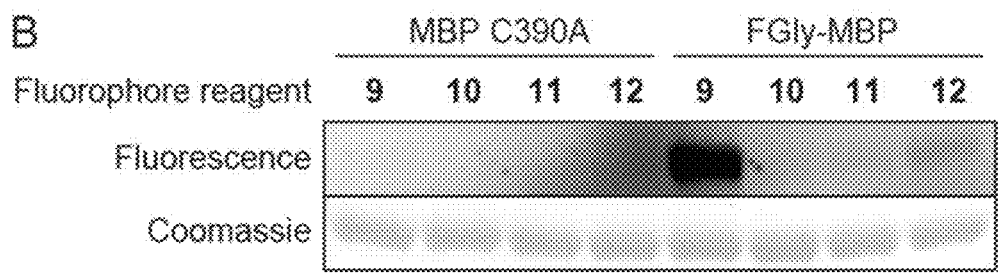
Figure 7:
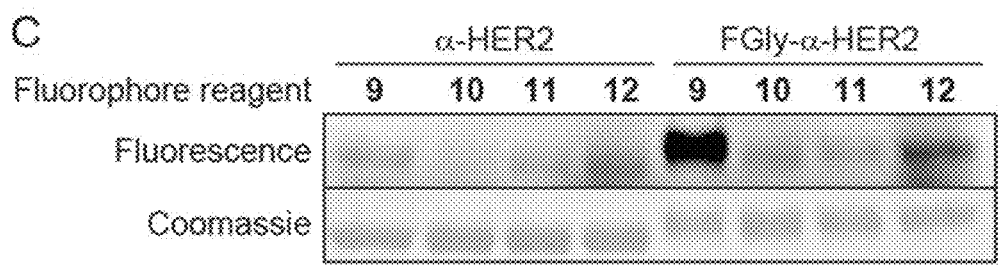
Figure 7:
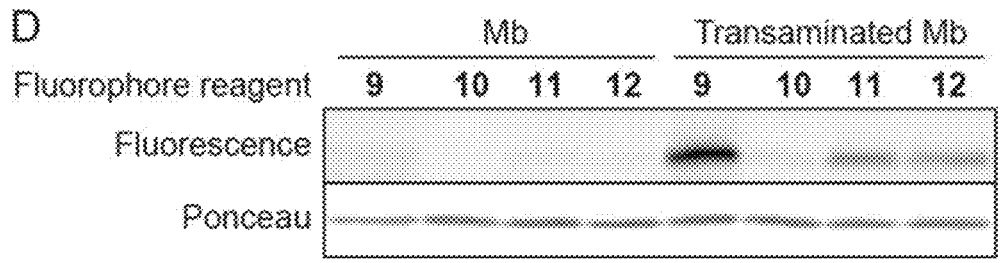

To facilitate the analysis of protein conjugation experiments by SDS-PAGE, a fluorophore-functionalized HIPS indole (Compound 9) was prepared by coupling Compound 3 with Alexa Fluor 488 cadaverine followed by Fmoc deprotection with piperidine. In these experiments, the relative conjugation efficiencies of HIPS reagent 9 were compared to both the commercially-available AF488 hydrazide (Compound 10) and the aminooxy reagent (Compound 11). This experimental design allowed for a comparison of the HIPS ligation to the previously-reported Pictet-Spengler ligation as well as commercially-available aminooxy AF488 (Compound 12, FIG. 7, panel A). The relative labeling of two formylglycine-bearing proteins was assessed at pH 6.0: FGly-MBP and FGly-α-HER2, a variant of the therapeutic monoclonal antibody Herceptin that contains a formylglycine residue at the C-terminus of each of its heavy chains. To show the generality of the method with an aldehyde other than formylglycine, the labeling of chemically modified myoglobin (Mb) containing an N-terminal glyoxamide installed by pyridoxal phosphate-mediated transamination was also assessed. In all three cases, treatment of the aldehyde-functionalized protein with 400 µM of the fluorophore reagents 9-12 at pH 6.0 for 2 h showed that labeling with HIPS reagent 9 was faster than labeling with the aminooxy and hydrazido-fluorophore panel (FIG. 7, panels B-D). Control experiments with the FGly-MBP C390A mutant (which lacked the requisite cysteine residue for conversion to formylglycine), α-HER2 without the aldehyde tag sequence, and wild-type Mb, all of which lack aldehyde functionality, showed negligible labeling with Compound 9. The experiment using FGly-α-HER2 demonstrated a method for the site-specific conjugation of a monoclonal antibody with a small molecule under mild conditions.

Example 7

Hydrolytic Stability Experiments

Experiments were performed to determine the hydrolytic stability of the linkage on FGly-MBP relative to oximes, which are typically hydrolytically stable linkages for aldehydes and ketones in bioconjugation chemistry.

Experimental Protocol for MBP-AF488 Conjugate Hydrolysis ELISA

Preparation of MBP-AF488 Conjugates:

Fluorophore 9 or 12 (545 µM) and FGly-MBP (1.61 mg/mL, 40 jag) were combined in sodium citrate buffer (45 mM, pH 4.5). After 18 h at 37° C., the proteins were purified away from free fluorophore by ion-exchange chromatography (GE HiTrap SPXL, 5 mM to 1 M NaCl in 5 mM sodium citrate pH 5.5). Conjugation of the AF488 dye was verified by UV-vis spectroscopy.

Incubation of Conjugates in Human Plasma:

A solution of MBP-AF488 conjugate (10 jag/mL) in human plasma (0.98×) was incubated at 37° C. for 5 d. Aliquots were withdrawn at 10-14 h intervals and diluted with 1% BSA in PBS to 10 ng/mL; the resulting solutions were immediately frozen at −80° C. until analysis by ELISA.

ELISA:

A 96-well microtiter plate (Nunc Maxisorp) was coated with α-MBP (2.5 µg/mL in PBS, Abcam) at 4° C. overnight. The wells were washed twice with PBST, then incubated with BSA (1% in PBS) for 2 h. The wells were washed twice with PBST, then incubated with MBP-AF488 conjugate solutions (10 ng/mL). After 1 h, the wells were washed four times with PBST, then incubated with rabbit α-AF488 IgG (Invitrogen, 1:5000) for 1 h. The wells were washed four times with PBST, then incubated with HRP-conjugated donkey α-rabbit IgG (Jackson ImmunoResearch, 1:10000) for 1 h. After washing the wells four times with PBST, tetramethylbenzidine and hydrogen peroxide (Pierce TMB kit) were added and the reaction was quenched by addition of 1 volume of $H_2SO_4$ (2 M) after 15 min. Absorption was read at 450 nm on a plate reader (SpectraMax M5).

Figure 8:
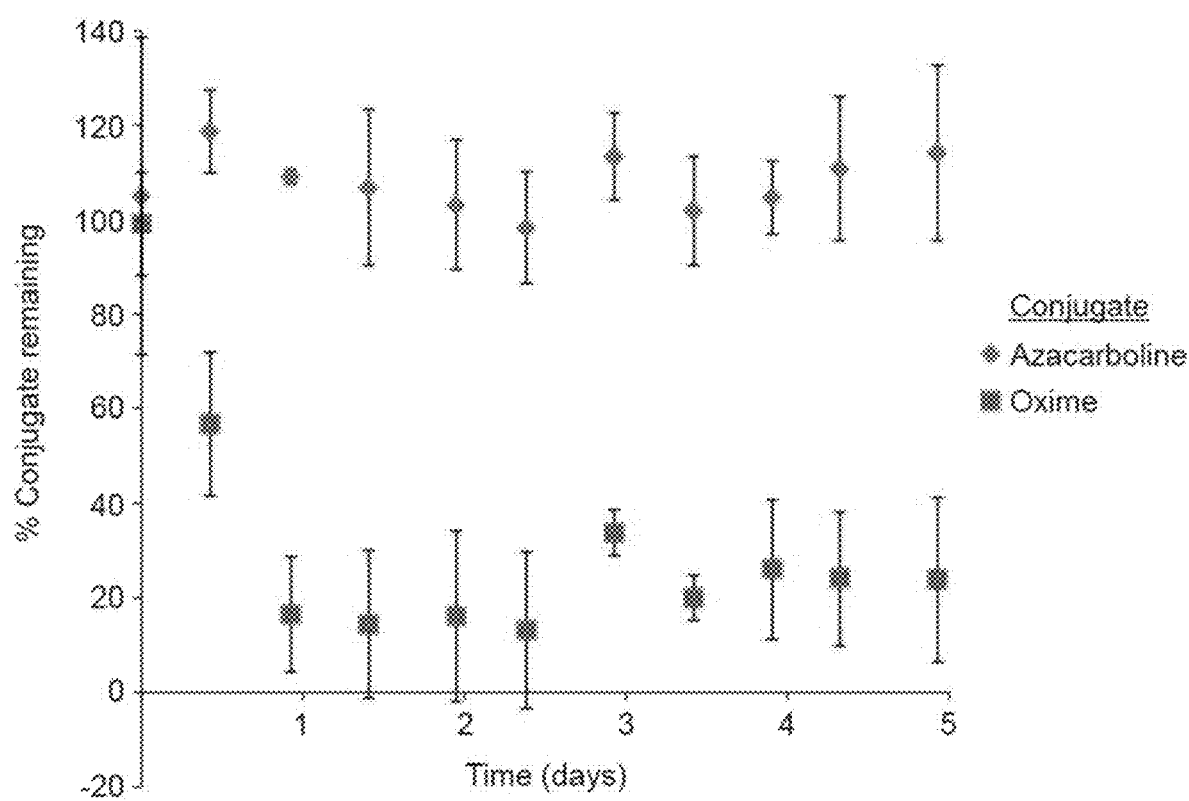
FIG. 8 shows a graph of MBP-AF488 conjugate hydrolysis over 5 days, according to embodiments of the present disclosure. Human plasma containing 10 µg/mL MBP-AF488 conjugate, linked by either an azacarboline or an oxime, was incubated at 37° C. Aliquots taken approximately 12 h apart were analyzed by ELISA. Error bars represent standard deviation of six replicate samples.

As described above, purified azacarboline- and oxime-linked AF488 conjugates of FGly-MBP were incubated at 10 µg/mL in human plasma at 37° C. for five days. Over this time the MBP was monitored for the loss of AF488 by ELISA (FIG. 8). The sandwich ELISA procedure included MBP-AF488 capture on an α-MBP-coated microtiter plate followed by detection of covalently bound AF488 using an α-AF488 antibody and an HRP-conjugated secondary antibody. Over the course of five days, no appreciable hydrolysis of the azacarboline conjugate was observed. In contrast, the oxime conjugate of AF488 decomposed within one day.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate comprising:
at least one modified amino acid residue of formula (I):

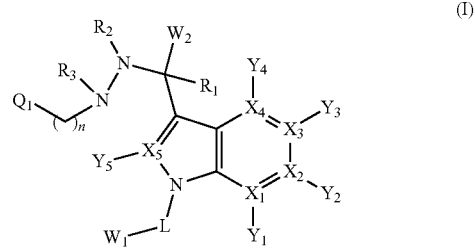

(I)

wherein n is 0 or 1;

$R_1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R_2$ and $R_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$X_1$ is C or N, wherein if $X_1$ is N, then $Y_1$ is absent;

$X_2$, $X_3$ and $X_4$ are each;

$X_5$ is C;

$Y_1$, $Y_2$, $Y_3$, $Y_4$ and $Y_5$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$Q_1$ is a bond to $X_5$ and $Y_5$ is absent; and

L is an optional linker, wherein $W_2$ is an antibody comprising a converted sulfatase motif and $W_1$ is a drug or a detectable label.

2. The conjugate of claim 1, wherein n is 1.

3. The conjugate of claim 1, wherein $R_2$ and $R_3$ are each independently selected from alkyl and substituted alkyl.

4. The conjugate of claim 1, wherein $R_2$ and $R_3$ are each methyl.

5. The conjugate of claim 1, wherein $X_1$, $X_2$, $X_3$ and $X_4$ are each C.

6. The conjugate of claim 1, wherein $Y_1$, $Y_2$, $Y_3$ and $Y_4$ are each H.

7. The conjugate of claim 1, wherein L is present and comprises a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl.

8. The conjugate of claim 1, wherein L is present and comprises a polymer.

9. The conjugate of claim 8, wherein the polymer is a polyethylene glycol.

10. The conjugate of claim 1, wherein the detectable label comprises a fluorophore.

11. The conjugate of claim 1, wherein the conjugate comprises at least one modified amino acid residue of formula (II):

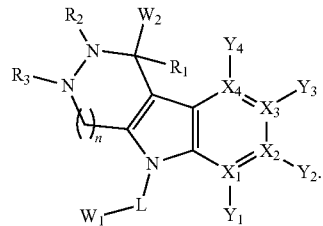

(II)

12. The conjugate of claim 1, wherein the conjugate comprises at least one modified amino acid residue of formula (IIa):

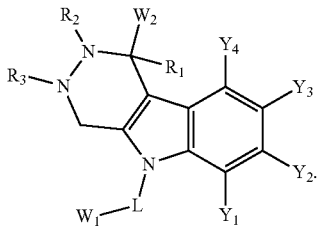

(IIa)

13. A pharmaceutical composition comprising:
a conjugate of claim 1; and
a pharmaceutically acceptable excipient.

14. A method of delivering a conjugate to a subject, the method comprising:
administering to the subject an effective amount of a conjugate of claim 1.

15. The conjugate of claim 1, wherein the antibody is an antibody specific for CD22.

* * * * *